United States Patent
Genin et al.

(10) Patent No.: US 11,919,868 B2
(45) Date of Patent: Mar. 5, 2024

(54) HETEROCYCLIC COMPOUNDS AND RELATED METHODS

(71) Applicant: Recursion Pharmaceuticals, Inc., Salt Lake City, UT (US)

(72) Inventors: Michael James Genin, Draper, UT (US); Joseph Carpenter, Bountiful, UT (US); Carl Brooks, Salt Lake City, UT (US)

(73) Assignee: RECURSION PHARMACEUTICALS, INC., Salt Lake City, UT (US)

( * ) Notice: Subject to any disclaimer, the term of this patent is extended or adjusted under 35 U.S.C. 154(b) by 0 days.

(21) Appl. No.: 17/684,352

(22) Filed: Mar. 1, 2022

(65) Prior Publication Data

US 2022/0380323 A1    Dec. 1, 2022

Related U.S. Application Data

(60) Provisional application No. 63/155,651, filed on Mar. 2, 2021.

(51) Int. Cl.
| | | |
|---|---|---|
| *C07D 471/04* | (2006.01) | |
| *A61K 31/5513* | (2006.01) | |
| *A61P 31/04* | (2006.01) | |
| *C07D 243/30* | (2006.01) | |
| *C07D 487/04* | (2006.01) | |
| *C07D 491/04* | (2006.01) | |
| *C07D 495/04* | (2006.01) | |
| *C07D 498/04* | (2006.01) | |
| *C07D 513/04* | (2006.01) | |

(52) U.S. Cl.
CPC .................. *C07D 243/30* (2013.01)

(58) Field of Classification Search
CPC .. C07D 471/04; C07D 487/04; C07D 491/04; C07D 495/04; C07D 498/04; C07D 513/04; A61K 31/5513; A61P 31/04
See application file for complete search history.

(56) References Cited

FOREIGN PATENT DOCUMENTS

| WO | WO2017/214359 A1 | 12/2017 |
|---|---|---|
| WO | WO2022/187178 A1 | 9/2022 |

OTHER PUBLICATIONS

Letourneau Jeffrey J. et al, "Identification and initial optimization of inhibitors of Clostridium difficile (C. difficiie) toxin B (TcdB)", Bioorganic & Medicinal Chemistry Letters, vol. 28, No. 4, Feb. 1, 2018 (Feb. 1, 2018), p. 756-761, XP055926478 Abtract.
PCT Written Opinion for PCT/US2022/018243 dated Jun. 10, 2022, 6 pages.
PCT International Search Report for PCT/US2022/018243 dated Jun. 10, 2022, 3 pages.

*Primary Examiner* — Brenda L Coleman
(74) *Attorney, Agent, or Firm* — MARSHALL, GERSTEIN & BORUN LLP

(57) ABSTRACT

Provided herein are compounds of Formula (I) and Formula (II) and stereoisomers, tautomers, and pharmaceutically acceptable salts or solvates thereof. Also provided are pharmaceutical compositions comprising these compounds and methods of treating a disease, disorder, or condition by using the compounds and pharmaceutical compositions.

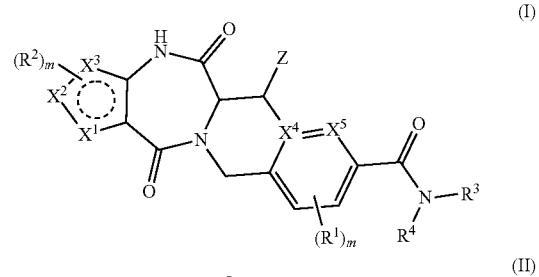

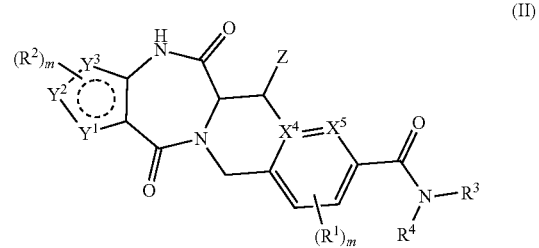

24 Claims, No Drawings

HETEROCYCLIC COMPOUNDS AND RELATED METHODS

CROSS-REFERENCE TO RELATED APPLICATIONS

This application claims the benefit of U.S. Provisional Patent Application No. 63/155,651, filed Mar. 2, 2021 and entitled HETEROCYCLIC COMPOUNDS AND RELATED METHODS, the contents of which are incorporated herein by reference in their entirety.

TECHNICAL FIELD

The present disclosure relates generally to therapeutics. Specifically, the present disclosure relates to heterocyclic compounds and related methods. Pharmaceutical compositions comprising such compounds and their useful therapy are disclosed herein.

BACKGROUND

*Clostridium difficile* (*C. difficile*) is a Gram positive, spore-forming bacterium that causes *C. difficile* associated diarrhea (CDAD). Typically, CDAD occurs after antibiotic treatment-mediated disruption of the intestinal microbiome, but sporadic and environmental cases do occur. There are over 500,000 cases of infection that are associated with over 15-20,000 deaths per year. An estimated 20-40% of the cases are recurrent with patients becoming symptomatic after completing their courses of treatment (Rupnik et al. 2009). The *C. difficile* microorganism produces multiple toxins that disrupt the intestinal lining and lead to inflammation and diarrhea. Two of the toxins that are principally responsible and associated with pathogenesis of human disease are Toxin A and Toxin B (TCdA, TCdB) which are internalized into cells and glucosylate Rho GTPase proteins thereby deactivating a principal mechanism by which cells maintain their shape (Rupnik et al. 2009). This deactivation leads to cell death and disrupts intestinal barrier function leading to inflammation, diarrhea, and, if left untreated toxic megacolon, sepsis, and in some cases, death.

Several antibiotics are commonly used in the treatment of CDAD including metronidazole (off-label), vancomycin, and fidaxomicin (Kelly 2020). However, these treatments result in varying levels of recurrence (Louie et al. 2011) and continue to disrupt the microbiotic flora. Interventions focused on restoring the normal microbiota in the intestines have also shown clinical efficacy (McGovern et al. 2020). However, such therapies are not without significant cost and risks such as transmission of drug-resistant *E. coli* (DeFilipp et al. 2019). Antitoxin antibody therapies are also under active investigation and development. Active vaccination strategies have demonstrated robust immune responses towards the *C. difficile* toxins, however, data on the ability of the vaccines to suppress the pathology of infection is limited, and no vaccine has been approved for the prevention of CDAD (Henderson et al. 2017). Monoclonal antibodies targeted to Toxin B were shown to reduce recurrence from to 8% from 32% (Wilcox et al. 2017). However, the burden of intravenous infusion combined with the high cost of monoclonal antibody therapy can limit its use while competing against other more inexpensive medications, especially for non-hospitalized patients.

Inhibitors of the toxin virulence factors that disrupt barrier function are actively being explored as another option for the treatment of CDAD (Stroke et al. 2018; Bender et al. 2015; Savidge et al. 2011). Such anti virulence strategies have the potential to suppress the pathology without further disrupting the normal flora and providing a selection pressure to promote antibiotic resistance as additional antibiotic therapy prone to do (Fleitas Martinez et al. 2019). The identification of a compound that suppresses the pathology of *C. difficile* infection while preserving and allowing for reconstitution of the normal flora would thus be a highly impactful therapeutic intervention.

SUMMARY OF THE DISCLOSURE

In one aspect, the present disclosure provides compounds of Formula (I), and Formula (II) as well as the subgenera as species thereof, including stereoisomers, tautomers, pharmaceutically acceptable salts, and solvates thereof. In certain embodiments, the compounds are useful to treat *C. difficile* bacterial infections.

In another aspect, the present disclosure also provides processes and intermediates for making the compounds of the present disclosure.

In another aspect, the present disclosure also provides pharmaceutical compositions comprising a pharmaceutically acceptable carrier and at least one of the compounds of the present disclosure or stereoisomers, tautomers, pharmaceutically acceptable salts, or solvates thereof.

In another aspect, the compounds of the disclosure may be used in therapy, either alone or in combination with one or more additional therapeutic agents.

The compounds of the present disclosure may be used in the treatment of a disease, disorder, or condition associated with any infection caused by *C. difficile* bacteria in a patient in need of such treatment by administering a therapeutically effective amount of the compound, or a stereoisomers, tautomers, pharmaceutically acceptable salts, or solvates thereof to the patient. The disease, disorder, or condition may be related to fever, abdominal pain, diarrhea, and colon inflammation. The compounds of the disclosure can be used alone, in combination with one or more compounds of the present disclosure, or in combination with one or more, e.g., one to two, other therapeutic agents.

The compounds of the disclosure may be used for the manufacture of a medicament for the treatment of a disease, disorder, or condition in a patient in need of such treatment.

Other features and advantages of the disclosure will be apparent from the following detailed description and claims.

DETAILED DESCRIPTION

The present application provides compounds, including all stereoisomers, solvates and pharmaceutically acceptable salt and solvate forms thereof, according to Formula (I) and Formula (II). The present application also provides pharmaceutical compositions containing at least one compound according to Formula (I) and Formula (II), or a stereoisomer, a tautomer, or a pharmaceutically acceptable salt or a solvate thereof, and optionally at least one additional therapeutic agent. Additionally, the present application provides methods for treating a patient suffering from a *C. difficile* infection by administering to a patient in need of such treatment a therapeutically effective amount of a compound of the present disclosure, or a stereoisomer, a tautomer, or a pharmaceutically acceptable salt or a solvate thereof, and optionally in combination with at least one additional therapeutic agent.

COMPOUNDS OF THE DISCLOSURE

In one embodiment, the present disclosure provides a compound of Formula (I):

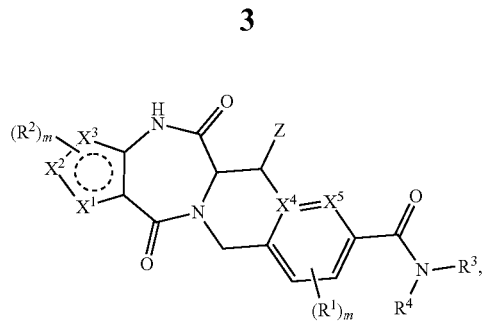

(I)

wherein $X^1$, $X^2$, and $X^3$ are each independently $CR^2$, N, $NR^5$, O, or S; $X^4$ and $X^5$ are each independently C or N;

m is an integer of 0, 1, or 2;

Z is a 6- to 10-membered aryl or, 5- to 10-membered heteroaryl containing 1 to 3 heteroatoms independently selected from N, O, and S.

$R^1$ and $R^2$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;

$R^3$ and $R^4$ are each independently hydrogen, $C_{1-6}$ alkyl, alkylamino, haloalkyl, alkoxy, haloalkoxy, 6- to 10-membered aryl, 5- to 10-membered heteroaryl containing 1 to 3 heteroatoms independently selected from N, O, and S, 3- to 10-membered carbocyclyl, or 4- to 10-membered heterocyclyl containing 1 to 3 heteroatoms independently selected from N, O, and S, wherein the aryl, heteroaryl, carbocyclyl, and heterocyclyl are independently substituted with 0 to 5 $R^5$;

$R^5$ is hydrogen, halo, cyano, hydroxyl, amino, $C_{1-6}$ alkyl, alkylamino, haloalkyl, hydroxyalkyl, hydroxycycloalkyl, aminoalkyl, alkoxyalkyl, haloalkoxyalkyl, alkoxy, haloalkoxy or —$C(O)OR^6$; and $R^6$ is hydrogen or $C_{1-6}$ alkyl.

It should be understood by one skilled in the art that the dashed circle denotes an aromatic ring formed by $X^1$, $X^2$, $X^3$, and the carbon atoms.

In any one of the preceding embodiments of Formula (I), the

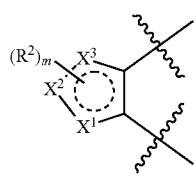

moiety can be

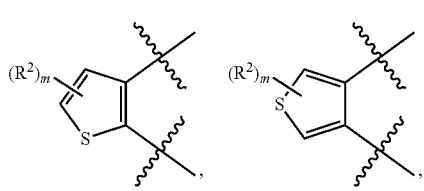

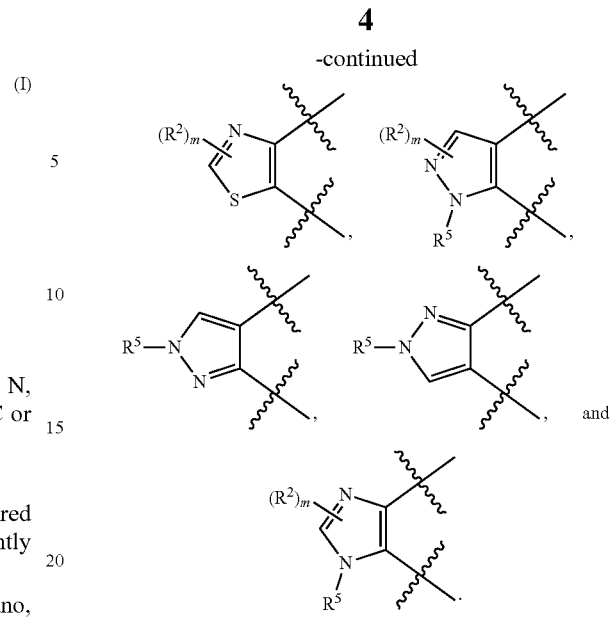

In any one of the preceding embodiments of Formula (I), $R^3$ may be hydrogen and $R^4$ may be a 5- to 10-membered heteroaryl containing 1 to 3 heteroatoms independently selected from N, O, and S, wherein the heteroaryl, is independently substituted with 0 to 5 $R^5$.

In any one of the preceding embodiments of Formula (I), $R^3$ may be hydrogen and $R^4$ may be selected from

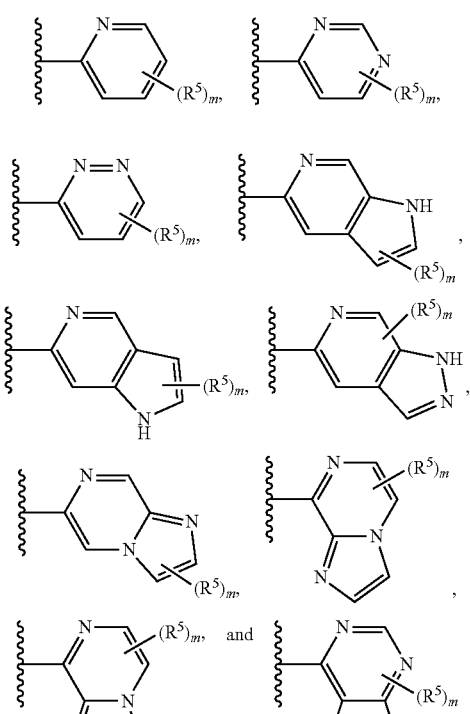

m is an integer of 0, 1 or 2 and $R^5$ is the same as defined above.

In any one of the preceding embodiments of Formula (I), the

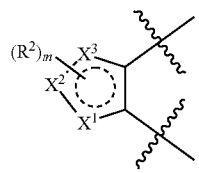

moiety can be

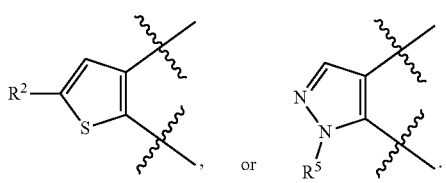

In any one of the preceding embodiments of Formula (I), the compound may be represented by Formula (Ia):

(Ia)

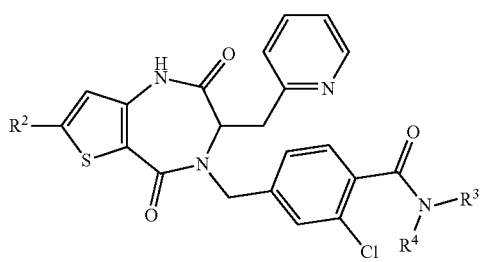

In any one of the preceding embodiments of Formula (I), the compound may be represented by Formula (Ib):

(Ib)

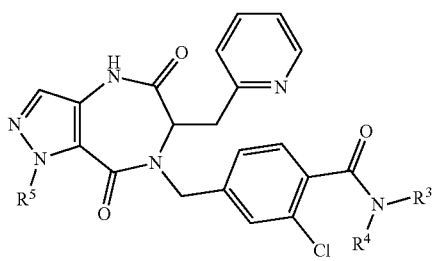

In any one of the preceding embodiments of Formula (I), $R^3$ may be hydrogen and $R^4$ may be selected from

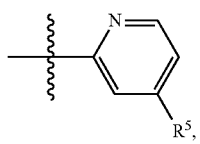

where $R^5$ is as defined above.

In any one of the preceding embodiments of Formula (I), the compound may be represented by Formula (Ic):

(Ic)

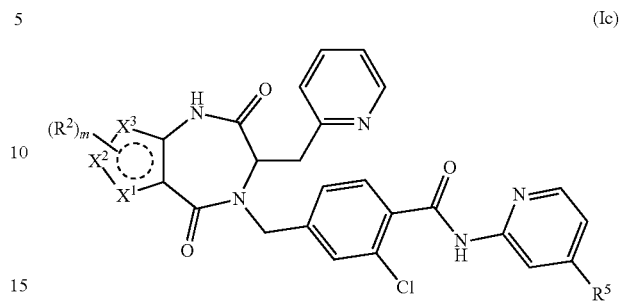

In any one of the preceding embodiments of Formula (I), the compound may be represented by Formula (Id):

(Id)

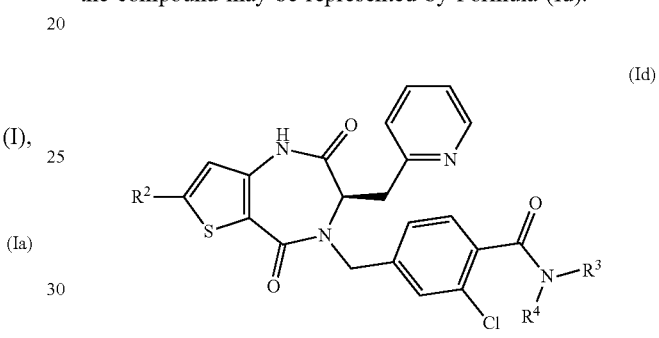

In any one of the preceding embodiments of Formula (I), the compound may be represented by Formula (Ie):

(Ie)

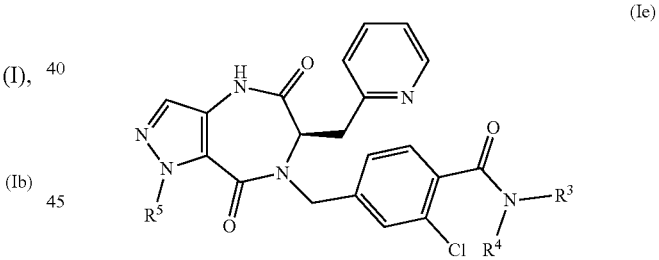

In any one of the preceding embodiments of Formula (I), the compound may be represented by Formula (If):

(If)

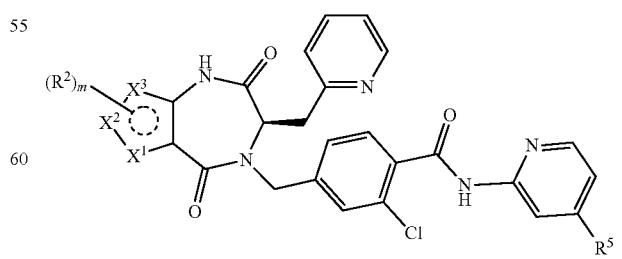

In one embodiment, the present disclosure provides a compound of Formula (II):

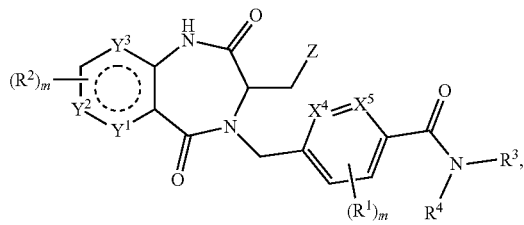
(II)

wherein
- Y$^1$, Y$^2$, and X$^3$ are each independently CR$^2$, or N, provided that at least one Y$^1$, Y$^2$, and Y$^3$ is N;
- X$^4$ and X$^5$ are each independently C or N;
- m is an integer of 0, 1, or 2;
- Z is a 6- to 10-membered aryl or, 5- to 10-membered heteroaryl containing 1 to 3 heteroatoms independently selected from N, O, and S.
- R$^1$ and R$^2$ are each independently hydrogen, halo, cyano, hydroxyl, amino, C$_{1-6}$ alkyl, alkylamino, haloalkyl, hydroxyalkyl, aminoalkyl, alkoxyalkyl, haloalkoxyalkyl, alkoxy, or haloalkoxy;
- R$^3$ and R$^4$ are each independently hydrogen, C$_{1-6}$ alkyl, alkylamino, haloalkyl, alkoxy, or haloalkoxy, 6- to 10-membered aryl, 5- to 10-membered heteroaryl containing 1 to 3 heteroatoms independently selected from N, O, and S, 3- to 10-membered carbocyclyl, or 4- to 10-membered heterocyclyl containing 1 to 3 heteroatoms independently selected from N, O, and S, wherein the aryl, heteroaryl, carbocyclyl, and heterocyclyl are independently substituted with 0 to 5 R$^5$; and R$^5$ is hydrogen, halo, cyano, hydroxyl, amino, C$_{1-6}$ alkyl, alkylamino, haloalkyl, hydroxyalkyl, hydroxycycloalkyl, aminoalkyl, alkoxyalkyl, haloalkoxyalkyl, alkoxy, haloalkoxy or —C(O)OR$^6$; and
- R$^6$ is hydrogen or C$_{1-6}$ alkyl It should be understood by one skilled in the art that the dashed circle denotes an aromatic ring formed by Y$^1$, Y$^2$, Y$^3$, and the carbon atoms.

In any one of the preceding embodiments of Formula (II), the

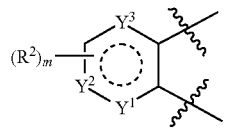

moiety may be selected from

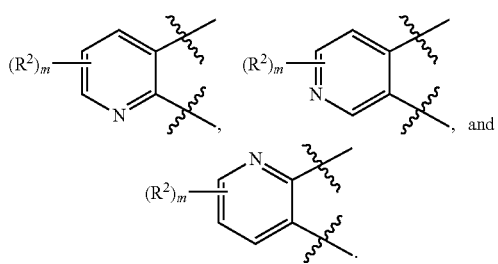

, and

In any one of the preceding embodiments of Formula (II), R$^3$ may be hydrogen and R$^4$ may be a 5- to 10-membered heteroaryl containing 1 to 3 heteroatoms independently selected from N, O, and S, wherein the heteroaryl is independently substituted with 0 to 5 R$^5$.

In any one of the preceding embodiments of Formula (II), R$^3$ may be hydrogen and R$^4$ may be selected from

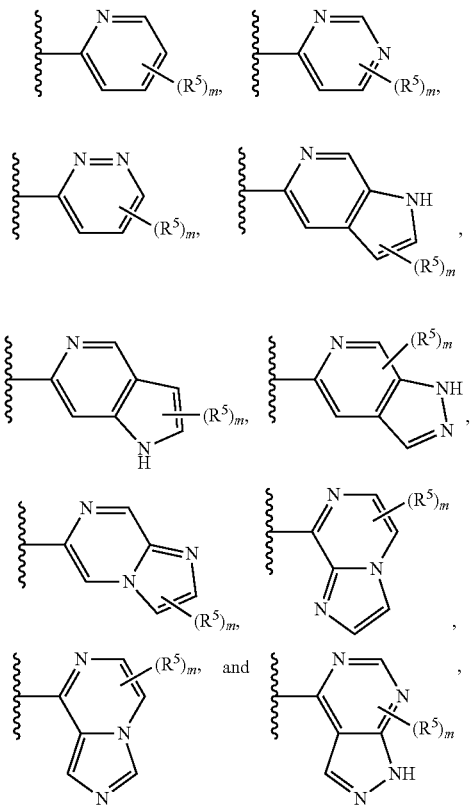

and wherein m is an integer of 0, 1 or 2 and R$^5$ is the same as defined above.

In any one of the preceding embodiments of Formula (II), the

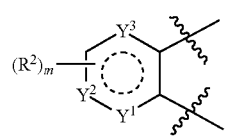

moiety may be

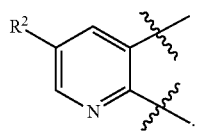

.

In any one of the preceding embodiments of Formula (II), the compound may be represented by Formula (IIa):

(IIa)

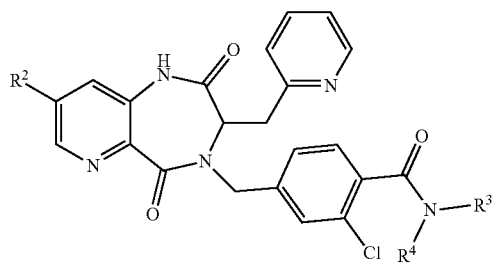

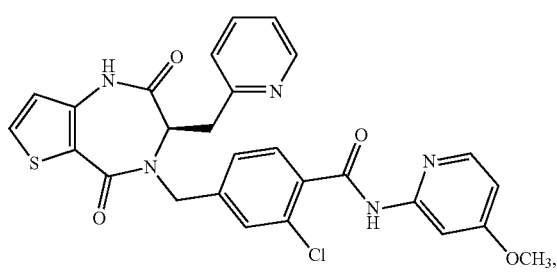

In any one of the preceding embodiments of Formula (II), the compound may be represented by Formula (IIb):

(IIb)

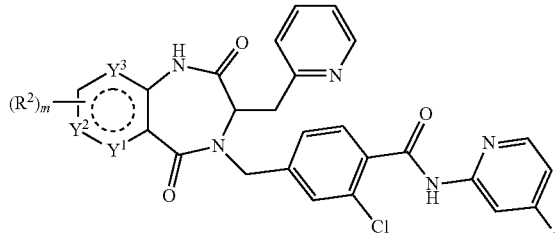

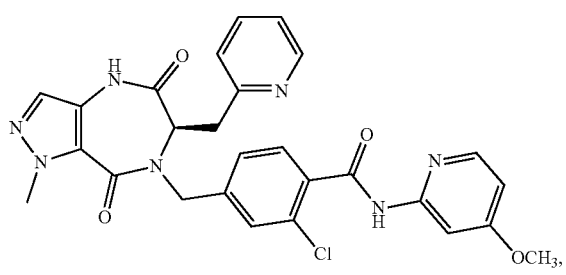

In any one of the preceding embodiments of Formula (II), the compound may be represented by Formula (IIc):

(IIc)

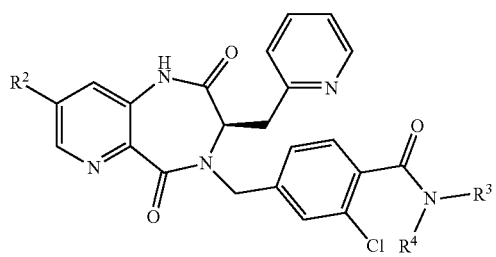

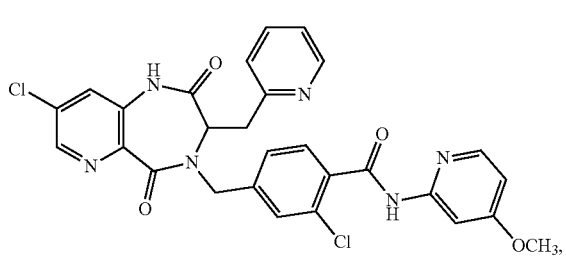

In any one of the preceding embodiments of Formula (II), the compound may be represented by Formula (IId):

(IId)

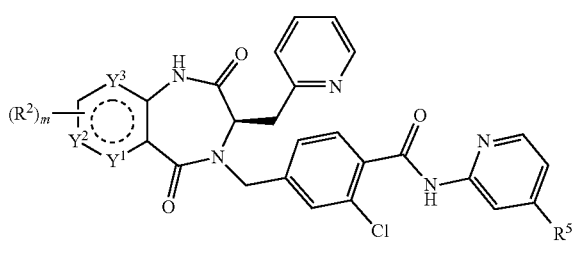

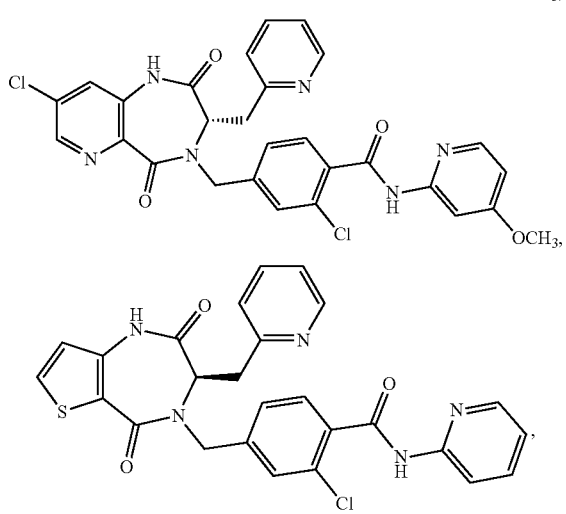

In one embodiment, the present disclosure provides compounds that may be selected from:

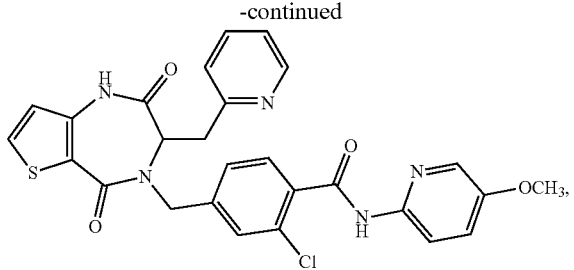
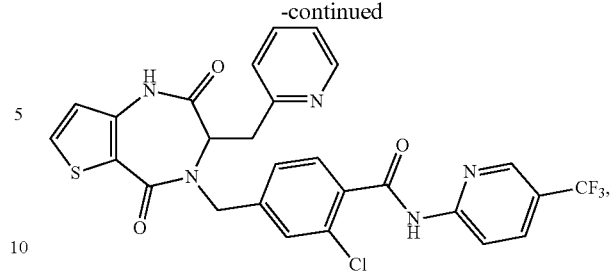
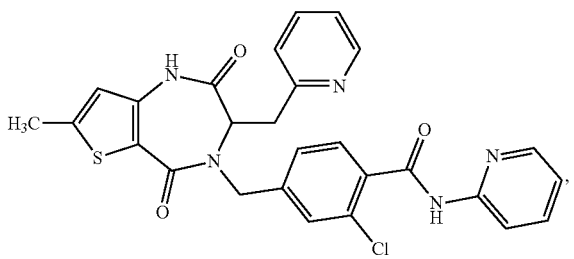
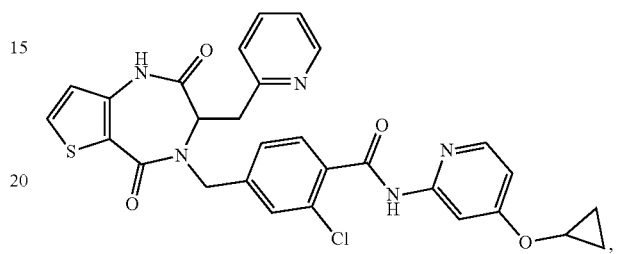
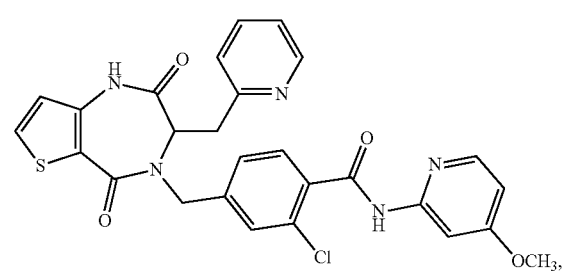
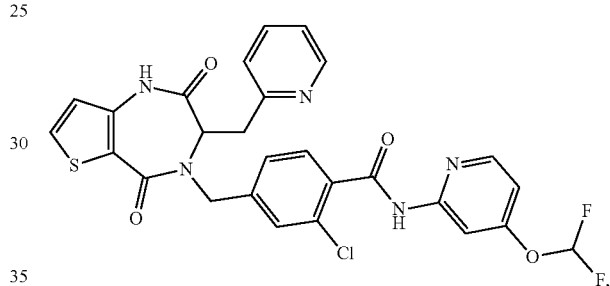
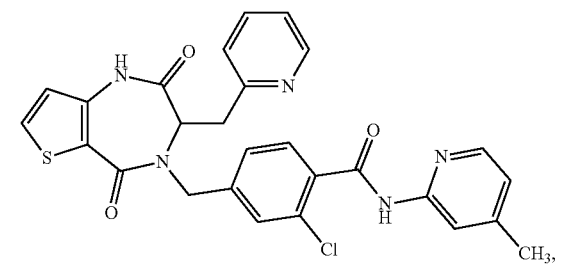
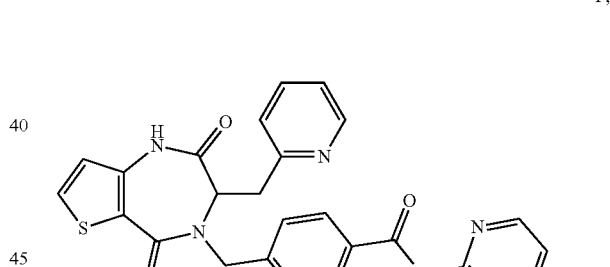
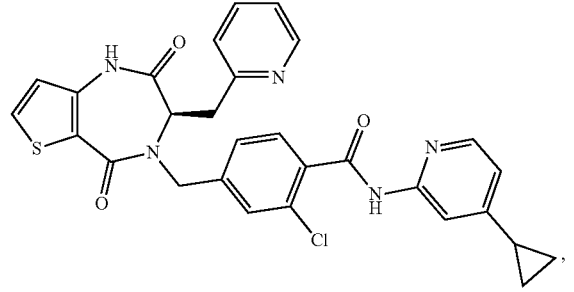
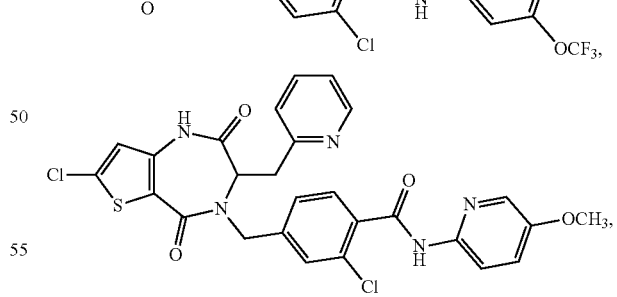
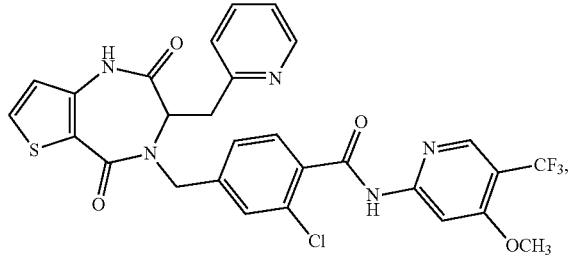
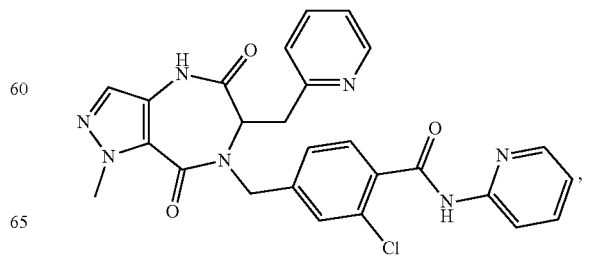

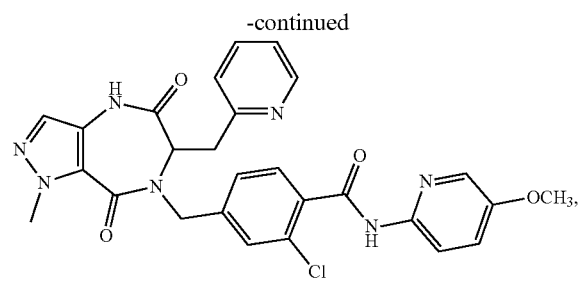
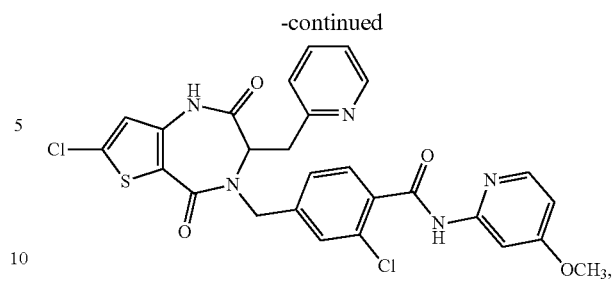
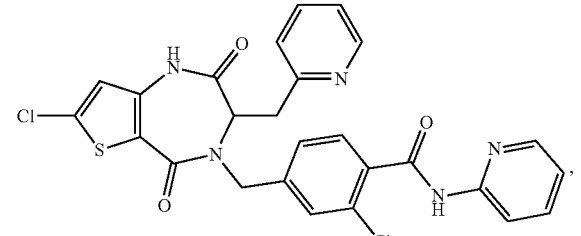
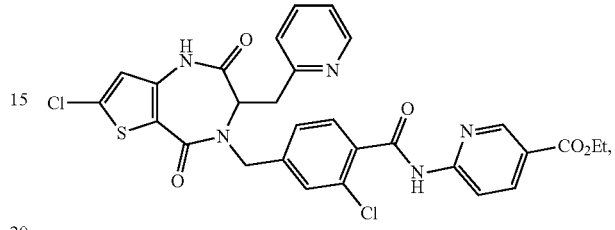
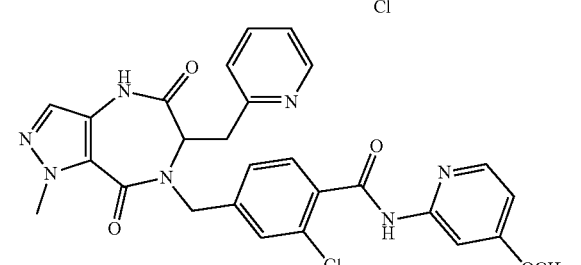
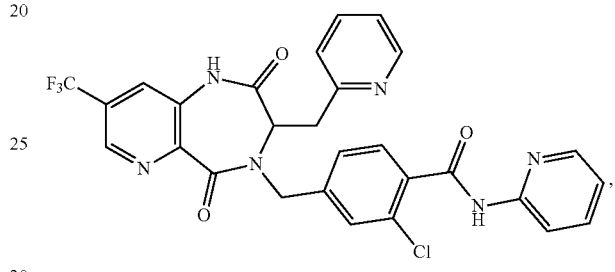
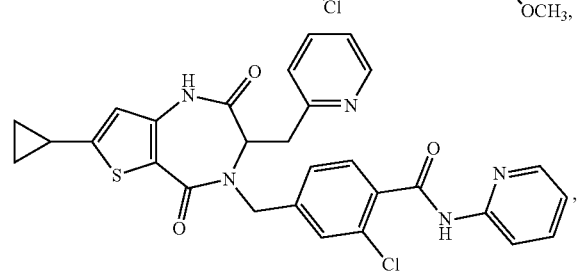
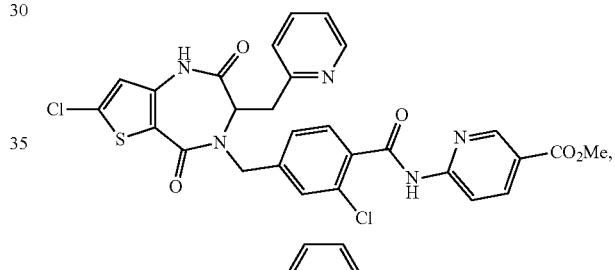
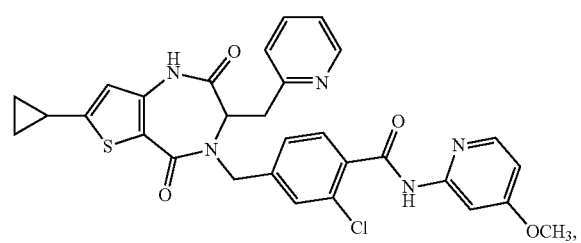
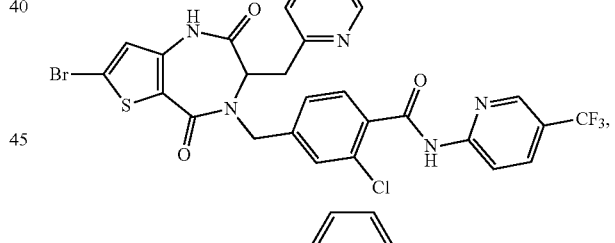
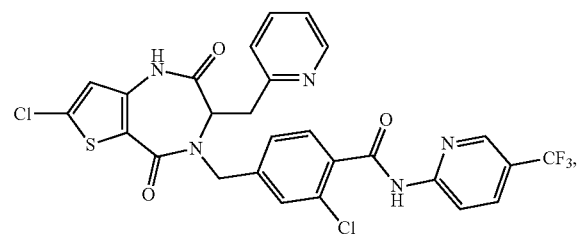
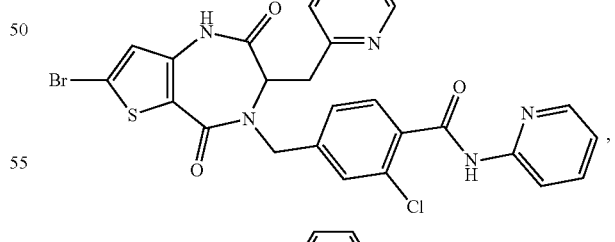
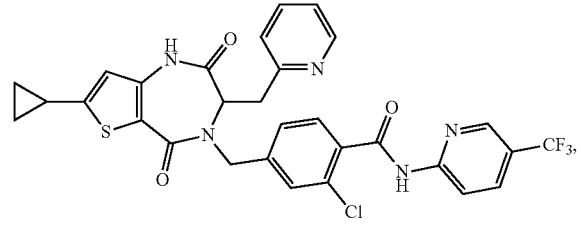
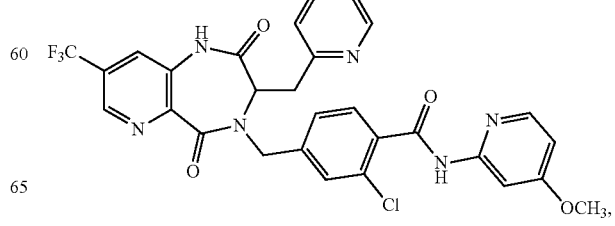

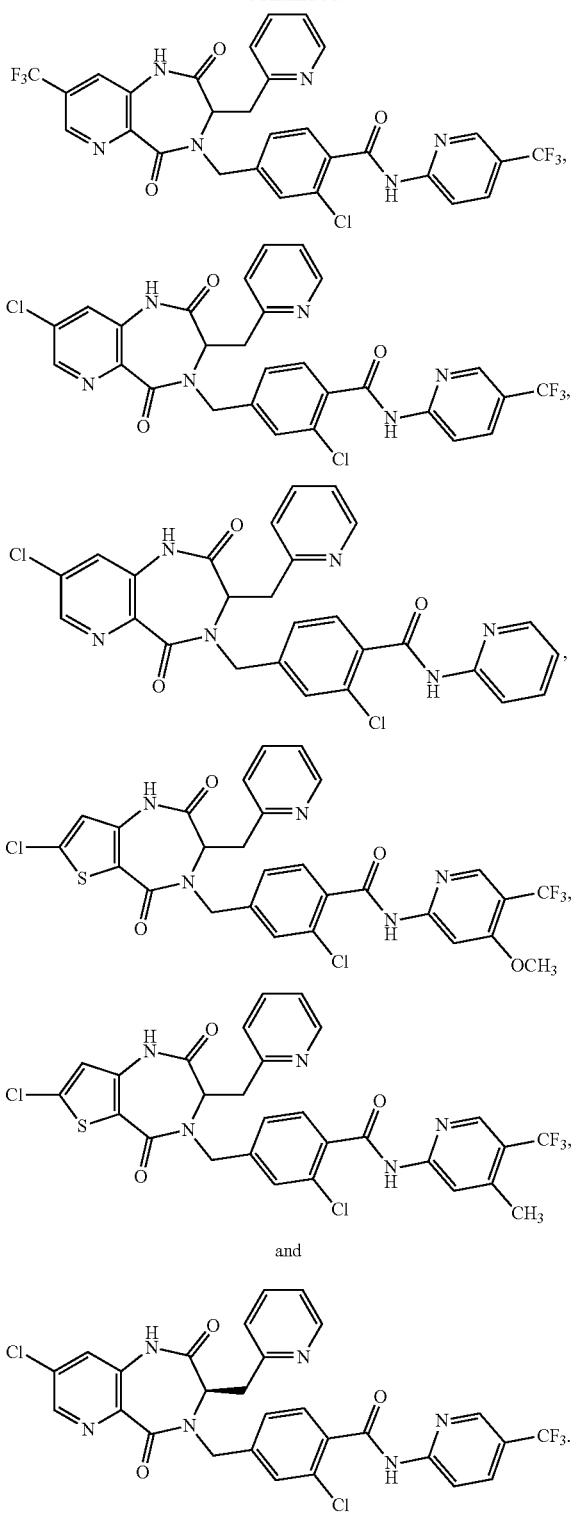

or a stereoisomer, a tautomer, or a pharmaceutically acceptable salt or solvate thereof.

In one embodiment, the present disclosure provides, inter alia, compounds selected from any one of the Examples as described in the specification, or a stereoisomer, a tautomer, or a pharmaceutically acceptable salt or solvate thereof.

II. Pharmaceutical Compositions, Therapeutic Utilities, and Combinations

In another embodiment, the present disclosure provides a composition comprising at least one of the compounds of the present disclosure, or a stereoisomer, a tautomer, or a pharmaceutically acceptable salt or a solvate thereof. In another embodiment, the present disclosure provides a pharmaceutical composition comprising a pharmaceutically acceptable carrier and at least one of the compounds of the present disclosure or a stereoisomer, a tautomer, or a pharmaceutically acceptable salt or a solvate thereof.

In another embodiment, the present disclosure provides a pharmaceutical composition, comprising a pharmaceutically acceptable carrier and a therapeutically effective amount of at least one of the compounds of the present disclosure or a stereoisomer, a tautomer, or a pharmaceutically acceptable salt or a solvate thereof.

In another embodiment, the present disclosure provides a process for making a compound of the present disclosure.

In another embodiment, the present disclosure provides an intermediate for making a compound of the present disclosure.

In another embodiment, the present disclosure provides a pharmaceutical composition as defined above further comprising one or more additional therapeutic agents.

In another embodiment, the present disclosure provides a method for the treatment of a disease, disorder, or condition associated with *C. difficile* infection in a patient in need of such treatment, and the method comprises administering a therapeutically effective amount of a compound of the present disclosure, or a stereoisomer, a tautomer, or a pharmaceutically acceptable salt or solvate thereof, to the patient.

In another embodiment, the present disclosure provides a method for the treatment of the disease, disorder, or condition comprising administering to a patient in need of such treatment a therapeutically effective amount of at least one of the compounds of the present disclosure, alone, or, optionally, in combination with another compound of the present disclosure and/or at least one other type of therapeutic agent.

In another embodiment, the present disclosure provides a method of inhibiting a *C. difficile* bacterial toxin in a cell, and the method comprises administering a therapeutically effective amount of a compound of the present disclosure, or a stereoisomer, a tautomer, or a pharmaceutically acceptable salt or solvate thereof, to the cell. In particular embodiments, the toxin is toxin B.

In another embodiment, the present disclosure provides a method reducing glucosylation of Rho GTPase proteins in a cell, and the method comprises administering a therapeutically effective amount of a compound of the present disclosure, or a stereoisomer, a tautomer, or a pharmaceutically acceptable salt or solvate thereof, to the cell.

The compounds of this disclosure can be administered for any of the uses described herein by any suitable means, for example, orally, such as tablets, capsules (each of which includes sustained release or timed-release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the disclosure in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and nonaqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present disclosure. For purposes of this disclosure, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

As used herein, the phrase "treating . . . with . . . a compound" or "administering a . . . compound" includes either administering a compound of the present disclosure, or a pharmaceutical compositions comprising a compound of the present disclosure, directly to isolated cells or to an animal, or administering to cells or an animal another agent to cause the presence or formation of a compound of the present disclosure inside the cells or the animal. Preferably, the methods of the present disclosure comprise administering to cells in vitro or to a warm-blood animal, particularly mammal, and more particularly a human, a pharmaceutical composition comprising an effective amount of a compound according to the present disclosure causing the presence or formation of the compound of the present disclosure inside the cells or the animal.

The dosage regimen for the compounds of the present disclosure will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. By way of general guidance, the daily oral dosage of each active ingredient, when used for the indicated effects, will range between about 0.01 to about 5000 mg per day, preferably between about 0.01 to about 1000 mg per day, and most preferably between about 0.01 to about 250 mg per day. Intravenously, the most preferred doses will range from about 0.01 to about 10 mg/kg/minute during a constant rate infusion. Compounds of this disclosure may be administered in a single daily dose, or the total daily dosage may be administered in divided doses of two, three, or four times daily. The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices. Dosage forms (pharmaceutical compositions) suitable for administration may contain from about 0.1 milligram to about 2000 milligrams of active ingredient per dosage unit. In these pharmaceutical compositions the active ingredient will ordinarily be present in an amount of about 0.1-95% by weight based on the total weight of the composition. A typical capsule for oral administration contains at least one of the compounds of the present disclosure (250 mg), lactose (75 mg), and magnesium stearate (15 mg). The mixture is passed through a 60-mesh sieve and packed into a No. 1 gelatin capsule. A typical injectable preparation is produced by aseptically placing at least one of the compounds of the present disclosure (250 mg) into a vial, aseptically freeze-drying and sealing. For use, the contents of the vial are mixed with 2 mL of physiological saline, to produce an injectable preparation.

The present disclosure includes within its scope pharmaceutical compositions comprising, as an active ingredient, a therapeutically effective amount of at least one of the compounds of the present disclosure, alone or in combination with a pharmaceutical carrier. Optionally, compounds of the present disclosure can be used alone, in combination with other compounds of the disclosure, or in combination with one or more, preferably one to three, other therapeutic agent(s), e.g., vancomycin, fidaxomicin, metronidazole or other pharmaceutically active material.

The above other therapeutic agents, when employed in combination with the compounds of the present disclosure may be used, for example, in those amounts indicated in the *Physicians' Desk Reference,* as in the patents set out above, or as otherwise determined by one of ordinary skill in the art.

Particularly when provided as a single dosage unit, the potential exists for a chemical interaction between the combined active ingredients. For this reason, when the compound of the present disclosure and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present disclosure, whether administered in a single dosage form or administered in separate forms but at the same time by the same manner, will be readily apparent to those skilled in the art, once armed with the present disclosure.

The compounds of the present disclosure can be administered alone or in combination with one or more, preferably one to three, additional therapeutic agents. By "administered in combination" or "combination therapy" it is meant that the compound of the present disclosure and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present disclosure are also useful as standard or reference compounds, for example as a quality standard or control, in tests or assays involving *C. difficile* toxin antagonists. Such compounds may be provided in a commercial kit, for example, for use in pharmaceutical research involving *C. difficile* toxin antagonist activity. For example, a compound of the present disclosure could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present disclosure could be used to test their effectiveness.

The present disclosure also encompasses an article of manufacture. As used herein, article of manufacture is intended to include, but not be limited to, kits and packages. The article of manufacture of the present disclosure, comprises: (a) a first container; (b) a pharmaceutical composition located within the first container, wherein the composition, comprises: a first therapeutic agent, comprising a compound of the present disclosure or a pharmaceutically acceptable salt form thereof; and, (c) a package insert stating that the pharmaceutical composition can be used for the treatment of *C. difficile* infections and the sequelae thereof. In another embodiment, the package insert states that the pharmaceutical composition can be used in combination (as defined previously) with a second therapeutic agent for the treatment of *C. difficile* infections and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

III. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present in the compounds, and all such stable isomers are contemplated in the present disclosure. Cis- and trans- (or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography or fractional crystallization. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. As used herein, "a compound of the disclosure" or "compounds of the disclosure" means one or more compounds encompassed by any one of Formula (I), and (II), or stereoisomers, tautomers, or pharmaceutically acceptable salts or solvates thereof.

As used herein, the term "alkyl" or "alkylene" is intended to include both branched and straight-chain saturated aliphatic hydrocarbon groups having the specified number of carbon atoms. While "alkyl" denotes a monovalent saturated aliphatic radical (such as ethyl), "alkylene" denotes a bivalent saturated aliphatic radical (such as ethylene). For example, "$C_1$ to $C_{10}$ alkyl" or "$C_{1-10}$ alkyl" is intended to include $C_1$, $C_2$, $C_3$, $C_4$, $C_5$, $C_6$ $C_7$, $C_8$, $C_9$, and $C_{10}$ alkyl groups. "$C_1$ to $C_{10}$ alkylene" or "$C_{1-10}$ alkylene", is intended to include $C_1$, $C_2$, $C_3$, $C_4$, $C_5$, $C_6$ $C_7$, $C_8$, $C_9$, and $C_{10}$ alkylene groups. Additionally, for example, "$C_1$ to $C_6$ alkyl" or "$C_{1-6}$ alkyl" denotes alkyl having 1 to 6 carbon atoms; and "$C_1$ to $C_6$ alkylene" or "$C_{1-6}$ alkylene" denotes alkylene having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH3, etc.), an alkylamino (e.g., —NHCH$_3$, —N(CH$_3$)$_2$, etc.), or a thioalkyl group (e.g., —SCH$_3$). If a nonterminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), an alkylaminoalkyl (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. While "alkenyl" denotes a monovalent radical, "alkenylene" denotes a bivalent radical. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. While "alkynyl" denotes a monovalent radical, "alkynylene" denotes a bivalent radical. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or sp$^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, such as —OH, —OCH$_3$, Cl, F, Br, I, —CN, —NO$_2$, —NH$_2$, —NH(CH$_3$), —N(CH$_3$)$_2$, —CF$_3$, —OCF$_3$, —C(=O)CH$_3$, —SCH$_3$, —S(=O)CH$_3$, —S(=O)$_2$CH$_3$, —CH$_3$, —CH$_2$CH$_3$, —CO$_2$H, and —CO$_2$CH$_3$. "Benzyl" can also be represented by formula "Bn".

The term "lower alkoxy", "alkoxy" or "alkyloxy", "aryloxy" or "aralkoxy" refers to any of the above alkyl, aralkyl or aryl groups linked to an oxygen atom. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "lower alkylthio", "alkylthio", "thioalkoxy", "arylthio", or "aralkylthio" represents an alkyl, aryl, or aralkyl group as defined above with the indicated number of carbon atoms attached through a sulfur bridge; for example methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "$C_1$ to $C_6$ alkylcarbonyl" (or alkylcarbonyl), is intended to include $C_1$, $C_2$, $C_3$, $C_4$, $C_5$, and $C_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by —S(O)$_2$R', while sulfonamide may be represented by —S(O)$_2$NR$^c$R$^d$. R' is $C_1$ to $C_6$ alkyl; and R$^c$ and R$^d$ are the same as defined below for "amino".

The term "carbamate" as used herein alone or as part of another group refers to oxygen linked to an amido group. For example, carbamate may be represented by N(R$^c$R$^d$)—C(O)—O—, and R$^c$ and R$^d$ are the same as defined below for "amino".

The term "amido" as used herein alone or as part of another group refers to amino linked to a carbonyl group. For example, amido may be represented by N(R$^c$R$^d$)—C(O)—, and R$^c$ and R$^d$ are the same as defined below for "amino".

The term "amino" is defined as —NR$^{c1}$R$^{c2}$, wherein R$^{c1}$ and R$^{c2}$ are independently H or $C_{1-6}$ alkyl; or alternatively, R$^{c1}$ and R$^{c2}$, taken together with the atoms to which they are attached, form a 3- to 8-membered heterocyclic ring which is optionally substituted with one or more group selected from such as halo, cyano, hydroxyl, amino, oxo, $C_{1-6}$ alkyl, alkoxy, and aminoalkyl. When R$^{c1}$ or R$^{c2}$ (or both of them) is $C_{1-6}$ alkyl, the amino group can also be referred to as alkylamino. Examples of alkylamino group include, without limitation, —NH$_2$, methylamino, ethylamino, propylamino, isopropylamino and the like.

The term "aminoalkyl" refers to an alkyl group on which one of the hydrogen atoms is replaced by an amino group. For example, aminoalkyl may be represented by N(R$^{c1}$R$^{c2}$)-alkylene-"$C^1$ to $C_6$" or "$C_{1-6}$" aminoalkyl" (or aminoalkyl), is intended to include $C_1$, $C_2$, $C_3$, $C_4$, $C_5$, and $C_6$ aminoalkyl groups.

The term "halogen" or "halo" as used herein alone or as part of another group refers to chlorine, bromine, fluorine, and iodine, with chlorine or fluorine being preferred. "Haloalkyl" is intended to include both branched and straight-chain saturated aliphatic hydrocarbon groups having the specified number of carbon atoms, substituted with one or more halogens. "$C_1$ to $C_6$ haloalkyl" or "$C_{1-6}$ haloalkyl" (or haloalkyl), is intended to include $C_1$, $C_2$, $C_3$, $C_4$, $C_5$, and $C_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms. The term "polyhaloalkyl" as used herein refers to an "alkyl" group as defined above which includes from 2 to 9, preferably from 2 to 5, halo substituents, such as F or Cl, preferably F, such as polyfluoroalkyl, for example, —CH$_2$CF$_3$, —CF$_3$, or —CH$_2$CF$_2$CF$_3$.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above includes from 2 to 9, preferably from 2 to 5, halo substituents, such as F or Cl, preferably F, such as polyfluoroalkoxy, for example, —OCH$_2$CF$_3$, —OCF$_3$, or —OCH$_2$CF$_2$CF$_3$.

"Hydroxyalkyl" is intended to include both branched and straight-chain saturated aliphatic hydrocarbon groups having the specified number of carbon atoms, substituted with 1 or more hydroxyl (OH). "$C_1$ to $C_6$ hydroxyalkyl" (or hydroxyalkyl), is intended to include $C_1$, $C_2$, $C_3$, $C_4$, $C_5$, and $C_6$ hydroxyalkyl groups.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems. "$C_3$ to $C_7$ cycloheteroalkyl" or "$C_{3-7}$ cycloheteroalkyl" is intended to include $C_3$, $C_4$, $C_5$, $C_6$, and $C_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic" is intended to mean any stable 3-, 4-, 5-, 6-, 7-, or 8-membered monocyclic or 5-, 6-, 7-, 8-, 9-, 10-, 11-, 12-, or 13-membered polycyclic (including bicyclic or tricyclic) hydrocarbon ring, any of which may be saturated or partially unsaturated. That is, the term "carbocycle", "carbocyclyl", or "carbocyclic" includes, without limitation, cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, indanyl, adamantyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, indanyl, and tetrahydronaphthyl. A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons or 3 to 6 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

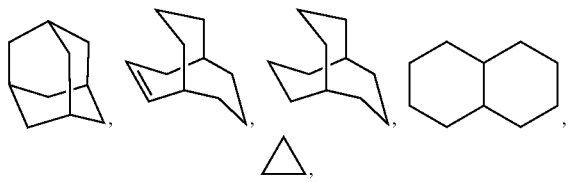

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated or partially unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, such as selected from —OH, —OCH$_3$, F, Cl, Br, I, —CN, —NO$_2$, —NH$_2$, —NH(CH$_3$), —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from the group consisting of N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of heterocyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, and dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle). The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1.2.3.4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1.2.3.4-tetrahydro-quinazolinyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N—O and $S(O)_p$, wherein p is 0, 1 or 2).

Examples of heteroaryl include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4a//-carbazolyl, carbolinyl, chromanyl, chromenyl, cinnolinyl, decahydroquinolinyl, 2H,6H-1,5,2-dithiazinyl, furanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4//-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings, for example,

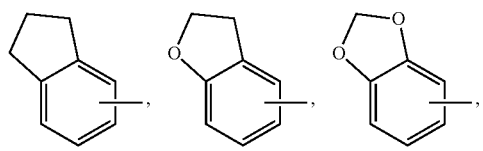

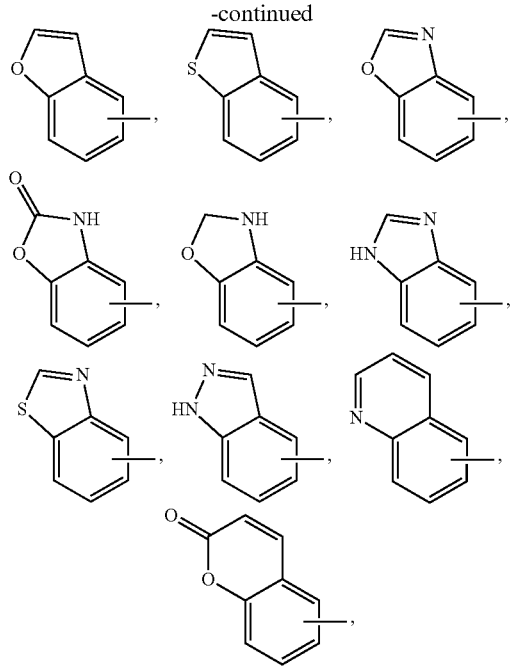

and may be optionally substituted through available carbon atoms with 1, 2, or 3 groups selected from such as hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxy carbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

When any of the terms alkyl, alkenyl, alkynyl, cycloalkyl, carbocyclyl, heterocyclyl, aryl, and heteroaryl are used as part of another group, the number of carbon atoms and ring members are the same as those defined in the terms by themselves. For example, alkoxy, haloalkoxy, alkylamino, haloalkyl, hydroxyalkyl, aminoalkyl, haloalkoxy, alkoxyalkoxy, haloalkylamino, alkoxyalkylamino, haloalkoxyalkylamino, alkylthio, and the like each independently contains the number of carbon atoms which are the same as defined for the term "alkyl", such as 1 to 4 carbon atoms, 1 to 6 carbon atoms, 1 to 10 carbon atoms, etc. Similarly, cycloalkoxy, heterocyclyloxy, cycloalkylamino, heterocyclylamino, aralkylamino, arylamino, aryloxy, aralkyloxy, heteroaryloxy, heteroarylalkyloxy, and the like each independently contains ring members which are the same as defined for the terms "cycloalkyl", "heterocyclyl", "aryl", and "heteroaryl", such as 3 to 6-membered, 4 to 7-membered, 6 to 10-membered, 5 to 10-membered, 5 or 6-membered, etc.

In accordance with a convention used in the art, a bond pointing through a wavy or squiggly line, such as

as used in structural formulas herein, depicts the bond that is the point of attachment of the moiety or substituent to the core or backbone structure.

In accordance with a convention used in the art, a wavy or squiggly bond in a structural formula, such as

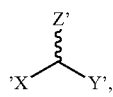

is used to depict a stereogenic center of the carbon atom to which X', Y' and Z' are attached and is intended to represent both enantiomers in a single figure. That is, a structural formula with such a wavy bond denotes each of the enantiomers individually, such as

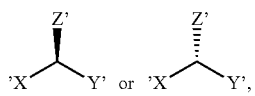

as well as a racemic mixture thereof. When a wavy or squiggly bond is attached to a double bond (such as C=C or C=N) moiety, it includes cis- or trans- (or E- and Z-) geometric isomers or a mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present disclosure should be selected in order to provide a compound which is sufficiently stable to provide a pharmaceutically useful compound which can be formulated into an acceptably stable pharmaceutical composition. Compounds of the present disclosure which have such stability are contemplated as falling within the scope of the present disclosure.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom (attached to carbon atom or heteroatom) is replaced with a non-hydrogen group, provided that normal valencies are maintained and that the substitution results in a stable compound. When a substituent is oxo (i.e., =O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N). The term "substituted" in reference to alkyl, cycloalkyl, heteroalkyl, cycloheteroalkyl, alkylene, aryl, arylalkyl, heteroaryl, heteroarylalkyl, carbocyclyl, and heterocyclyl, means alkyl, cycloalkyl, heteroalkyl, cycloheteroalkyl, alkylene, aryl, arylalkyl, heteroaryl, heteroarylalkyl, carbocyclyl, and heterocyclyl, respectively, in which one or more hydrogen atoms, which are attached to either carbon or heteroatom, are each independently replaced with one or more non-hydrogen substituent(s).

In cases wherein there are nitrogen atoms (e.g., amines) on compounds of the present disclosure, these may be converted to N-oxides by treatment with an oxidizing agent (e.g., mCPBA and/or hydrogen peroxides) to afford other compounds of this disclosure. Thus, shown and claimed nitrogen atoms are considered to cover both the shown nitrogen and its N-oxide (N—O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium and are readily interchanged by migration of an atom or group within the molecule. For example, one skilled in the art would readily understand that a 1,2,3-triazole exists in two tautomeric forms as defined above:

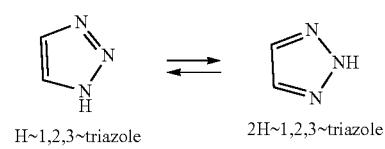 [SMILES: c1c[nH]nn1 ; c1cn[nH]n1]

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present disclosure can be present as salts, which are also within the scope of this disclosure. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, PA (1990), the disclosure of which is hereby incorporated by reference.

If the compounds of the present disclosure have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxy carboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluenesulfonic acid. Corresponding acid addition salts can also be formed having, if desired, an additionally present basic center. The compounds of the present disclosure having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula (I) and Formula (II) or their pharmaceutically acceptable salts, are also included.

Preferred salts of the compounds of Formula (I) and Formula (II) which contain a basic group include monohydrochloride, hydrogensulfate, methanesulfonate, phosphate, nitrate or acetate.

Preferred salts of the compounds of Formula (I) and Formula (II) which contain an acid group include sodium, potassium and magnesium salts and pharmaceutically acceptable organic amines.

In addition, the compounds of the present disclosure may have prodrug forms. Any compound that will be converted in vivo to provide the bioactive agent is a prodrug within the scope and spirit of the disclosure. The term "prodrug" as used herein encompasses both the prodrugs based on the carboxylic acid residue, i.e., "prodrug esters", and the prodrugs based on the arginine mimetics moiety, i.e., "prodrugs of arginine mimetics" Such prodrugs are preferably administered orally since hydrolysis in many instances occurs principally under the influence of the digestive enzymes. Parenteral administration may be used where the ester per se is active, or in those instances where hydrolysis occurs in the blood.

The compounds of the present disclosure contain a carboxy group which can form physiologically hydrolyzable esters that serve as prodrugs, i.e., "prodrug esters", by being hydrolyzed in the body to yield the compounds of the present disclosure per se. Examples of physiologically hydrolyzable esters of compounds of the present disclosure include $C_1$ to $C_6$ alkyl, $C_1$ to $C_6$ alkylbenzyl 1,4-methoxybenzyl, indanyl, phthalyl, methoxymethyl, $C_{1-6}$ alkanoyloxy, $C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3 dioxolen-4-yl)-methyl), and other well-known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present disclosure with either alkyl or aryl alcohol, halide, or sulfonate employing procedures known to those skilled in the art. Furthermore, various forms of prodrugs are well known in the art. For examples of such prodrug derivatives, see:

Bundgaard, H., ed., *Design of Prodrugs*, Elsevier (1985), and Widder, K. et al, eds., *Methods in Enzymology,* 112: 309-396, Academic Press (1985);

Bundgaard, H., Chapter 5, "Design and Application of Prodrugs", Krosgaard-Larsen, P. et al, eds., *A Textbook of Drug Design and Development*, pp. 113-191, Harwood Academic Publishers (1991);

Bundgaard, H., *Adv. Drug Deliv. Rev.,* 8:1-38 (1992);

Bundgaard, H. et al., *J Pharm. Sci.,* 77:285 (1988); and

Kakeya, N. et al., *Chem. Pharm. Bull.,* 32:692 (1984).

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry*, Academic Press, San Diego, CA (1999); Rautio, J. et al., *Nature Review Drug Discovery,* 17, 559-587, (2018).

The present disclosure is intended to include all isotopes of atoms occurring in the present compounds. Isotopes include those atoms having the same atomic number but different mass numbers. By way of general example and without limitation, isotopes of hydrogen include deuterium (symbol D or $^2H$) and tritium (symbol T or $^3H$). Isotopes of carbon include $^{13}C$ and $^{14}C$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this disclosure bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present disclosure do not contain a N-halo, S(O)$_2$H, or S(O)H group.

The term "solvate" means a physical association of a compound of this disclosure with one or more solvent molecules, whether organic or inorganic. This physical association includes hydrogen bonding. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "pL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "cone." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "1H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Abbreviations

The following abbreviations are employed in the Schemes, Examples and elsewhere herein:
Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxy carbonyl
Boc$_2$O di-tert-butyl dicarbonate
ACN or CH$_3$CN acetonitrile
AcOH or HOAc acetic acid
AlCl$_3$ aluminum chloride
AlBN Azobisisobutyronitrile
BBr$_3$ boron tribromide
BCl$_3$ boron trichloride
BEMP 2-tert-butylimino-2-diethylamino-1.3-dimethylperhydro-1.3.2-diazaphosphorine
BOP reagent benzotriazol-1-yloxytris(dimethylamino)phosphonium hexafluorophosphate
Burgess reagent 1-methoxy-N-triethylammoniosulfonylmethanimidate
CBz carbobenzyloxy
DCM or CH$_2$Cl$_2$ dichloromethane
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DEA diethylamine
DMP or Dess-Martin Periodinane 1,1,1-tris(acetyloxy)-1,1-dihydro-1,2-beniziodoxol-3-(1H)-one
DIC or DIPCDI diisopropylcarbodiimide
DIEA, DIPEA or Hunig's base diisopropylethylamine
DMAP 4-dimethylaminopyridine
DME 1,2-dimethoxy ethane
DMF dimethyl formamide
DMSO dimethyl sulfoxide
cDNA complimentary DNA
Dppp (R)-(+)-1.2-bis(diphenylphosphino)propane
DuPhos (+)-1,2-bis((2S,5S)-2,5-diethylpholano)benzene
EDC N-(3-dimethylaminopropyl)-N'-ethylcarbodiimide
EDCI N-(3-dimethylaminopropyl)-N-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA triethylamine
EtOAc ethyl acetate
Et$_2$O diethyl ether
EtOH ethanol
GMF glass microfiber filter
Grubbs II (1,3-bis(2,4,6-trimethylphenyl)-2-imidazolidinylidene)dichloro(phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexanes
HOBt or HOBT 1-hydroxybenzotriazole
H$_2$O$_2$ hydrogen peroxide
IBX 2-iodoxybenzoic acid
H$_2$SO$_4$ sulfuric acid
Jones reagent CrO$_3$ in aqueous H$_2$SO$_4$, 2 M
K$_2$CO$_3$ potassium carbonate
K$_2$HPO$_4$ potassium phosphate dibasic
KOAc potassium acetate
K$_3$PO$_4$ potassium phosphate
LAH lithium aluminum hydride
LG leaving group
LiOH lithium hydroxide
MeOH methanol
MgSO4 magnesium sulfate
MsCl methanesulfonyl chloride
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite Na₂SO₄ sodium sulfate
NBS N-bromosuccinimide
NCS N-chlorosuccinimide
NH₃ ammonia
NH₄Cl ammonium chloride
NH₄OH ammonium hydroxide
NH₄COOH ammonium formate
NMM N-methylmorpholine
OTf triflate or trifluoromethanesulfonate
Pd₂(dba)₃ tris(dibenzylideneacetone)dipalladium(O)
Pd(OAc)₂ palladium(II) acetate
Pd/C palladium on carbon
Pd(dppf)Cl₂ [1,1'-bis(diphenylphosphino)-ferrocene]dichloropalladium(II)
Ph₃PCl₂ triphenylphosphine dichloride
PG protecting group
POCl₃ phosphorus oxychloride
PPTS pyridinium p-toluenesulfonate
i-PrOH or IPA isopropanol
PS Polystyrene
PtO₂ platinum oxide
rt room temperature
RuPhos-Pd-G2 chloro(2-dicyclohexylphosphino-2',6'-diisopropoxy-1,1'-biphenyl)[2-(2'-amino-1,1'-biphenyl)]palladium(II)
SEM-Cl 2-(trimethysilyl)ethoxymethyl chloride
SiO₂ silica oxide
SnCl₂ tin(II) chloride
TBAI tetra-n-butylammonium iodide
TFA trifluoroacetic acid
THF tetrahydrofuran
TMSCHN₂ trimethylsilyldiazomethane
T3P propane phosphonic acid anhydride
TRIS tris(hydroxymethyl)aminomethane
pTSOH p-toluenesulfonic acid
TSCl p-tolunesulfonyl chloride

METHODS OF PREPARATION

The compounds of the present disclosure can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds described in this disclosure. A particularly useful compendium of synthetic methods which may be applicable to the preparation of compounds of the present disclosure may be found in Larock, R. C., Comprehensive Organic Transformations, VCH, New York (1989).

The compounds of the present disclosure may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula (I) or Formula (II) falling into a given class may be compatible with some of the reaction conditions required in some of the methods described. Such restrictions to the substituents, which are compatible with the reaction conditions, will be readily apparent to one skilled in the art and alternate methods must be used. A particularly useful compendium of synthetic methods which may be applicable to the preparation of compounds of the present disclosure may be found in Larock, R. C., *Comprehensive Organic Transformations*, VCH, New York (1989).

Generic Schemes

Compounds of the present disclosure, represented by Formula (I) and Formula (II), or any subgenera or species thereof, can be prepared according to the general routes shown in Schemes 1 to 4 below.

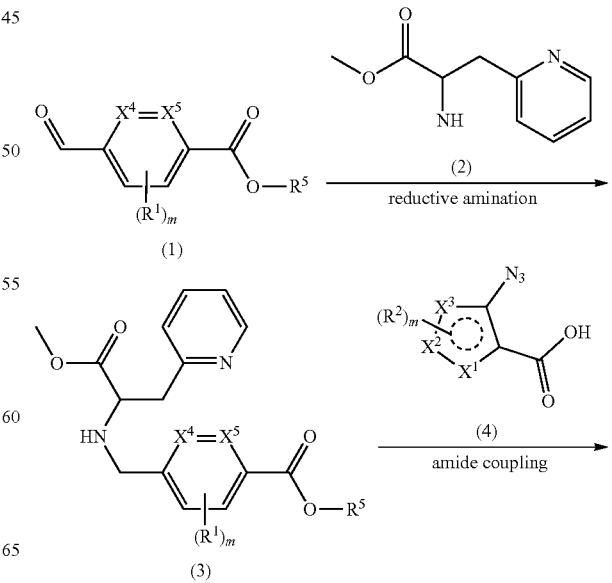

Scheme 1

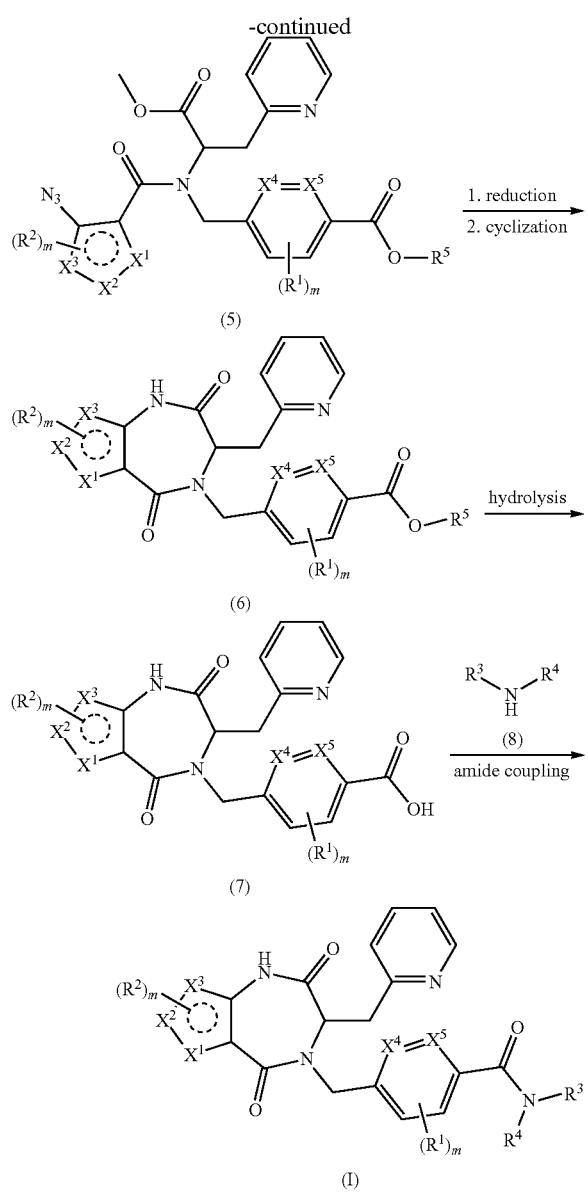

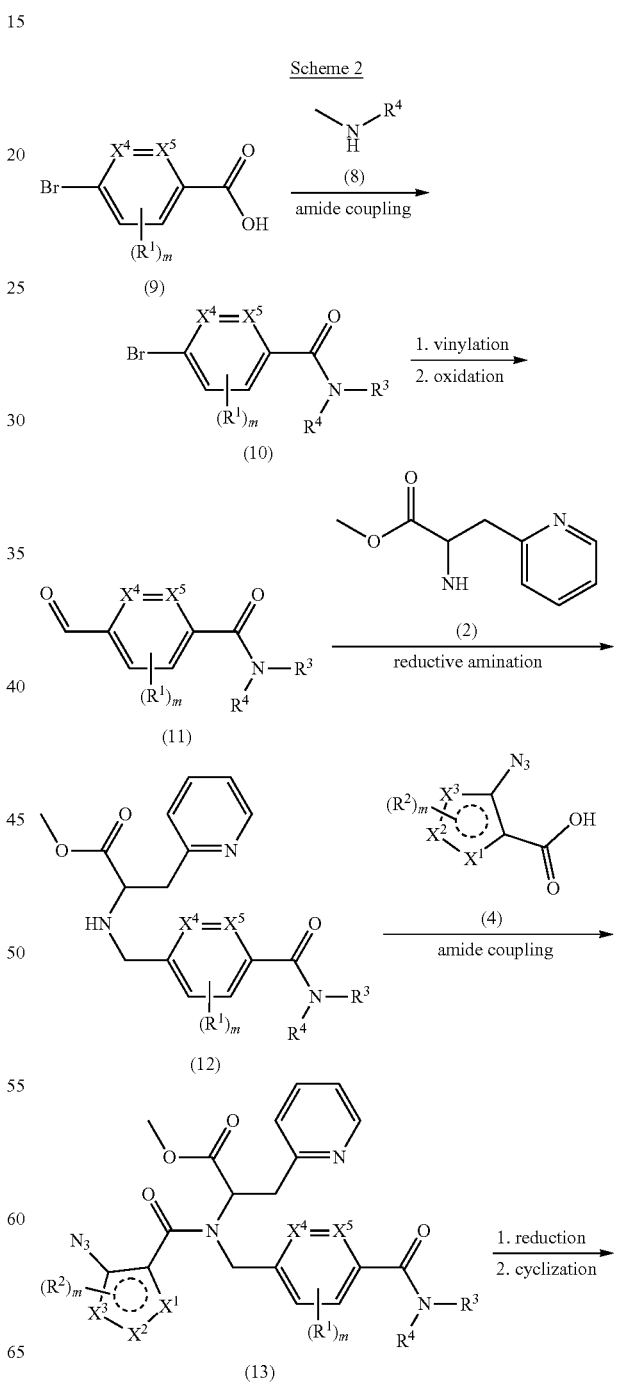

plished under acidic or basic conditions depending on the nature of $R^5$. In the case where $R^5$ is t-butyl, hydrolysis can be achieved using conditions including but not limited to dilute TFA in dichloromethane at a suitable temperature and for a time that affords the desired carboxylic acid 7. Amide coupling of amine intermediate 8 with carboxylic acid 7 can be achieved through a number of potential conditions including but not limited to utilization of a coupling reagent like HATU, or CMPU with a base such as triethylamine or Hunig's base in a solvent such as THF, dichloromethane or DMF at a suitable temperature and for a time that affords the desired amide product I.

Scheme 1 describes a method of preparing compounds of Formula I. Intermediate 1, commercially available or readily synthesized by methods known in the literature, can be joined with 2 through a reductive amination with reagents such as but not limited to sodium cyanoborohydride and acetic acid in a suitable solvent such as methanol to give intermediate 3. Amide coupling of amine intermediate 3 with carboxylic acid 4 can be achieved through a number of potential conditions including but not limited to treatment of 4 with oxalyl chloride in DCM to generate the acyl chloride that can subsequently be reacted with amine 3 in the presence of triethylamine in DCM to give amides of type 5. Staudinger reduction of 5 with an appropriate phosphine such as tributylphosphine in a solvent such as toluene gives a heteroaryl amine that can cyclize under acidic conditions including but not limited to aqueous TFA in THF to give diazepinedione 6. Hydrolysis of the ester can be accom- -continued

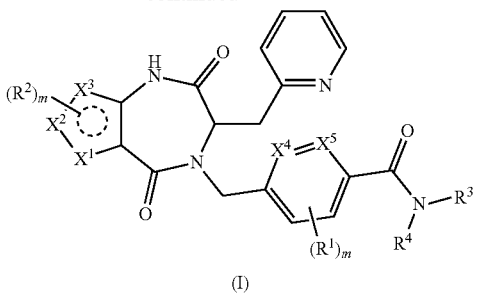

(I)

Scheme 2 describes an alternative method of preparing compounds of Formula I. Amide coupling of amine intermediate 8 with carboxylic acid 9 can be achieved through a number of potential conditions including but not limited to utilization of a coupling reagent like HATU, or CMPU with a base such as triethylamine or Hunig's base in a solvent such as THF, dichloromethane or DMF at a suitable temperature and for a time that affords the desired amide product 10. Both 8 and 9 are commercially available, readily prepared by methods known in the literature, or by one skilled in the art. Preparation of aldehyde 11 can be accomplished in a two-step process where the first step consists of vinylation of 10 by means of a metal-mediated coupling with a reagent such as tributyl(vinyl)tin in the presence of a catalyst such as but not limited to tetrakis(triphenylphosphine)palladium (0) in a solvent such as DMF. Oxidative cleavage of the resulting olefin can be accomplished through the use of reagents such as, but not limited to, $OsO_4$ and $NaIO_4$ in a mixture of THF/water or another suitable solvent system to give aldehyde intermediate 11. Intermediate 11 can be joined with intermediate 2 through a reductive amination with reagents such as but not limited to sodium cyanoborohydride and acetic acid in a suitable solvent such as methanol to give intermediate 12. Amide coupling of amine intermediate 12 with carboxylic acid 4 can be achieved through a number of potential conditions including but not limited to treatment of 4 with oxalyl chloride in DCM to generate the acyl chloride that can subsequently be reacted with amine 12 in the presence of triethylamine in DCM to give amides of type 13. Staudinger reduction of 13 with an appropriate phosphine such as tributylphosphine in a solvent such as toluene gives a heteroaryl amine that can cyclize under a variety of conditions including but not limited to basic, Lewis acidic, or acidic conditions such as aqueous TFA in THF to give the desired diazepinedione compounds I.

SCHEME 3

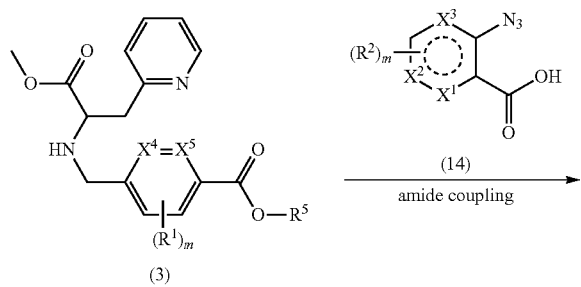

-continued

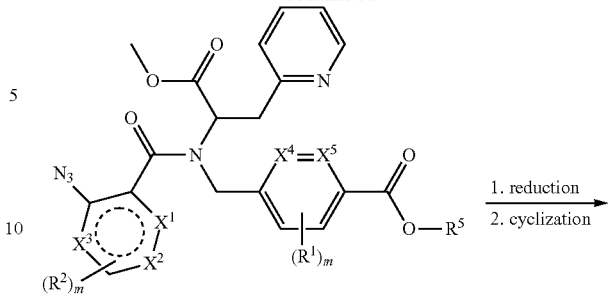

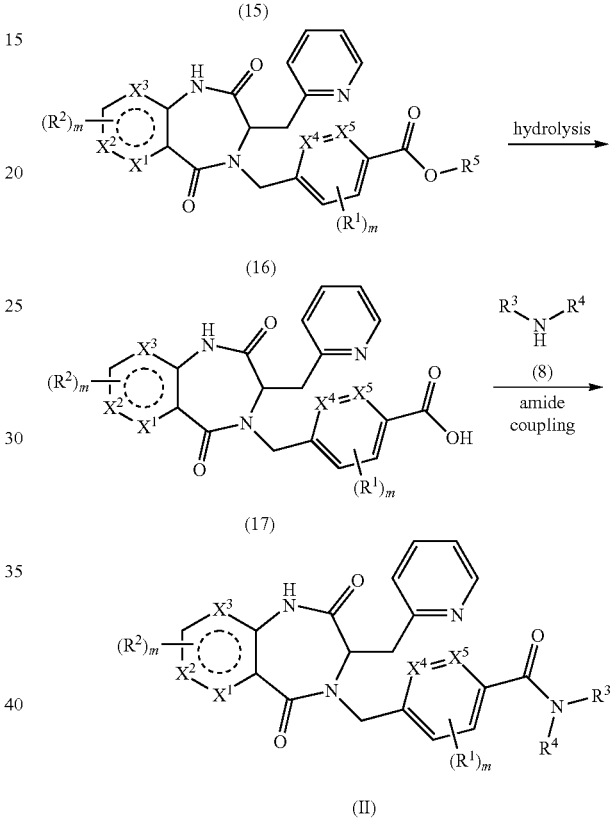

(II)

Scheme 3 describes a method of preparing compounds of Formula II. Amino compound 3 (preparation described in Scheme 1) and carboxylic acid 14, commercially available or readily prepared by one skilled in the art, can be coupled by through a number of potential conditions including but not limited to treatment of 14 with oxalyl chloride in DCM to generate the acyl chloride that can subsequently be reacted with amine 3 in the presence of triethylamine in DCM to give amides of type 15. Staudinger reduction of 15 with an appropriate phosphine such as tributylphosphine in a solvent such as toluene gives a heteroaryl amine that can cyclize under a variety of conditions including but not limited to basic, Lewis acidic, or acidic conditions such as aqueous TFA in THF to give the diazepinedione intermediate 16. Hydrolysis of the ester can be accomplished under acidic or basic conditions depending on the nature of $R^5$. In the case where $R^5$ is t-butyl, hydrolysis can be achieved using conditions including but not limited to dilute TFA in dichloromethane at a suitable temperature and for a time that affords the desired carboxylic acid 17. Amide coupling of amine intermediate 8 with carboxylic acid 17 can be achieved through a number of potential conditions, including but not limited to, utilization of a coupling reagent like HATU, or CMPU with a base such as triethylamine or Hunig's base in a solvent such as THF, dichloromethane or DMF at a suitable temperature and for a time that affords the desired amide products II.

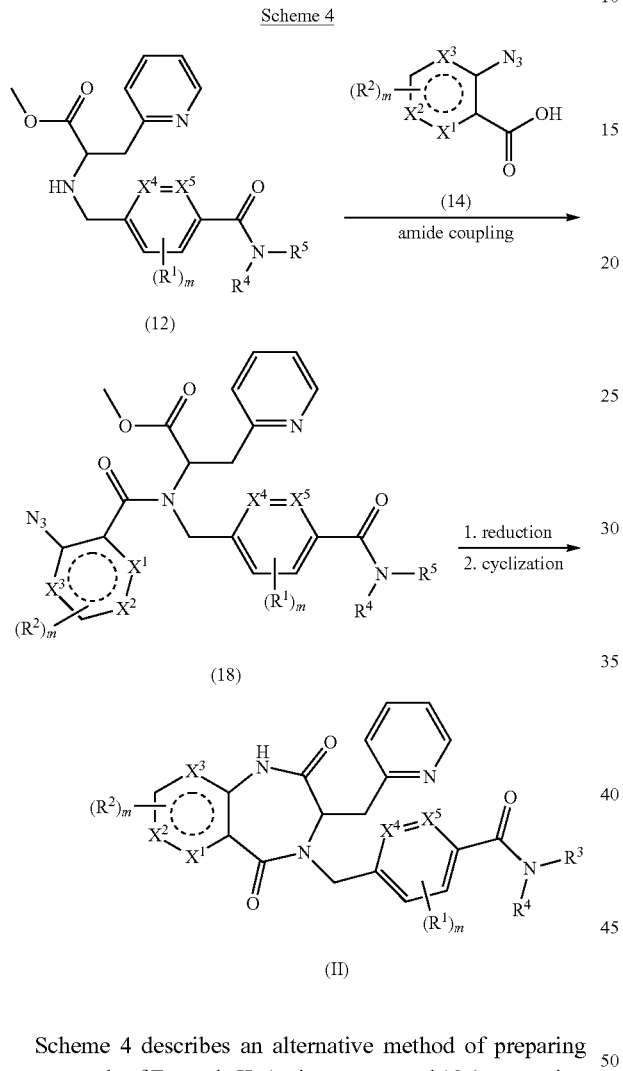

Scheme 4 describes an alternative method of preparing compounds of Formula II. Amino compound 12 (preparation described in Scheme 2) and carboxylic acid 14, commercially available or readily prepared by one skilled in the art, can be coupled by through a number of potential conditions including but not limited to treatment of 14 with oxalyl chloride in DCM to generate the acyl chloride that can subsequently be reacted with amine 12 in the presence of triethylamine in DCM to give amides of type 18. Staudinger reduction of 15 with an appropriate phosphine such as tributylphosphine in a solvent such as toluene gives a heteroaryl amine that can cyclize under a variety of conditions including but not limited to basic, Lewis acidic, or acidic conditions such as aqueous TFA in THF to give the desired diazepinedione products II.

Synthesis of Int 2

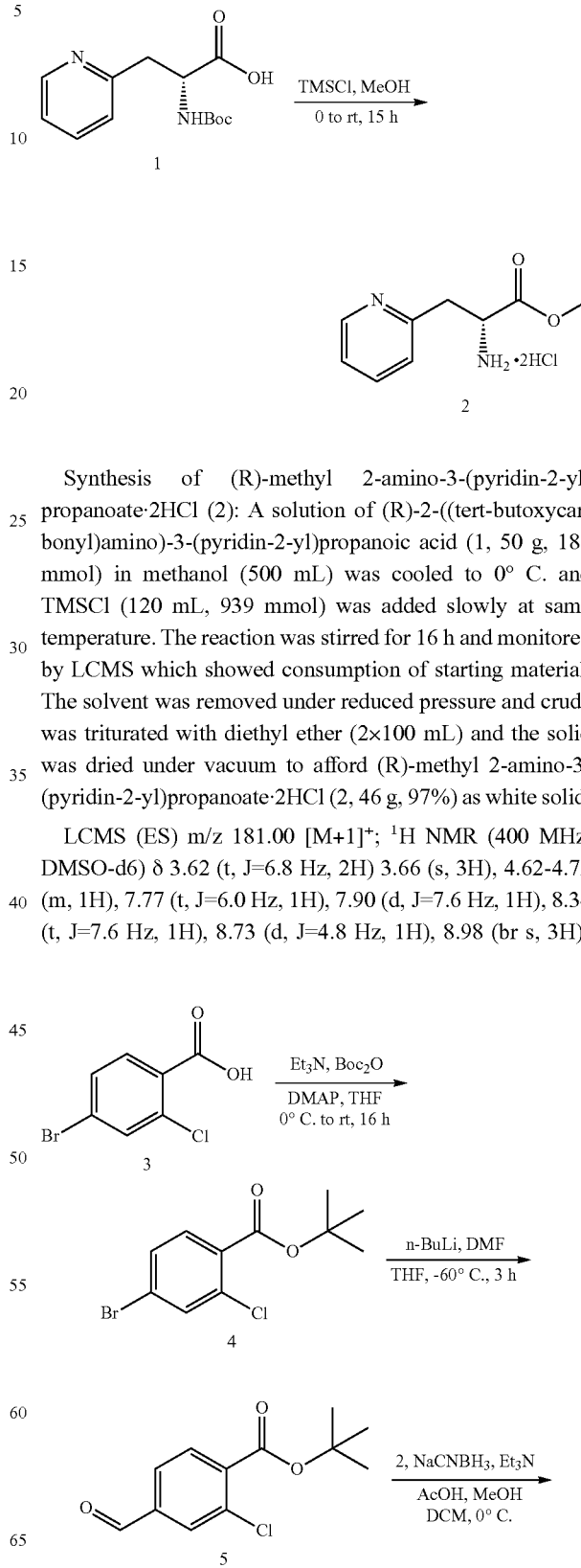

Synthesis of (R)-methyl 2-amino-3-(pyridin-2-yl) propanoate·2HCl (2): A solution of (R)-2-((tert-butoxycarbonyl)amino)-3-(pyridin-2-yl)propanoic acid (1, 50 g, 188 mmol) in methanol (500 mL) was cooled to 0° C. and TMSCl (120 mL, 939 mmol) was added slowly at same temperature. The reaction was stirred for 16 h and monitored by LCMS which showed consumption of starting material. The solvent was removed under reduced pressure and crude was triturated with diethyl ether (2×100 mL) and the solid was dried under vacuum to afford (R)-methyl 2-amino-3-(pyridin-2-yl)propanoate·2HCl (2, 46 g, 97%) as white solid.

LCMS (ES) m/z 181.00 [M+1]$^+$; $^1$H NMR (400 MHz, DMSO-d6) δ 3.62 (t, J=6.8 Hz, 2H) 3.66 (s, 3H), 4.62-4.72 (m, 1H), 7.77 (t, J=6.0 Hz, 1H), 7.90 (d, J=7.6 Hz, 1H), 8.34 (t, J=7.6 Hz, 1H), 8.73 (d, J=4.8 Hz, 1H), 8.98 (br s, 3H).

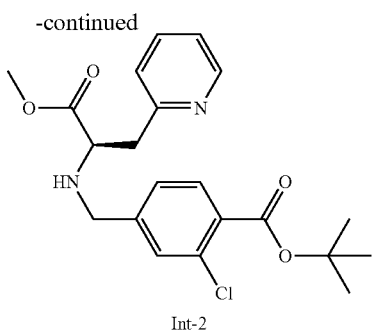

Int-2

Synthesis of tert-butyl 2-chloro-4-formylbenzoate (4): A solution of 4-bromo-2-chloro benzoic acid (3, 50 g, 212 mmol) in THF (500 mL) was cooled to 0° C. and treated with TEA (44.4 mL, 319 mmol), DMAP (7.78 g, 63.7 mmol) and reaction was stirred for 10 min. Boc$_2$O (58.5 mL, 255 mmol) was then added at the same temperature slowly (gas evolution was observed) and stirring was continued for 16 h at room temperature. The reaction was monitored by TLC and quenched with water. The reaction mixture was extracted with ethyl acetate (2×500 mL) and organic layer was separated, dried over anhydrous sodium sulfate and concentrated to afford the crude. The crude was then purified by flash silica gel column chromatography eluting the product with 2-3% ethyl acetate in hexane to afford tert-butyl 4-bromo-2-chlorobenzoate (4, 51 g, 82%) as yellow liquid. LCMS (ES): no ionization; $^1$H NMR (400 MHz, DMSO-d6) δ 1.53 (s, 9H), 7.64-7.69 (m, 2H), 7.83 (s, 1H).

Synthesis of tert-butyl 2-chloro-4-formylbenzoate (5): A solution of tert-butyl 4-bromo-2-chlorobenzoate (4, 50 g, 171 mmol) was dissolved in dry THF (500 mL) and cooled to −70° C. using dry ice acetone. A solution of DMF (16 mL, 206 mmol) in THF (66 mL) was prepared and cooled to −10° C. BuLi (82.3 mL, 206 mmol) was added portion wise (10 mL portion each) to the previous solution slowly maintaining the temperature below −65° C. and stirred the reaction mixture for 5 min followed by addition of DMF solution (8 mL). The addition was continued till complete addition of BuLi and finally excess DMF (20 mL) was added to the reaction at −65° C. The reaction was then stirred for another 30 min and then quenched with ammonium chloride solution and ethyl acetate (500 mL) was added. The organic layer was separated and aqueous layer was back extracted with ethyl acetate (2×500 mL) and combined organic layer was washed with brine, dried over anhydrous sodium sulfate and concentrated to afford crude. The crude was purified by flash silica gel column chromatography eluting the product with 3-4% ethyl acetate in hexane to afford tert-butyl 2-chloro-4-formylbenzoate (5, 20 g, 48%) as yellow liquid. LCMS (ES): no ionization; $^1$H NMR (400 MHz, DMSO-d6) δ 1.56 (s, 9H), 7.86 (d, J=8.0 Hz, 1H), 7.91 (d, J=8.0 Hz, 1H), 8.03 (s, 1H), 10.03 (s, 1H).

Synthesis of (R)-tert-butyl 2-chloro-4-(((1-methoxy-1-oxo-3-(pyridin-2-yl)propan-2-yl)amino)methyl)benzoate (Int 2): A solution of (R)-methyl 2-amino-3-(pyridin-2-yl) propanoate (2, 7.33 g, 29.1 mmol) in methanol (75 mL) was cooled to 0° C. and TEA (8.18 mL, 58.2 mmol) was added and stirred for 15 min and then tert-butyl 2-chloro-4-formylbenzoate (5, 7.0 g, 29.0 mmol) was added. The reaction was stirred for 1 h when a clear solution was obtained and then NaCNBH$_3$ (2.19 g, 34.9 mmol) was added and the reaction mixture was stirred for 15 min followed by addition of AcOH (1.33 mL, 23.3 mmol) and then reaction mixture was stirred for 25-30 min and monitored by TLC. The reaction was quenched by addition of NaHCO$_3$ solution and solvent was removed under reduced pressure. Ethyl acetate and water were added to the mixture and the organic layer was separated. The aqueous layer was back extracted with ethyl acetate (2×100 mL) and the combined organic layer was washed with brine, dried over anhydrous sodium sulfate and solvent was removed under reduced pressure to get crude. The crude was purified by flash column chromatography eluting the product with 35-40% ethyl acetate in hexane to get (R)-tert-butyl 2-chloro-4-(((1-methoxy-1-oxo-3-(pyridin-2-yl)propan-2-yl)amino)methyl)benzoate (Int 2, 5.6 g, 48%) as light yellow liquid. LCMS (ES) m/z 405.32 [M+1]$^+$; chiral HPLC purity 96:4 [CHIRALPAK IB N-5 (4.6×250) mm, 5μ, 0.1% DEA in n-Hexane/EtOH=60:40 (v/v), flow rate 1 mL/min]; $^1$H NMR (400 MHz, DMSO-d6) δ 1.53 (s, 9H), 2.82-2.92 (m, 1H), 2.95-3.10 (m, 2H), 3.57 (s, 3H), 3.60-3.67 (m, 1H), 3.76-3.86 (m, 1H), 7.16-7.22 (m, 4H), 7.56 (d, J=8.0 Hz, 1H), 7.69 (t, J=7.6 Hz, 1H), 8.45 (s, 1H). Note: Racemization was observed if the reaction was stirred for more than 30 min after addition of acetic acid.

Example 1

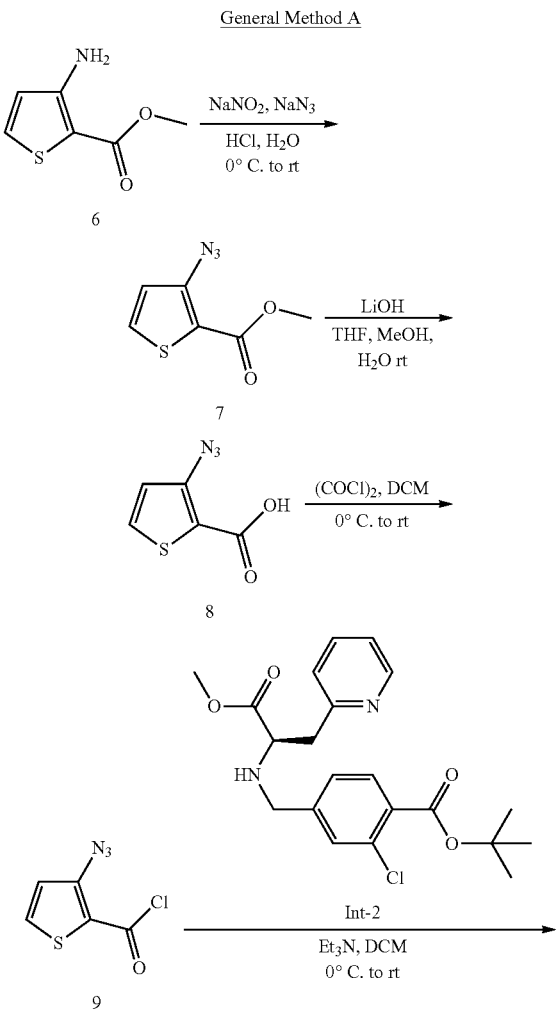

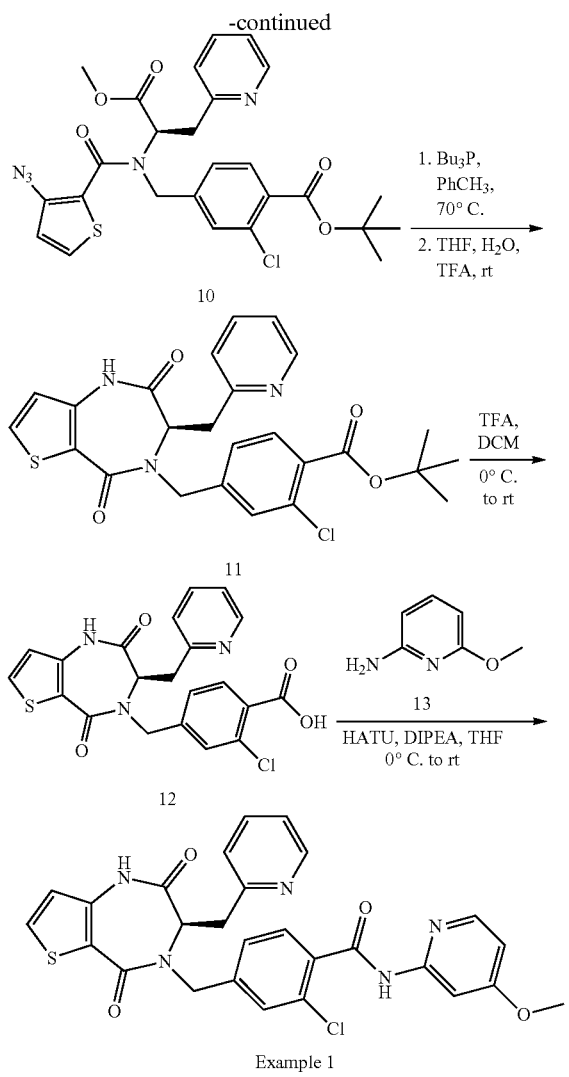

Example 1

Synthesis of methyl 3-azidothiophene-2-carboxylate (7): To a solution of methyl 3-aminothiophene-2-carboxylate (6, 10.0 g, 63.6 mmol) in HCl (50 mL) and water (50 mL) at 0° C., NaNO₂ (6.58 g, 95.4 mmol) was added and the mixture was stirred for 30 min. The mixture was filtered to remove the solid and the mother liquor was cooled to 0° C. followed by addition of NaN₃ (5.0 g, 76.3 mmol) at 0° C. The mixture was stirred for 30 min and the precipitated solid was filtered. The solid was then dissolved in ethyl acetate, dried over anhydrous sodium sulfate, filtered and concentrated to get solid which was triturated with pentane and dried under vacuum to afford methyl 3-azidothiophene-2-carboxylate (7, 9.5 g, 81%) as off white solid.

$^1$H NMR (400 MHz, DMSO-d6) δ 3.78 (s, 3H), 7.15 (d, J=5.6 Hz, 1H), 7.93 (d, J=5.6 Hz, 1H).

Synthesis of 3-azidothiophene-2-carboxylic acid (8): To a solution of methyl 3-azidothiophene-2-carboxylate (7, 9.0 g, 49.1 mmol) in THF (45 mL) and methanol (45 mL), a solution of LiOH·H2O (6.18 g, 147 mmol) in water (10 mL) was added at room temperature. The reaction mixture was stirred for 16 h when TLC showed consumption of starting material, the solvent was removed under reduced pressure and then water (5 mL) was added followed by addition of HCl to bring the pH~2-3. The precipitated solid was then filtered and the solid was again dissolved in ethyl acetate, dried over anhydrous sodium sulfate and concentrated to get solid which was triturated with pentane and dried under vacuum to afford 3-azidothiophene-2-carboxylic acid (8, 8.0 g, 96%) as white solid. Note: The solid should be dried properly to remove water before going for the next step. $^1$H NMR (400 MHz, DMSO-d6) δ 7.07 (d, J=5.2 Hz, 1H), 7.85 (d, J=5.6 Hz, 1H), 13.24 (br s, 1H).

Synthesis of 3-azidothiophene-2-carbonyl chloride (9): To a mixture of 3-azidothiophene-2-carboxylic acid (8, 4.0 g, 23.6 mmol) in dichloromethane (40 mL), oxalyl chloride (3.0 mL, 35.5 mmol) was added at 0° C. followed by addition of two drops of dimethylformamide. The reaction mixture was then stirred at room temperature for 2 h when TLC showed consumption of starting material. The volatiles were removed under reduced pressure and crude was dried under high vacuum to afford 3-azidothiophene-2-carbonyl chloride (9, 4.0 g, 90%) as reddish-brown solid which was used directly for the next step.

Synthesis of (R)-tert-butyl 4-((3-azido-N-(1-methoxy-1-oxo-3-(pyridin-2-yl)propan-2-yl)thiophene-2-carboxamido)methyl)-2-chlorobenzoate (10): A solution of Int 2 (4.0 g, 9.88 mmol) in dichloromethane (40 mL) was cooled to 0° C. and DIPEA (2.60 mL, 14.8 mmol) was added and the mixture was stirred for 10 min. A solution of 3-azidothiophene-2-carbonyl chloride (9, 2.22 g, 11.9 mmol) in dichloromethane (10 mL) was added slowly at same temperature. The reaction was monitored by TLC which showed consumption of starting material after 45 min. The reaction was quenched by addition of water (50 mL) and extracted with dichloromethane (3×100 mL). The organic layer was dried over anhydrous sodium sulfate and solvent was removed under reduced pressure to get the crude. The crude was then purified by flash silica gel column chromatography using 40-50% ethyl acetate in hexane. The fraction containing product was concentrated to get solid which was triturated with pentane and dried under vacuum to afford (R)-tert-butyl 4-((3-azido-N-(1-methoxy-1-oxo-3-(pyridin-2-yl)propan-2-yl)thiophene-2-carboxamido)methyl)-2-chlorobenzoate (10, 5.0 g, 91%) as yellowish liquid. LCMS (ES) m/z 556.38 [M+1]$^+$; $^1$H NMR (400 MHz, DMSO-d6) δ 1.56 (s, 9H), 3.32-3.50 (m, 2H), 3.63 (s, 3H), 4.30-5.50 (m, 3H), 7.00-7.33 (m, 4H), 7.39 (s, 1H), 7.57 (d, J=8.0 Hz, 1H), 7.67 (br s, 1H), 7.76 (br s, 1H), 8.42 (br s, 1H).

Synthesis of (R)-tert-butyl 2-chloro-4-((2,5-dioxo-3-(pyridin-2-ylmethyl)-2,3-dihydro-1H-thieno[3,2-e][1,4]diazepin-4(5H)-yl)methyl)benzoate (11): To a solution of (R)-tert-butyl 4-((3-azido-N-(1-methoxy-1-oxo-3-(pyridin-2-yl)propan-2-yl)thiophene-2-carboxamido)methyl)-2-chlorobenzoate (10, 5.0 g, 8.9 mmol) in toluene (50 ml) at room temperature, tributylphosphene (2.66 g, 10.7 mmol) was added and the mixture was stirred at 70° C. for 16 h. After consumption of starting material as confirmed by TLC, the solvent was removed under reduced pressure to get crude. The crude was then dissolved in THF (50 mL), water (5 mL) and was treated with TFA (5 mL) at room temperature. The mixture was stirred for 12 h and then quenched with water and extracted with ethyl acetate. The combined organic layer was dried over anhydrous sodium sulfate and solvent was removed under reduced pressure to get the crude. The crude was purified by flash silica gel column chromatography eluting the product with 80-90% ethyl acetate in hexane to afford (R)-tert-butyl 2-chloro-4-((2,5-dioxo-3-(pyridin-2-ylmethyl)-2,3-dihydro-1H-thieno[3,2-e][1,4]diazepin-4(5H)-yl)methyl)benzoate (11, 4.0 g, 89%) as off white solid. LCMS (ES) m/z 498.26 [M+1]$^+$ $^1$H NMR (400 MHz, DMSO-d6) δ 1.53 (s, 9H), 2.90-3.12 and 3.40-3.50 (m, 2H), 3.80-5.20 (m, 3H), 6.80-6.90 (m, 1H), 7.00-7.30 (m, 3H), 7.34 (s, 1H), 7.61 (d, J=7.6 Hz, 1H), 7.67 (t, J=7.2 Hz, 1H), 7.89 (d, J=5.2 Hz, 1H), 8.43 (br s, 1H), 11.12 (br s, 1H).

Synthesis of (R)-2-chloro-4-((2,5-dioxo-3-(pyridin-2-ylmethyl)-2,3-dihydro-1H-thieno[3,2-e][1,4]diazepin-4(5H)-yl)methyl)benzoic acid (12): A solution of (R)-tert-butyl 2-chloro-4-((2,5-dioxo-3-(pyridin-2-ylmethyl)-2,3-dihydro-1H-thieno[3,2-e][1,4]diazepin-4(5H)-yl)methyl)benzoate (11, 4.0 g, 8.03 mmol) in dichloromethane (40 mL) was cooled to 0° C. followed by addition of TFA (4 mL). The reaction was then stirred for 2 h when TLC showed consumption of starting material. The solvent was then removed under reduced pressure and triturated with diethyl ether (2×25 mL) to afford (R)-2-chloro-4-((2,5-dioxo-3-(pyridin-2-ylmethyl)-2,3-dihydro-1H-thieno[3,2-e][1,4]diazepin-4(5H)-yl)methyl)benzoic acid TFA salt (12, 4.0 g 100%) as off white solid.

LCMS (ES) m/z 441.92 [M+1]$^+$ chiral HPLC purity 96:4 [ChiralPak IG (4.6×250) mm, 5μ Mobile Phase: CO2/0.2% TEA in MeOH (60:40), flow rate 3 mL/min].

$^1$H NMR (400 MHz, DMSO-d6) δ 3.00-3.20 and 3.50-3.70 (m, 2H), 4.10-5.15 (m, 3H), 6.80-6.90 (br s, 1H), 7.20-7.65 (m, 4H), 7.70 (d, J=8.0 Hz, 1H), 7.90 (d, J=5.2 Hz, 1H), 7.93-8.05 (m, 1H), 8.54 (d, J=4.8 Hz, 1H), 11.18 (br s, 1H), 13.20 (br s, 1H).

Synthesis of (R)-2-chloro-4-((2,5-dioxo-3-(pyridin-2-ylmethyl)-2,3-dihydro-1H-thieno[3,2-e][1,4]diazepin-4(5H)-yl)methyl)-N-(4-methoxypyridin-2-yl)benzamide (Example 1): A solution of (R)-2-chloro-4-((2,5-dioxo-3-(pyridin-2-ylmethyl)-2,3-dihydro-1H-thieno[3,2-e][1,4]diazepin-4(5H)-yl)methyl)benzoic acid·TFA salt (12, 2.9 g, 6.56 mmol) in THF (30 mL) was stirred for 10 min and then cooled to 0° C. and treated with DIPEA (3.5 mL, 19.68 mmol) and stirred for 15 min when a clear solution was observed. HATU (3.74 g, 9.84 mmol) was then added to the above reaction at 0° C. and cooling was removed after 10 min. The mixture was stirred for 15 min at room temperature and a solution of 4-methoxy-2-aminopyridine (13, 0.98 g, 7.87 mmol) dissolved in THF (5 mL) was added and the reaction mixture was stirred at 70° C. for 16 h. After completion of the reaction as monitored by TLC and LCMS, reaction mixture was cooled to room temperature and water was added followed by addition of ethyl acetate (100 mL). The organic layer was separated and aqueous layer was back extracted with ethyl acetate (2×100 mL). The combined organic layer was washed with brine and dried over anhydrous sodium sulfate. The solvent was removed under reduced pressure and the crude was purified by flash silica gel column chromatography using 2-3% methanol in dichloromethane as eluent to afford (R)-2-chloro-4-((2,5-dioxo-3-(pyridin-2-ylmethyl)-2,3-dihydro-1H-thieno[3,2-e][1,4]diazepin-4(5H)-yl)methyl)-N-(4-methoxypyridin-2-yl)benzamide (Example 1, 2.6 g, 36%) as white solid. Two reactions on 2.9 g scale were done and compound was purified by combining both the batches to afford the above yield.

LCMS (ES) m/z 548.15 [M+1]$^+$ (Purity 98.37%); chiral HPLC purity 97.5:2.5 [CHIRALPAK IB N-5 (4.6×250) mm, 5μ, CO2/0.2% TEA in MeOH (60:40), flow rate 3 mL/min].

$^1$H NMR (400 MHz, DMSO-d6) δ 2.90-3.15 and 3.50-3.65 (m, 2H), 3.84 (s, 3H), 4.10-5.20 (m, 3H), 6.75 (dd, J=5.6 and 2.0 Hz, 1H), 6.86 (d, J=4.4 Hz, 1H), 7.05-7.30 (m, 3H), 7.35 (s, 1H), 7.47 (d, J=8.0 Hz, 1H), 7.70 (t, J=7.2 Hz, 1H), 7.79 (s, 1H), 7.89 (d, J=5.2 Hz, 1H), 8.13 (d, J=5.6 Hz, 1H), 8.46 (br s, 1H), 10.92 (s, 1H), 11.14 (br s, 1H).

Note: 1. 2-3 purifications are required to get pure product.
2. The HATU complex of acid is very stable and remains in the reaction if the amine is less reactive. Temperature may be increased to 75-80° C. if complex remains.

Synthesis of Int 6

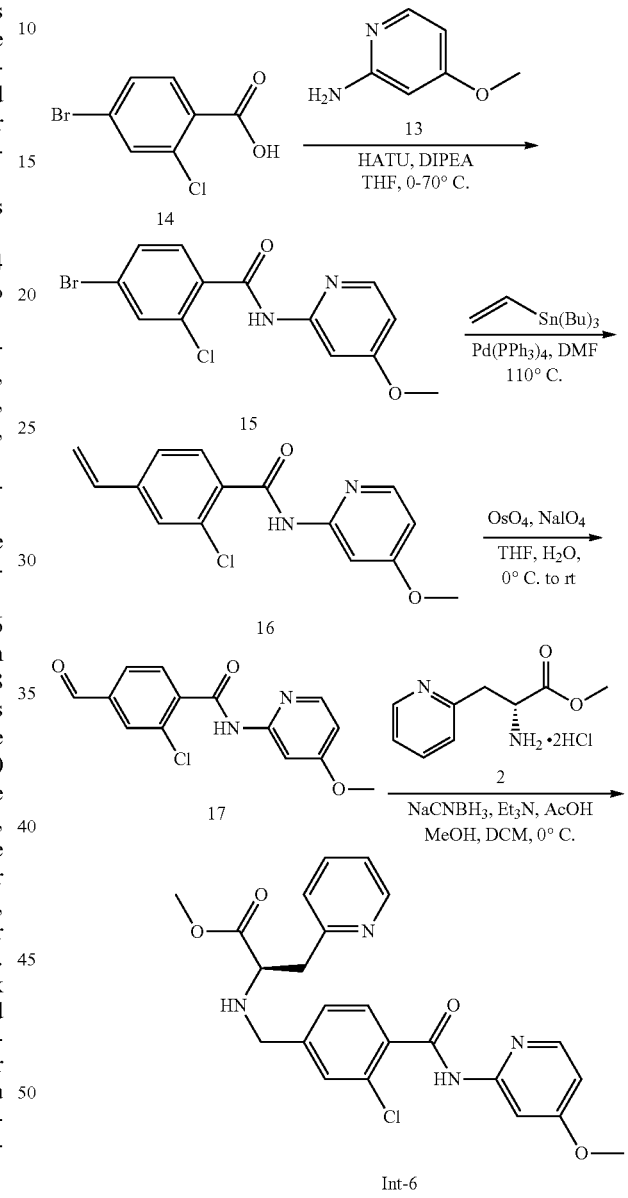

Synthesis of 4-bromo-2-chloro-N-(4-methoxypyridin-2-yl)benzamide (15): To a solution of 4-bromo-2-chlorobenzoic acid (14, 30 g, 127 mmol) in THF (300 mL), DIPEA (49.4 g, 382 mmol) was added followed by addition of HATU (72.7 g, 191 mmol) at 0° C. The reaction mixture was stirred for 15 min and then 2-amino-4-methoxy pyridine (13, 23.7 g, 191 mmol) was added and the reaction mixture was heated at 75° C. for 16 h. After completion as monitored by TLC, the reaction was quenched with ice and stirred for 15 min. The precipitated solid was filtered and washed with water followed by dissolving the solid in ethyl acetate and drying over anhydrous sodium sulfate. The solvent was removed under reduced pressure and the crude was triturated with pentane to afford 4-bromo-2-chloro-N-(4-methoxypyridin-2-yl)benzamide (15, 40.0 g, 92%) as off white solid.

LCMS (ES) m/z 341.16 [M+1]$^+$ $^1$H NMR (400 MHz, DMSO-d6) δ 3.85 (s, 3H), 6.78 (dd, J=5.6 and 2.4 Hz, 1H), 7.50 (d, J=8.4 Hz, 1H), 7.63 (dd, J=8.0 and 1.6 Hz, 1H), 7.79 (s, 1H), 7.83 (d, J=1.6 Hz, 1H), 8.15 (d, J=5.6 Hz, 1H), 11.02 (s, 1H).

Synthesis of 2-chloro-N-(4-methoxypyridin-2-yl)-4-vinylbenzamide (16): A solution of 4-bromo-2-chloro-N-(4-methoxypyridin-2-yl)benzamide (15, 38 g, 111 mmol) in DMF (200 mL) was treated with tributyl(vinyl)tin (38.8 g, 122 mmol) and mixture was degassed with argon for 10 min followed by addition of tetrakis(triphenylphosphine)palladium (0) (6.43 g, 5.56 mmol). The reaction was degassed for another 5 min with argon and then heated at 110° C. for 16 h. The reaction was monitored by TLC which showed completion of starting material, the reaction was cooled to room temperature and ethyl acetate was added. The solids were filtered over a bed of celite and the celite bed was washed with ethyl acetate and organic layer was separated and washed with water, brine, dried over anhydrous sodium sulfate and solvent was removed under reduced pressure to afford crude which was purified by silica gel column chromatography eluting the product with 20-25% ethyl acetate in hexane. The solvent was removed under reduced pressure to afford 2-chloro-N-(4-methoxypyridin-2-yl)-4-vinylbenzamide (16, 20 g, 62%) as white solid.

LCMS (ES) m/z 288.96 [M+1]$^+$ $^1$H NMR (400 MHz, DMSO-d6) δ 3.85 (s, 3H), 5.40 (d, J=10.8 Hz, 1H), 6.04 (d, J=17.6 Hz, 1H), 6.73-6.83 (m, 2H), 7.52 (s, 2H), 7.65 (s, 1H), 7.81 (s, 1H), 8.15 (d, J=5.6 Hz, 1H), 10.95 (s, 1H).

Synthesis of 2-chloro-4-formyl-N-(4-methoxypyridin-2-yl)benzamide (17): To a solution of 2-chloro-N-(4-methoxypyridin-2-yl)-4-vinylbenzamide (16, 20 g, 69.3 mmol) in THF (50 mL) and water (50 mL) at 0° C., OsO$_4$ (25 mL, 4% solution in water) was added and the reaction mixture was then stirred for 2 h. To the above reaction NaIO$_4$ (44.4 g, 208 mmol) was added slowly and the reaction was stirred for 16 h at room temperature. The reaction was monitored by TLC and LCMS which showed consumption of starting material, the reaction mixture was diluted with water (100 mL) and ethyl acetate (500 ml). The aqueous layer was back extracted with ethyl acetate (2×200 mL) and combined organic layer was washed with brine and dried over sodium sulfate. The solvent was removed under reduced pressure to get the crude. The crude was purified by silica gel column chromatography eluting the product with 40-45% ethyl acetate in hexane to get solid which was triturated with diethyl ether to remove non polar impurities (if any) and the solid was dried under high vacuum to afford 2-chloro-4-formyl-N-(4-methoxypyridin-2-yl)benzamide (17, 12.1 g, 60%) as yellow solid.

LCMS (ES) m/z 290.76 [M+1]$^+$ $^1$H NMR (400 MHz, DMSO-d6) δ 3.86 (s, 3H), 6.79 (d, J=4.0 Hz, 1H), 7.76 (d, J=8.0 Hz, 1H), 7.82 (s, 1H), 7.92 (d, J=8.0 Hz, 1H), 8.03 (s, 1H), 8.16 (d, J=5.6 Hz, 1H), 10.04 (s, 1H), 11.18 (s, 1H).

Synthesis of (R)-methyl 2-((3-chloro-4-((4-methoxypyridin-2-yl)carbamoyl)benzyl)amino)-3-(pyridin-2-yl)propanoate (Int 6): (R)-Methyl 2-amino-3-(pyridin-2-yl)propanoate·2HCl (2, 3.72 g, 20.6 mmol) was dissolved in methanol (70 mL), dichloromethane (30 mL) and triethylamine (7.5 mL) was added at 0° C. The mixture was stirred for 15 min and then 2-chloro-4-formyl-N-(4-methoxypyridin-2-yl)benzamide (17, 5.0 g, 17.2 mmol) was added and the reaction was stirred for 45 min. To the above reaction NaCNBH$_3$ (1.62 g, 25.7 mmol) was added in portions in 5 min and stirred the mixture for 10 min followed by addition of acetic acid (1.0 g, 17.2 mmol).

The reaction was then stirred for 30 min when TLC showed consumption of most of the starting material, the reaction was quenched with NaHCO$_3$ solution and water. The methanol was removed under reduced pressure and the mixture was then extracted with ethyl acetate (2×200 mL) and organic layer was washed with brine, dried over anhydrous sodium sulfate and solvent was removed under reduced pressure to get crude. The crude was then purified by silica gel column chromatography eluting the product with 80-90% ethyl acetate in hexane to afford (R)-methyl 2-((3-chloro-4-((4-methoxypyridin-2-yl)carbamoyl)benzyl) amino)-3-(pyridin-2-yl)propanoate (Int 6, 4.0 g, 51%) as yellow liquid.

LCMS (ES) m/z 455.23 [M+1]$^+$; chiral HPLC purity 99.5:0.5 [Lux_Cellulose-2 (4.6×250) mm, 5μ, CO2/0.2% TEA in MeOH (60:40), flow rate 3 mL/min].

$^1$H NMR (400 MHz, DMSO-d6) δ 2.80-2.90 (m, 1H), 2.96-3.10 (m, 2H), 3.59 (s, 3H), 3.60-3.68 (m, 2H), 3.80-3.83 (m, 1H), 3.84 (s, 3H), 6.76 (dd, J=5.6 and 2.4 Hz, 1H), 7.17 (d, J=8.0 Hz, 1H), 7.20-7.30 (m, 3H), 7.40 (d, J=7.6 Hz, 1H), 7.70 (t, J=7.6 Hz, 1H), 7.80 (s, 1H), 8.16 (d, J=6.0 Hz, 1H), 10.89 (s, 1H).

Example 2

General Method B

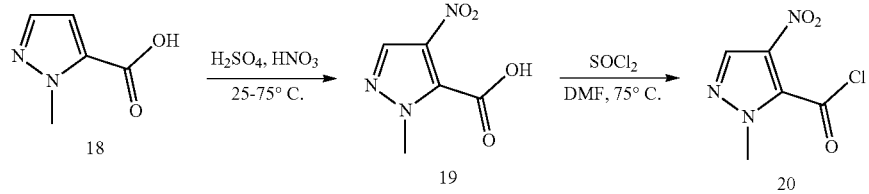

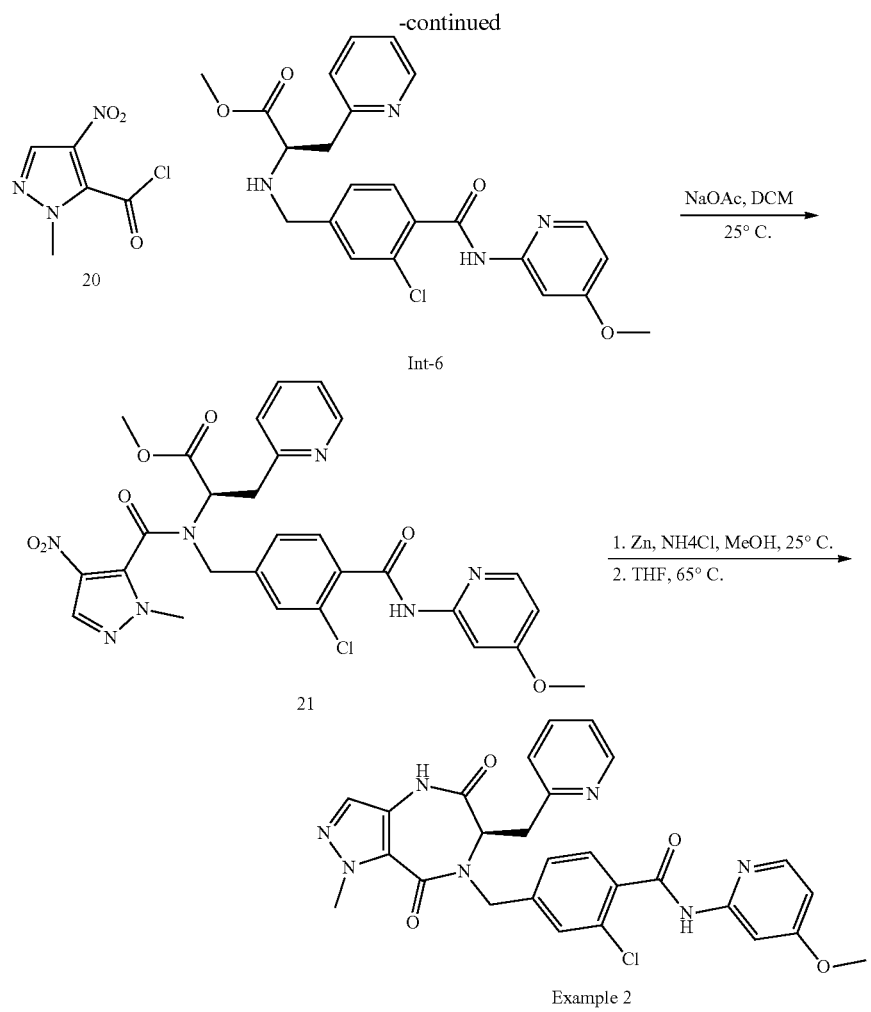

Example 2

Synthesis of 1-methyl-4-nitro-1H-pyrazole-5-carboxylic acid (19): To a solution of HNO$_3$ (55 g, 873 mmol, 1.10 eq) and H$_2$SO$_4$ (460 g, 4.60 mol, 250 mL, 98% purity, 5.80 eq) was added compound 1 (100 g, 793 mmol, 1 eq) in portions at 25° C. The resulting solution was stirred at 35° C. for 1 h. Then the reaction was heated to 75° C. and stirred at 75° C. for 2 hrs. TLC showed the starting material was consumed completely. The reaction was cooled to 25° C. and poured into ice water (1.0 L). The resulting suspension was filtered and the filter cake was rinsed with water (400 mL). The filter cake was dried under vacuum to give 1-methyl-4-nitro-1H-pyrazole-5-carboxylic acid (19, 90 g, 526 mmol, 66.3% yield) as white solid.

$^1$H NMR (400 MHz, DMSO-d6) δ 3.95 (s, 3H), 8.29 (s, 1H).

Synthesis of 1-methyl-4-nitro-1H-pyrazole-5-carbonyl chloride (20): A solution of 1-methyl-4-nitro-1H-pyrazole-5-carboxylic acid (19, 80 g, 468 mmol, 1 eq) and DMF (342 mg, 4.68 mmol, 360 uL, 0.01 eq) in SOCl$_2$ (656 g, 5.51 mol, 400 mL, 11.8 eq) was stirred at 75° C. for 12 hrs. A sample was taken (quenched by MeOH), and TLC (petroleum ether:ethyl acetate=0:1, R$_f$ of 19 was 0.3, R$_f$ of compound 20 was 1.0) showed the starting material was consumed completely. The reaction was concentrated under vacuum to give 1-methyl-4-nitro-1H-pyrazole-5-carbonyl chloride (20, 89 g, crude) as brown oil, which was used directly in the next step.

Synthesis of methyl (R)-2-(N-(3-chloro-4-((4-methoxypyridin-2-yl)carbamoyl)benzyl)-1-methyl-4-nitro-1H-pyrazole-5-carboxamido)-3-(pyridin-2-yl)propanoate (21): To a solution of Int-6 (224 g, 493 mmol, 1.05 eq) and NaOAc (116 g, 1.41 mol, 3 eq) in DCM (1.5 L) was dropwise added a solution of 1-methyl-4-nitro-1H-pyrazole-5-carbonyl chloride (20, 89 g, 470 mmol, 1 eq) in DCM (200 mL) at 25° C. The resulting solution was stirred at 25° C. for 1 h. LCMS showed the starting material was consumed completely. The reaction was poured into water (1.2 L). The organic phase was collected and the aqueous phase was extracted with DCM (400 mL×2). The combined organic phase was washed with water (2 L), dried over anhydrous Na$_2$SO$_4$ and concentrated under vacuum to give the crude product. The crude product was dissolved in EtOAc (1.5 L) at 25° C. The resulting solution was stirred at 10° C. for 5 hrs and a brown suspension was obtained. The suspension was filtered and the filter cake was rinsed with EtOAc (200 mL). The filter cake was dried under vacuum to afford methyl (R)-2-(N-(3-chloro-4-((4-methoxypyridin-2-yl)carbamoyl)benzyl)-1-methyl-4-nitro-1H-pyrazole-5-carboxamido)-3-(pyridin-2-yl)propanoate (21, 180 g, 296 mmol, 63.1% yield) as an off-white solid.

LCMS (ES) m z 608.3 [M+H]$^+$.

Synthesis of (R)-2-chloro-N-(4-methoxypyridin-2-yl)-4-(((1-methyl-5,8-dioxo-6-(pyridin-2-ylmethyl)-4,5,6,8-tetrahydropyrazolo[4,3-e][1,4]diazepin-7(1H)-yl)methyl)benzamide (Example 2): To a solution of methyl (R)-2-(N-(3-chloro-4-((4-methoxypyridin-2-yl)carbamoyl)benzyl)-1-methyl-4-nitro-1H-pyrazole-5-carboxamido)-3-(pyridin-2-yl)propanoate (21, 180 g, 296 mmol, 1 eq) and NH$_4$Cl (127 g, 2.37 mol, 8 eq) in MeOH (1 L) and H$_2$O (250 mL) was added Zn (96.8 g, 1.48 mol, 5 eq) in portions at 25° C. The resulting suspension was stirred at 25° C. for 3 hrs. LCMS showed the starting material was consumed completely. The reaction was filtered through celite. The filter cake was rinsed with THF (500 mL). The filtrate was concentrated under vacuum to give a yellow solid (170 g, crude).

A solution of the crude yellow solid (170 g, 294 mmol, 1 eq) in THF (1 L) was stirred at 65° C. for 12 hrs. TLC (dichloromethane:methanol=10:1, R$_f$ of crude intermediate was 0.5, R$_f$ of Example 2 was 0.75) showed the starting material was consumed completely. The reaction was cooled to 25° C. and filtered through celite. The filter cake was rinsed with THF (300 mL). The filtrate was concentrated under vacuum to give the product as yellow solid. The crude product was dissolved in ACN (400 mL). The resulting solution was poured into water (5 L) with stirring. The resulting suspension was filtered and the filter cake was rinsed with water (500 mL). The filter cake was dried under vacuum to give (R)-2-chloro-N-(4-methoxypyridin-2-yl)-4-((1-methyl-5,8-dioxo-6-(pyridin-2-ylmethyl)-4,5,6,8-tetrahydropyrazolo[4,3-e][1,4]diazepin-7(1H)-yl)methyl)benzamide (Example 2, 135 g, 247 mmol, 71.5% yield) as light yellow solid. LCMS (ES) m/z 546.20 [M+1]$^+$; (Purity 96.80%); Chiral HPLC purity >99% [Lux Amylose-1 (4.6× 250) mm, 5μ, Mobile Phase: CO$_2$/0.2% TEA in MeOH (60:40), flow rate 3 mL/min].

$^1$H NMR (400 MHz, DMSO-d6) δ 2.85-3.25 and 3.56-3.68 (m, 2H), 3.84 (s, 3H), 4.04 and 4.06 (2×s, 3H), 4.60-5.15 (m, 3H), 6.76 (dd, J=5.6 and 2.0 Hz, 1H), 7.15-7.35 (m, 5H), 7.43-7.50 (m, 1H), 7.65-7.73 (m, 1H), 7.78 (s, 1H), 8.14 (d, J=6.0 Hz, 1H), 8.38 and 8.48 (m, 1H), 10.49 and 10.66 (2×s, 1H), 10.93 (s, 1H).

Example 3

General Method C

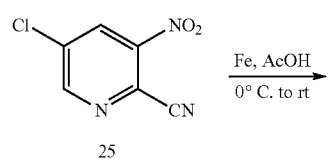

25

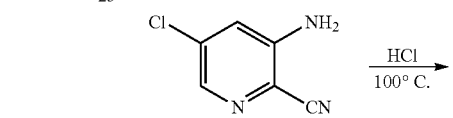

26

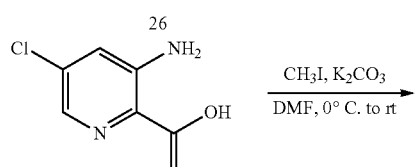

27

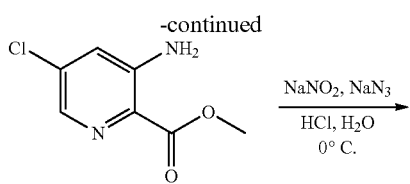

28

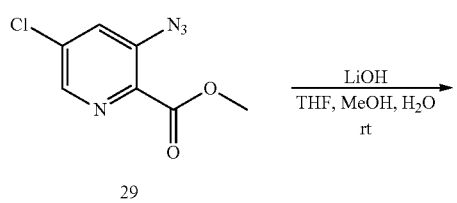

29

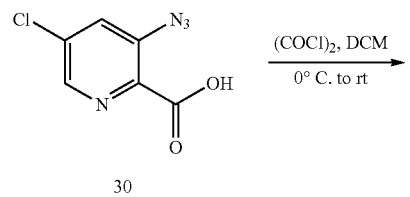

30

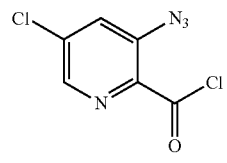

31

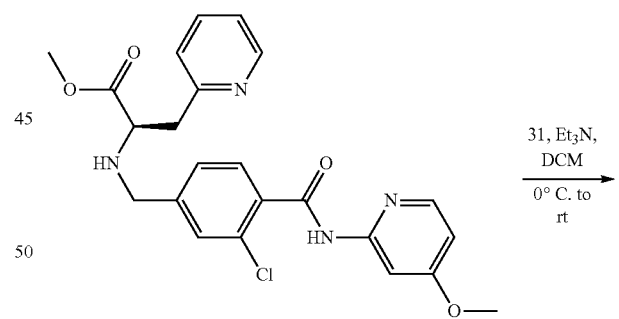

Int-6

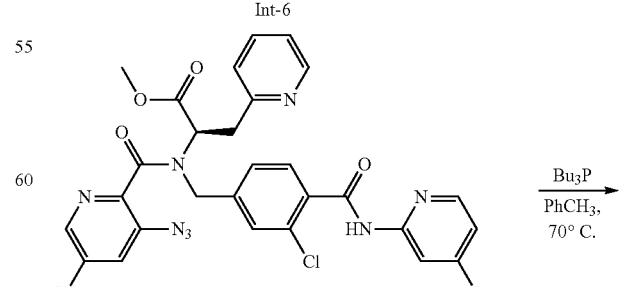

32

-continued
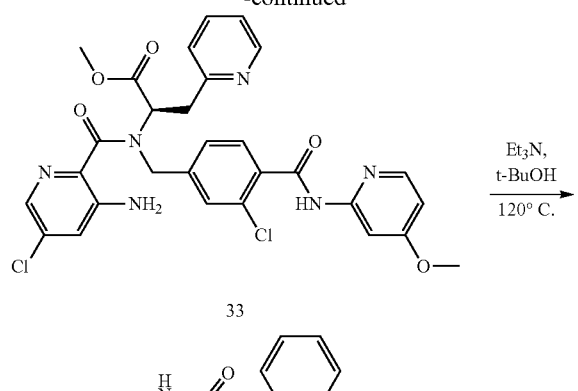
33
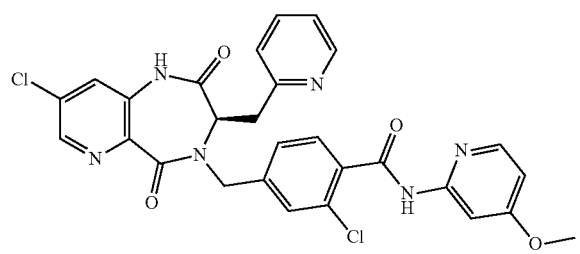
Example 3
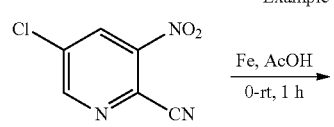
22
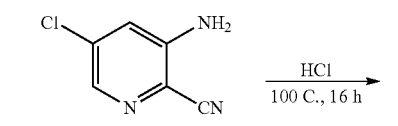
23
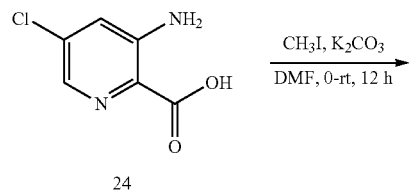
24
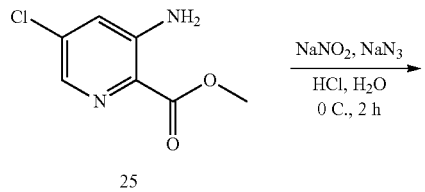
25
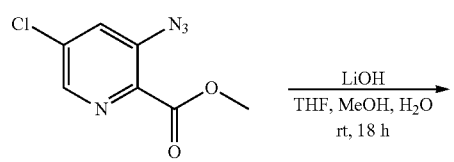
26
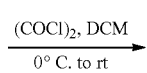
27
-continued
28
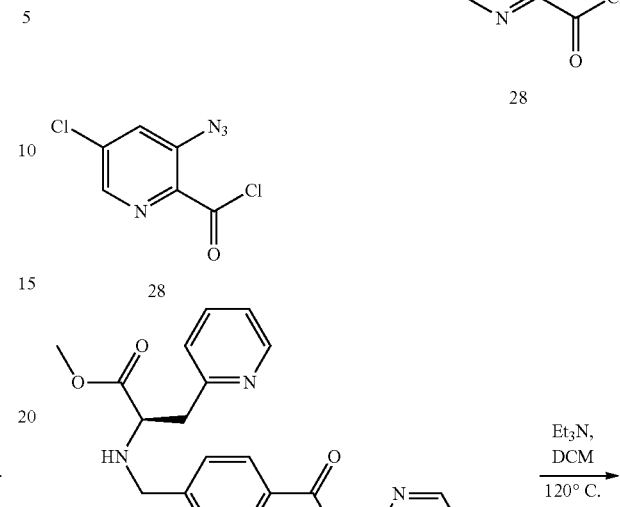
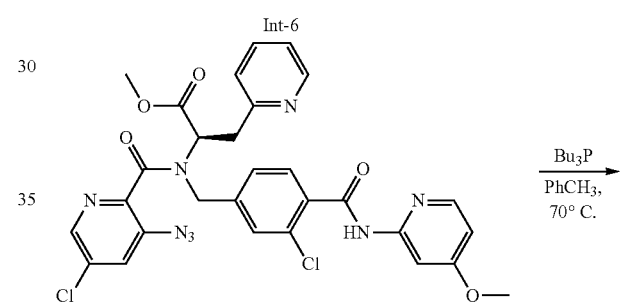
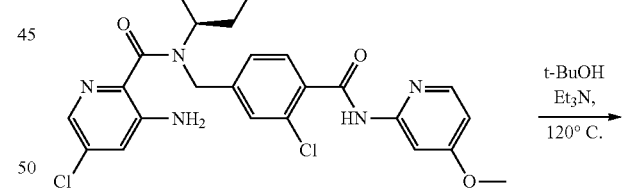
Example 3
Synthesis of 3-amino-5-chloropicolinonitrile (23): To a solution of 5-chloro-3-nitropicolinonitrile (22, 50 g, 0.273 mol) in acetic acid (250 mL) cooled to 0° C., iron power (76.5 g, 1.36 mol) was added slowly in portions. The reaction was then stirred for 2 h when TLC showed consumption of starting material. The reaction mixture was then filtered over a bed of celite and celite bed was washed with methanol. The combined mother liquor was evaporated under reduced pressure and crude was dissolved in ethyl acetate followed by washing with sodium carbonate solution. The organic layer was washed with brine, dried over anhydrous sodium sulfate and solvent was removed under reduced pressure to afford 3-amino-5-chloropicolinonitrile (26, 40.0 g, 96%) as off white solid.

Synthesis of 3-amino-5-chloropicolinic acid as HCl salt (24): A solution of 3-amino-5-chloropicolinonitrile (23, 40 g, 0.261 mol) in HCl (150 mL, 36% in water) was heated at 100° C. for 16 h. After completion as confirmed by TLC, the volatiles were removed under reduced pressure to afford 3-amino-5-chloropicolinic acid as 2HCl salt (24, 58 g, 90%) as brown green solid.

Synthesis of methyl 3-amino-5-chloropicolinate (25): To a solution of 3-amino-5-chloropicolinic acid as HCl salt (24, 58 g, 0.237 mol) in DMF (600 mL), $K_2CO_3$ (98 g, 0.711 mol) was added at 0° C. The reaction was stirred for 15 min and then methyl iodide (67.3 g, 0.474 mol) was added at 0° C. The reaction was then stirred for 12 h and monitored by TLC and LCMS which showed consumption of starting material. The reaction was quenched with water and extracted with ethyl acetate (3×600 mL) and organic layer was washed with brine and dried over anhydrous sodium sulfate. The solvent was removed under reduced pressure to get crude which was purified by silica gel column chromatography eluting the product with 40-50% ethyl acetate in hexane to afford methyl 3-amino-5-chloropicolinate (25, 32 g, 78%) as light yellow liquid.

Synthesis of methyl 3-azido-5-chloropicolinate (26): To a solution of methyl 3-amino-5-chloropicolinate (25, 32 g, 0.172 mol) in HCl (180 mL) and water (180 mL) at 0° C., $NaNO_2$ (17.8 g, 0.258 mol) was added and the mixture was stirred for 30 min. The particles were removed by filtration and the mother liquor was cooled to 0° C. followed by addition of $NaN_3$ (22.4 g, 0.344 mol) at 0° C. The mixture was stirred for 30 min and the precipitated solid was filtered. The mother liquor was extracted with ethyl acetate (2×300 mL) and the solid was also dissolved in ethyl acetate, dried over anhydrous sodium sulfate, filtered and concentrated to get solid which was triturated with pentane and dried under vacuum to afford methyl 3-azido-5-chloropicolinate (26, 28 g, 77%) as off white solid.

Synthesis of 3-azido-5-chloropicolinic acid (27): To a solution of methyl 3-azido-5-chloropicolinate (26, 28.0 g, 0.132 mol) in THF (140 mL), methanol (140 mL), a solution of LiOH·$H_2O$ (22.2 g, 0.528 mol) in water (80 mL) was added and the reaction mixture was stirred for 16 h. After completion of the reaction as monitored by TLC, the solvent was removed under reduced pressure and the crude was again dissolved in water (100 mL), cooled to 0° C. and treated with HCl to bring the pH~4-5. The mixture was stirred for 10 min and then extracted with ethyl acetate (3×300 mL), dried over anhydrous sodium sulfate and solvent was removed to get solid. The solid was triturated with pentane and dried under high vacuum to afford 3-azido-5-chloropicolinic acid (27, 22.0 g, 84%) as yellow solid.

Synthesis of 3-azido-5-chloropicolinoyl chloride (28): A solution of 3-azido-5-chloropicolinic acid (27, 6.0 g, 0.030 mol) in dichloromethane (50 mL), oxalyl chloride (4.23 g, 0.33 mol) was added at 0° C. followed by addition of four drops of dimethylformamide. The reaction mixture was then stirred at room temperature for 2 h when TLC showed consumption of starting material by quenching with methanol. The volatiles were removed under reduced pressure and crude was dried under high vacuum to afford 3-azido-5-chloropicolinoyl chloride (28, 6.2 g) as reddish brown solid and used for the next reaction without further purification.

Synthesis of (R)-methyl 2-(3-azido-5-chloro-N-(3-chloro-4-((4-methoxypyridin-2-yl)carbamoyl)benzyl)picolinamido)-3-(pyridin-2-yl)propanoate (29): A solution of (R)-methyl 2-((3-chloro-4-((4-methoxypyridin-2-yl)carbamoyl)benzyl)amino)-3-(pyridin-2-yl)-propanoate (Int 6, 4.9 g, 0.0108 mol) in dichloromethane (40 mL) was cooled to 0° C. and DIPEA (2.8 mL, 0.016 mmol) was added and the mixture was stirred for 10 min. A solution of 3-azido-5-chloropicolinoyl chloride (28, 2.5 g, 0.0115 mol) in dichloromethane (5 mL) was added slowly at same temperature. The reaction was monitored by TLC which showed consumption of starting material after 45 min. The reaction was quenched by addition of water (50 mL) and extracted with dichloromethane (3×100 mL). The organic layer was dried over anhydrous sodium sulfate and solvent was removed under reduced pressure to get the crude. The crude was then purified by flash silica gel column chromatography using 70-80% ethyl acetate in hexane. The fraction containing product was concentrated to get solid which was triturated with pentane and dried under vacuum to afford (R)-methyl 2-(3-azido-5-chloro-N-(3-chloro-4-((4-methoxypyridin-2-yl)carbamoyl)benzyl)picolinamido)-3-(pyridin-2-yl)propanoate (29, 3.9 g, 57%) as brown sticky liquid.

Synthesis of (R)-methyl 2-(3-amino-5-chloro-N-(3-chloro-4-((4-methoxypyridin-2-yl)carbamoyl)benzyl)picolinamido)-3-(pyridin-2-yl)propanoate (30): A solution of (R)-methyl 2-(3-azido-5-chloro-N-(3-chloro-4-((4-methoxypyridin-2-yl)carbamoyl)benzyl)picolin-amido)-3-(pyridin-2-yl)propanoate (29, 3.9 g, 6.15 mmol) in toluene (35 mL) at room temperature was treated with tributylphosphene (1.57 g, 7.38 mmol) and the mixture was stirred at 70° C. for 16 h. After consumption of starting material as confirmed by TLC, the solvent was removed under reduced pressure to get crude. The crude was then dissolved in THF (10 mL), water (5 mL) and was treated with TFA (3 mL) at room temperature and stirred for 30 min. The solvent was removed under reduced pressure and then crude was dissolved in aq $NaHCO_3$ water and ethyl acetate. The organic layer was separated and aqueous layer was back extracted with ethyl acetate. The combined organic layer was washed with brine, dried over anhydrous sodium sulfate and solvent was removed under reduced pressure to afford crude. The crude was purified by silica gel column chromatography eluting the product with 75-85% ethyl acetate in hexane to afford (R)-methyl 2-(3-amino-5-chloro-N-(3-chloro-4-((4-methoxypyridin-2-yl)carbamoyl)benzyl)picolinamido)-3-(pyridin-2-yl)propanoate (30, 2.7 g, 72%) as brown solid.

Synthesis of (R)-2-chloro-4-((8-chloro-2,5-dioxo-3-(pyridin-2-ylmethyl)-2,3-dihydro-1H-pyrido[3,2-e][1,4]diazepin-4(5H)-yl)methyl)-N-(4-methoxypyridin-2-yl)benzamide (Example 3): To a solution of (R)-methyl 2-(3-amino-5-chloro-N-(3-chloro-4-((4-methoxypyridin-2-yl) carbamoyl)benzyl)picolinamido)-3-(pyridin-2-yl) propanoate (30, 2.7 g, 4.44 mmol) in tert-butyl alcohol (4 mL), triethylamine (4 mL) was added. The reaction mixture was then heated at 100-120° C. for 72 h when TLC and LCMS showed consumption of starting material. The mixture was then cooled to room temperature and quenched with water (20 mL) followed by extraction with ethyl acetate. The organic layer was separated and aqueous layer was back extracted with ethyl acetate (2×50 mL) and combined organic layer was washed with brine, dried over anhydrous sodium sulfate and concentrated under reduced pressure to afford crude. The crude was purified by silica gel column chromatography eluting the product with 2-5% methanol in ethyl acetate to afford 2-chloro-4-((8-chloro-2,5-dioxo-3-(pyridin-2-ylmethyl)-2,3-dihydro-1H-pyrido[3,2-e][1,4]diazepin-4(5H)-yl)methyl)-N-(4-methoxypyridin-2-yl)benzamide (Example 4 racemic, 0.80 g) as offwhite solid. The compound was then purified by chiral prep HPLC to afford (R)-2-chloro-4-((8-chloro-2,5-dioxo-3-(pyridin-2-ylmethyl)-2,3-dihydro-1H-pyrido[3,2-e][1,4]diazepin-4(5H)-yl)methyl)-N-(4-methoxypyridin-2-yl)benzamide (Example 3, 320 mg) desired isomer.

LCMS (ES) m/z 577.21 [M+1]=; (Purity 95.080); chiral purity (95:5), Column Name: Chiralpak IB N-5 (4.6×250) mm, 5µ, Mobile Phase: $CO_2$/0.2% TEA in MeOH (60:40), Flow rate: 3.0 mL/min, Flow mode: Isocratic, Column Temperature: 35° C., ABPR Pressure: 1500 psi; $^1$H NMR (400 MHz, DMSO-d6) δ 2.70-2.86, 3.10-3.20 and 3.50-3.60 (m, 2H), 3.85 (s, 3H), 4.40-4.90 (m, 3H), 6.73 (d, J=5.2 Hz, 1H), 6.90-7.32 (m, 3H), 7.35 (s, 1H), 7.40-7.50 (m, 2H), 7.60 (br s, 1H), 7.75 (s, 1H), 8.13 (d, J=5.2 Hz, 1H), 8.28 (s, 1H), 8.36 (br s, 1H), 10.52 (br s, 1H).

Characterization Data

Table 1 includes characterization data for selected examples, and $EC_{50}$ values according to the cell-based morphology assay protocol described below. The $EC_{50}$ values are designated as A, B, or C where: A<0.1 µM; B=0.1-0.99 µM; C=1.0-9.9 µM and D=10-20 µM.

TABLE 1

| Ex. No. | Structure; IUPAC Name. | LCMS; $^1$HNMR; cellular morphology $EC_{50}$ range (µM). | Synthesis Method |
|---|---|---|---|
| 1 | 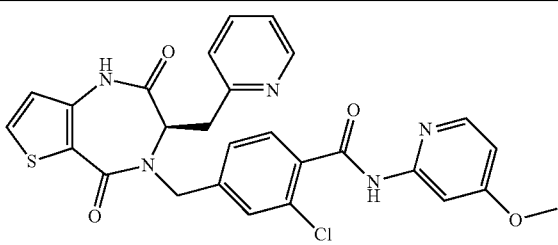<br>(R)-2-chloro-4-((2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)benzamide | LCMS (ES) m/z = 548.15 [M + 1]$^+$; $^1$H NMR (400 MHz, DMSO-d6) δ 2.90-3.15 and 3.50-3.65 (m, 2H), 3.84 (s, 3H), 4.10-5.20 (m, 3H), 6.75 (dd, J = 5.6 and 2.0 Hz, 1H), 6.86 (d, J = 4.4 Hz, 1H), 7.05-7.30 (m, 3H), 7.35 (s, 1H), 7.47 (d, J = 8.0 Hz, 1H), 7.70 (t, J = 7.2 Hz, 1H), 7.79 (s, 1H), 7.89 (d, J = 5.2 Hz, 1H), 8.13 (d, J = 5.6 Hz, 1H), 8.46 (br s, 1H), 10.92 (s, 1H), 11.14 (br s, 1H); $EC_{50}$ = A. | A |
| 2 | 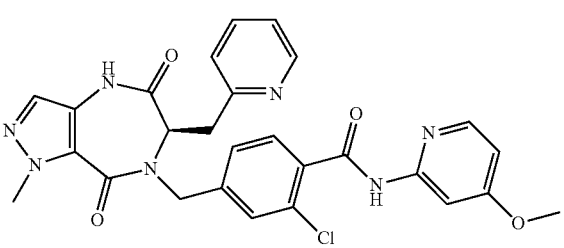<br>(R)-2-chloro-N-(4-methoxypyridin-2-yl)-4-((1-methyl-5,8-dioxo-6-(pyridin-2-ylmethyl)-4,5,6,8-tetrahydropyrazolo[4,3-e][1,4]diazepin-7(1H)-yl)methyl)benzamide | LCMS (ES) m/z = 546.20 [M + 1]$^+$; $^1$H NMR (400 MHz, DMSO-d6) δ 2.85-3.25 and 3.56-3.68 (m, 2H), 3.84 (s, 3H), 4.04 and 4.06 (2 × s, 3H), 4.60-5.15 (m, 3H), 6.76 (dd, J = 5.6 and 2.0 Hz, 1H), 7.15-7.35 (m, 5H), 7.43-7.50 (m, 1H), 7.65-7.73 (m, 1H), 7.78 (s, 1H), 8.14 (d, J = 6.0 Hz, 1H), 8.38 and 8.48 (m, 1H), 10.49 and 10.66 (2 × s, 1H), 10.93 (s, 1H); $EC_{50}$ = A. | B |
| 3 | 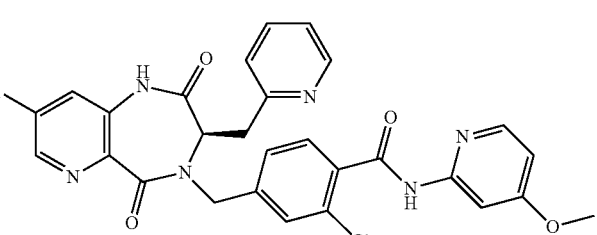<br>(R)-2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(4-methoxypyridin-2-yl)benzamide | LCMS (ES) m/z = 577.21 [M + 1]$^+$; $^1$H NMR (400 MHz, DMSO-d6) δ 2.70-2.86, 3.10-3.20 and 3.50-3.60 (m, 2H), 3.85 (s, 3H), 4.40-4.90 (m, 3H), 6.73 (d, J = 5.2 Hz, 1H), 6.90-7.32 (m, 3H), 7.35 (s, 1H), 7.40-7.50 (m, 2H), 7.60 (br s, 1H), 7.75 (s, 1H), 8.13 (d, J = 5.2 Hz, 1H), 8.28 (s, 1H), 8.36 (br s, 1H), 10.52 (br s, 1H); $EC_{50}$ = A. | C |

TABLE 1-continued

| Ex. No. | Structure; IUPAC Name. | LCMS; $^1$HNMR; cellular morphology $EC_{50}$ range (μM). | Synthesis Method |
|---|---|---|---|
| 4 | 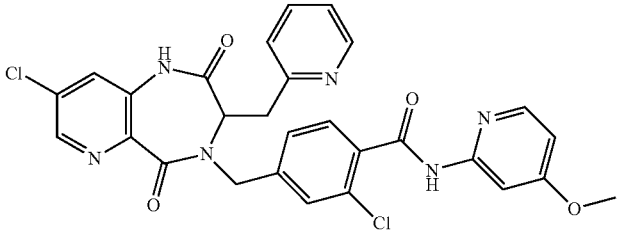<br>2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(4-methoxypyridin-2-yl)benzamide | LCMS (ES) m/z = 577.21 [M + 1]$^+$; $^1$H NMR (400 MHz, DMSO-d6) δ 2.70-2.86, 3.10-3.20 and 3.50-3.60 (m, 2H), 3.85 (s, 3H), 4.40-4.90 (m, 3H), 6.73 (d, J = 5.2 Hz, 1H), 6.90-7.32 (m, 3H), 7.35 (s, 1H), 7.40-7.50 (m, 2H), 7.60 (br s, 1H), 7.75 (s, 1H), 8.13 (d, J = 5.2 Hz, 1H), 8.28 (s, 1H), 8.36 (br s, 1H), 10.52 (br s, 1H); $EC_{50}$ = A. | C |
| 5 | 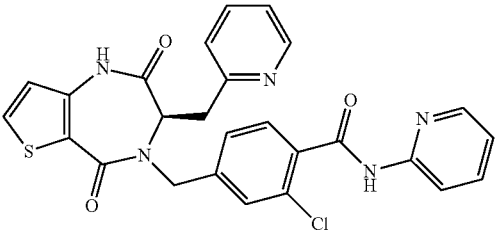<br>(R)-2-chloro-4-((2,5-dioxo-3-(pyridin-2-ylmethyl)-1,2,3,5-tetrahydro-4H-thieno[3,2-e][1,4]diazepin-4-yl)methyl)-N-(pyridin-2-yl)benzamide | LCMS (ES) m/z = 518.13 [M + 1]$^+$; $^1$H NMR (400 MHz, DMSO-d6) δ 2.90-3.10 and 3.45-3.65 (m, 2H), 4.10-5.20 (m, 3H), 6.75 (d, J = 4.4, 1H), 7.05-7.32 (m, 4H), 7.36 (s, 1H), 7.49 (d, J = 7.6 Hz, 1H), 7.70 (t, J = 7.2 Hz, 1H), 7.83 (t, J = 8.4 Hz, 1H), 7.89 (d, J = 5.2 Hz, 1H), 8.14 (d, J = 7.2 Hz, 1H), 8.32 (d, J = 4.4 Hz, 1H), 8.46 (br s, 1H), 10.96 (s, 1H), 11.11 (br s, 1H); Chiral purity (89:11); $EC_{50}$ = B. | A |
| 6 | 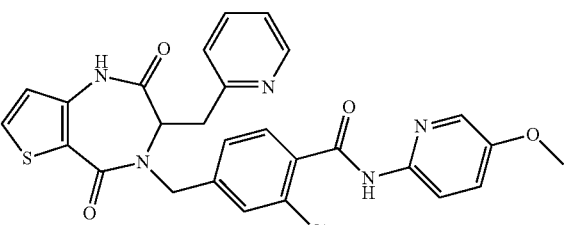<br>2-chloro-4-((2,5-dioxo-3-(pyridin-2-ylmethyl)-1,2,3,5-tetrahydro-4H-thieno[3,2-e][1,4]diazepin-4-yl)methyl)-N-(5-methoxypyridin-2-yl)benzamide | LCMS (ES) m/z = 548.42 [M + 1]$^+$; $^1$H NMR (400 MHz, DMSO-d6) δ 2.90-3.15 and 3.50-3.65 (m, 2H), 3.82 (s, 3H), 4.10-5.20 (m, 3H), 6.87 (d, J = 4.0 Hz, 1H), 6.86 (d, J = 4.4 Hz, 1H), 7.05-7.30 (m, 3H), 7.36 (s, 1H), 7.45-7.55 (m, 2H), 7.71 (t, J = 7.2 Hz, 1H), 7.90 (d, J = 5.2 Hz, 1H), 8.04-8.15 (m, 2H), 8.47 (br s, 1H), 10.84 (s, 1H), 11.15 (br s, 1H); Chiral HPLC purity (1:1); CHIRALPAK IB (4.6 · 250)mm, 5μ CO2/0.2% TEA in MeOH (60:40), flow rate 3 mL/min; $EC_{50}$ = A. | A |

TABLE 1-continued

| Ex. No. | Structure; IUPAC Name. | LCMS; ¹HNMR; cellular morphology EC$_{50}$ range (μM). | Synthesis Method |
|---|---|---|---|
| 7 | 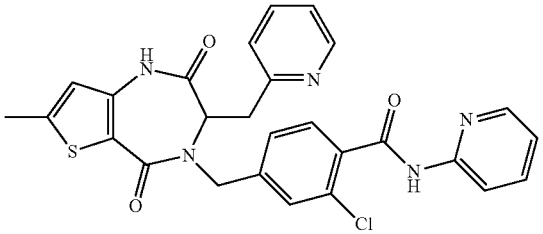<br>2-chloro-4-((7-methyl-2,5-dioxo-3-(pyridin-2-ylmethyl)-1,2,3,5-tetrahydro-4H-thieno[3,2-e][1,4]diazepin-4-yl)methyl)-N-(pyridin-2-yl)benzamide | LCMS (ES) m/z = 532.17 [M + 1]⁺; ¹H NMR (400 MHz, DMSO-d6) δ 2.47 (s, 3H), 2.97-3.15 and 3.50-3.65 (m, 2H), 4.05-5.15 (m, 3H), 6.62 (s, 1H), 7.05-7.30 (m, 4H), 7.34 (s, 1H), 7.49 (d, J = 7.6 Hz, 1H), 7.70 (t, J = 7.6 Hz, 1H), 7.83 (d, J = 7.2 Hz, 1H), 8.14 (d, J = 8.0 Hz, 1H), 8.33 (d, J = 4.0 Hz, 1H), 8.46 (br s, 1H), 10.96 (s, 1H), 11.08 (br s, 1H); Chiral purity (37:63); EC$_{50}$ = B. | A |
| 8 | 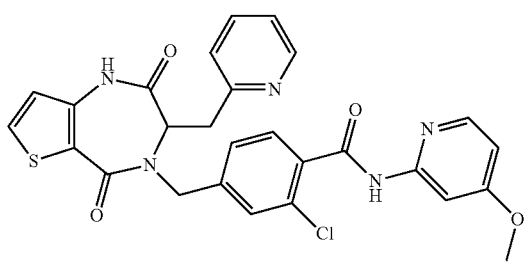<br>2-chloro-4-((2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)benzamide | LCMS (ES) m/z = 548.21 [M + 1]⁺; ¹H NMR (400 MHz, DMSO-d6) δ 2.90-3.15 and 3.50-3.65 (m, 2H), 3.84 (s, 3H), 4.10-5.20 (m, 3H), 6.75 (dd, J = 5.6 and 2.0 Hz, 1H), 6.86 (d, J = 4.4 Hz, 1H), 7.05-7.30 (m, 3H), 7.35 (s, 1H), 7.47 (d, J = 8.0 Hz, 1H), 7.70 (t, J = 7.2 Hz, 1H), 7.79 (s, 1H), 7.89 (d, J = 5.2 Hz, 1H), 8.13 (d, J = 5.6 Hz, 1H), 8.46 (br s, 1H), 10.60-11.10 (br s, 2H); Chiral HPLC purity (22:78); CHIRALPAK IB N-5 (4.6 · 250)mm, 5μ, CO$_2$/0.2% TEA in MeOH (60:40), flow rate 3 mL/min; EC$_{50}$ = A. | A |
| 9 | 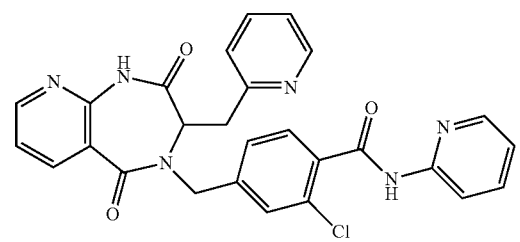<br>2-chloro-4-((2,5-dioxo-3-(pyridin-2-ylmethyl)-1,2,3,5-tetrahydro-4H-pyrido[2,3-e][1,4]diazepin-4-yl)methyl)-N-(pyridin-2-yl)benzamide | LCMS (ES) m/z = 513.18 [M + 1]⁺; ¹H NMR (400 MHz, DMSO-d6) δ 2.75-3.00 (m, 1H), 3.20-3.25 and 3.58-3.67 (m, 1H), 4.25-5.10 (m, 3H), 7.00-7.52 (m, 8H), 7.62-7.70 (m, 1H), 7.83 (t, J = 7.6 Hz, 1H), 8.15 (d, J = 7.2 Hz, 1H), 8.25-8.36 (m, 2H), 8.45 and 8.59 (2 s, 1H), 10.90-11.15 (m, 2H); Chiral purity (46:54); EC$_{50}$ = B. | C |

TABLE 1-continued

| Ex. No. | Structure; IUPAC Name. | LCMS; ¹HNMR; cellular morphology EC$_{50}$ range (μM). | Synthesis Method |
|---|---|---|---|
| 10 | 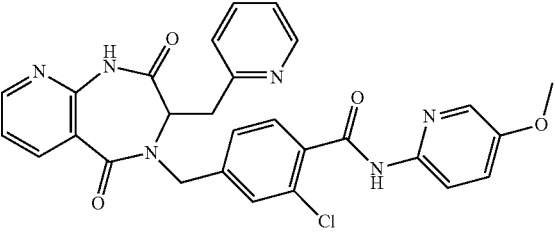<br>2-chloro-4-((2,5-dioxo-3-(pyridin-2-ylmethyl)-1,2,3,5-tetrahydro-4H-pyrido[2,3-e][1,4]diazepin-4-yl)methyl)-N-(5-methoxypyridin-2-yl)benzamide | LCMS (ES) m/z = 543.18 [M + 1]⁺; ¹H NMR (400 MHz, DMSO-d6) δ 2.75-3.00 (m, 1H), 3.20-3.25 and 3.58-3.67 (m, 1H), 3.81 (s, 3H), 4.25-5.10 (m, 3H), 7.00-7.50 (m, 7H), 7.62-7.72 (m, 1H), 8.02-8.12 (m, 2H), 8.25-8.54 (m, 3H), 10.81 and 10.84 (2 s, 1H), 11.00 and 11.08 (2 s, 1H); Chiral purity (45:55); EC$_{50}$ = C. | C |
| 11 | 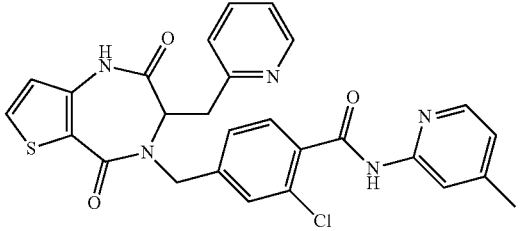<br>2-chloro-4-((2,5-dioxo-3-(pyridin-2-ylmethyl)-1,2,3,5-tetrahydro-4H-thieno[3,2-e][1,4]diazepin-4-yl)methyl)-N-(4-methylpyridin-2-yl)benzamide | LCMS (ES) m/z = 532.15 [M + 1]⁺; ¹H NMR (400 MHz, DMSO-d6) δ 2.34 (s, 3H), 2.95-3.10 and 3.55-3.65 (m, 2H), 4.15-5.20 (m, 3H), 6.86 (d, J = 5.2 Hz, 1H), 6.98 (d, J = 5.2 Hz, 1H), 7.05-7.23 (m, 2H), 7.24 (d, J = 8.0 Hz, 1H), 7.35 (s, 1H), 7.47 (d, J = 7.6 Hz, 1H), 7.70 (t, J = 7.2 Hz, 1H), 7.89 (d, J = 5.6 Hz, 1H), 8.02 (s, 1H), 8.17 (d, J = 7.2 Hz, 1H), 8.46 (br s, 1H), 10.88 (s, 1H), 11.13 (br s, 1H); Chiral purity 50:50); EC$_{50}$ = A. | A |
| 12 | 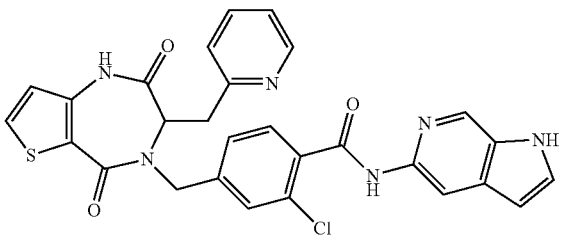<br>2-chloro-4-((2,5-dioxo-3-(pyridin-2-ylmethyl)-1,2,3,5-tetrahydro-4H-thieno[3,2-e][1,4]diazepin-4-yl)methyl)-N-(1H-pyrrolo[2,3-c]pyridin-5-yl)benzamide | LCMS (ES) m/z = 557.16 [M + 1]⁺; ¹H NMR (400 MHz, DMSO-d6) δ 2.95-3.10 and 3.50-3.60 (m, 2H), 4.10-5.15 (m, 3H), 6.48-6.55 (m, 1H), 6.87 (d, J = 4.8 Hz, 1H), 7.00-7.30 (m, 3H), 7.35 (s, 1H), 7.48 (d, J = 7.6 Hz, 1H), 7.59 (t, J = 2.4 Hz, 1H), 7.68-7.75 (m, 1H), 7.88-7.93 (m, 1H), 8.30 (s, 1H), 8.40-8.52 (m, 2H), 10.58 (s, 1H), 11.12 (br s, 1H), 13.50 (s, 1H). Chiral purity (1:1) Column Name: CHIRCEL OJH (4.6 · 250)mm, 5μ Mobile Phase: CO$_2$/MeOH(60:40), Flow rate: 3.0 mL/min, Flow mode: Isocratic, Column Temperature: 35° C., ABPR Pressure: 1500 psi: EC$_{50}$ = B. | A |

TABLE 1-continued

| Ex. No. | Structure; IUPAC Name. | LCMS; ¹HNMR; cellular morphology EC$_{50}$ range (μM). | Synthesis Method |
|---|---|---|---|
| 13 | 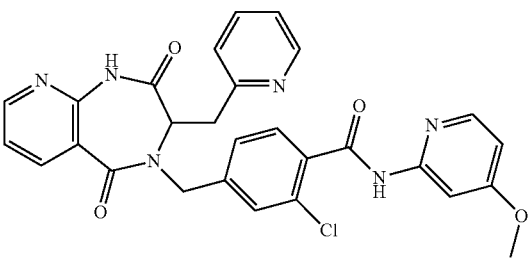<br>2-chloro-4-((2,5-dioxo-3-(pyridin-2-ylmethyl)-1,2,3,5-tetrahydro-4H-pyrido[2,3-e][1,4]diazepin-4-yl)methyl)-N-(4-methoxypyridin-2-yl)benzamide | LCMS (ES) m/z = 543.18 [M + 1]$^+$; ¹H NMR (400 MHz, DMSO-d6) δ 3.00-3.32 (m, 1H), 3.55-3.65 (m, 1H), 4.40-5.10 (m, 3H), 7.05-7.35 (m, 4H), 7.42 (s, 1H), 7.49 (d, J = 7.6 Hz, 1H), 7.64-7.71 (m, 1H), 7.77-7.86 (m, 2H), 8.15 (d, J = 8.0 Hz, 1H), 8.30-8.50 (m, 3H), 10.86-11.15 (m, 2H). Chiral purity (43:57); Column Name: CHIRALPAK IB (4.6 · 250 )mm, 5 mic, Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = A. | C |
| 14 | 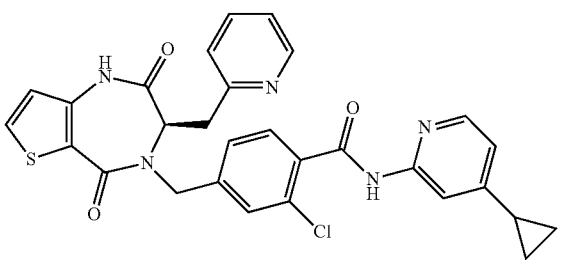<br>(R)-2-chloro-N-(4-cyclopropylpyridin-2-yl)-4-((2,5-dioxo-3-(pyridin-2-ylmethyl)-1,2,3,5-tetrahydro-4H-thieno[3,2-e][1,4]diazepin-4-yl)methyl)benzamide | LCMS (ES) m/z = 558.17 [M + 1]$^+$; ¹H NMR (400 MHz, DMSO-d6) δ 0.75-0.82 (m, 2H), 1.05-1.12 (m, 2H), 1.95-2.03 (m, 2H), 2.90-3.12 and 3.50-3.62 (m, 2H), 4.10-5.20 (m, 3H), 6.83 (dd, J = 5.2 and 2.0 Hz, 1H), 6.86 (d, J = 8.2 Hz, 1H), 7.05-7.28 (m, 3H), 7.35 (s, 1H), 7.47 (d, J = 7.6 Hz, 1H), 7.70 (t, J = 7.2 Hz, 1H), 7.90 (d, J = 5.6 Hz, 1H), 8.02 (br s, 1H), 8.12 (d, J = 7.2 Hz, 1H), 8.46 (br s, 1H), 10.85 (s, 1H), 11.11 (br s, 1H), Chiral purity (2:98); EC$_{50}$ = A. | A |
| 15 | 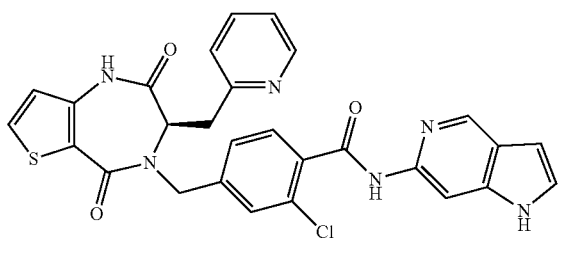<br>(R)-2-chloro-4-((2,5-dioxo-3-(pyridin-2-ylmethyl)-1,2,3,5-tetrahydro-4H-thieno[3,2-e][1,4]diazepin-4-yl)methyl)-N-(1H-pyrrolo[3,2-c]pyridin-6-yl)benzamide | LCMS (ES) m/z = 557.16 [M + 1]$^+$; ¹H NMR (400 MHz, DMSO-d6) δ 2.90-3.10 and 3.50-3.65 (m, 2H), 4.10-5.20 (m, 3H), 6.87 (d, J = 4.0 Hz, 1H), 7.05-7.30 (m, 3H), 7.36 (s, 1H), 7.50 (d, J = 7.6 Hz, 1H), 7.71 (t, J = 7.6 Hz, 1H), 7.90 (d, J = 5.2 Hz, 1H), 8.22 (s, 1H), 8.40-8.55 (m, 2H), 8.83 (s, 1H), 10.91 (s, 1H), 11.25 (br s, 1H), 13.48 (br s, 1H); Chiral purity (3:97) Column Name: CHIRALPAK IB (4.6 · 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = A. | A |

TABLE 1-continued

| Ex. No. | Structure; IUPAC Name. | LCMS; $^1$HNMR; cellular morphology $EC_{50}$ range (μM). | Synthesis Method |
|---|---|---|---|
| 16 | 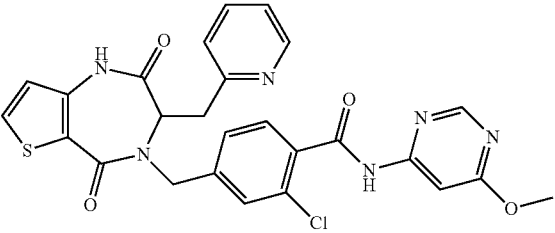<br>2-chloro-4-((2,5-dioxo-3-(pyridin-2-ylmethyl)-1,2,3,5-tetrahydro-4H-thieno[3,2-e][1,4]diazepin-4-yl)methyl)-N-(6-methoxypyrimidin-4-yl)benzamide | LCMS (ES) m/z = 549.13 [M + 1]$^+$; $^1$H NMR (400 MHz, DMSO-d6) δ 2.90-3.10 (m, 2H), 3.92 (s, 3H), 4.10-5.20 (m, 3H), 6.86 (d, J = 4.4 Hz, 1H), 7.05-7.30 (m, 3H), 7.37 (s, 1H), 7.50 (d, J = 8.0 Hz, 1H), 7.53 (s, 1H), 7.70 (t, J = 7.2 Hz, 1H), 7.89 (d, J = 5.2 Hz, 1H), 8.46 (br s, 1H), 8.56 (s, 1H), 1.13 (br s, 1H), 11.34 (s, 1H); Chiral purity (32:68) Column Name: CHIRALPAK IB(4.6 · 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi; $EC_{50}$ = A. | A |
| 17 | 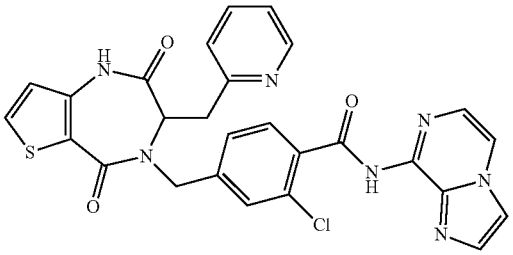<br>2-chloro-4-((2,5-dioxo-3-(pyridin-2-ylmethyl)-1,2,3,5-tetrahydro-4H-thieno[3,2-e][1,4]diazepin-4-yl)methyl)-N-(imidazo[1,2-a]pyrazin-8-yl)benzamide | LCMS (ES) m/z = 558.11 [M + 1]$^+$; 1H NMR (400 MHz, DMSO-d6) δ 2.90-3.15 and 3.50-3.65 (m, 2H), 4.05-5.15 (m, 3H), 6.87 (d, J = 6.0 Hz, 1H), 7.05-7.30 (m, 3H), 7.35 (s, 1H), 7.51 (d, J = 7.6 Hz, 1H), 7.56 (d, J = 7.6 Hz, 1H), 7.69 (t, J = 7.6 Hz, 1H), 7.74 (s, 1H), 7.89 (d, J = 7.2 Hz, 1H), 8.12 (s, 1H), 8.39 (d, J = 4.4 Hz, 1H), 8.46 (br s, 1H), 10.60-11.20 (m, 2H); Chiral purity (1:1); Column Name: CHIRALPAK IB N-5 (4.6 · 250)mm, 5μ, Mobile Phase: CO$_2$/0.2% TEA in MeOH (60:40) Flow rate: 3.0 mL/min Flow mode: Isocratic Column Temperature: 35° C. ABPR Pressure: 1500 psi; $EC_{50}$ = B. | A |
| 18 | 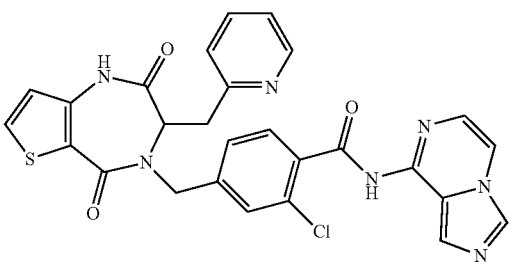<br>2-chloro-4-((2,5-dioxo-3-(pyridin-2-ylmethyl)-1,2,3,5-tetrahydro-4H-thieno[3,2-e][1,4]diazepin-4-yl)methyl)-N-(imidazo[1,5-a]pyrazin-8-yl)benzamide | LCMS (ES) m/z = 588.14 [M + 1]$^+$; $^1$H NMR (400 MHz, DMSO-d6) δ 2.90-3.10 and 3.50-3.62 (m, 2H), 4.05-5.15 (m, 3H), 6.84 (d, J = 4.8 Hz, 1H), 7.05-7.30 (m, 4H), 7.36 (s, 1H), 7.40 (t, J = 2.4 Hz, 1H), 7.60 (d, J = 7.2 Hz, 1H), 7.70 (t, J = 7.2 Hz, 1H), 7.86-7.94 (m, 2H), 8.10 (br s, 1H), 8.46 (br s, 1H), 8.53 (s, 1H), 11.11 (br s, 1H), 11.60 (br s, 1H); Chiral purity (30:70) Column Name: CHIRALPAK IB | A |

TABLE 1-continued

| Ex. No. | Structure; IUPAC Name. | LCMS; ¹HNMR; cellular morphology EC$_{50}$ range (μM). | Synthesis Method |
|---|---|---|---|
| | | (4.6 · 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = B. | |
| 19 | 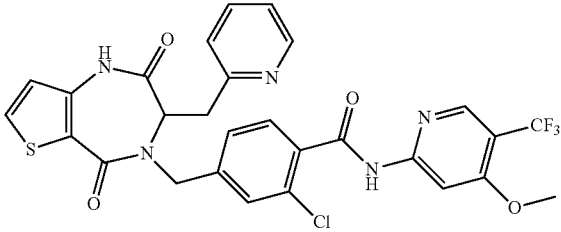<br>2-chloro-4-((2,5-dioxo-3-(pyridin-2-ylmethyl)-1,2,3,5-tetrahydro-4H-thieno[3,2-e][1,4]diazepin-4-yl)methyl)-N-(4-methoxy-5-(trifluoromethyl)pyridin-2-yl)benzamide | LCMS (ES) m/z = 616.11 [M + 1]$^+$; ¹H NMR (400 MHz, DMSO-d6) δ 2.90-3.10 and 3.40-3.55 (m, 2H), 3.99 (s, 3H), 4.14-5.10 (m, 3H), 6.86 (d, J = 4.8 Hz, 1H), 7.05-7.30 (m, 3H), 7.37 (s, 1H), 7.51 (d, J = 8.0 Hz, 1H), 7.70 (t, J = 7.2 Hz, 1H), 7.89 (d, J = 5.2 Hz, 1H), 8.09 (s, 1H), 8.40-8.52 (m, 2H), 11.13 (br s, 1H), 11.37 (s, 1H); Chiral purity (30:70) Column Name: CHIRALPAK IC (4.6 · 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = A | A |
| 20 | 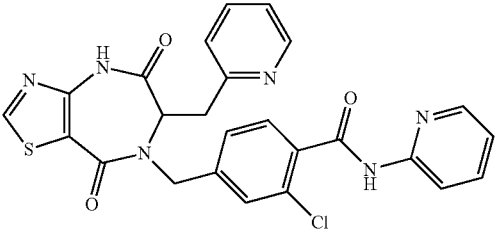<br>2-chloro-4-((5,8-dioxo-6-(pyridin-2-ylmethyl)-4,5,6,8-tetrahydro-7H-thiazolo[4,5-e][1,4]diazepin-7-yl)methyl)-N-(pyridin-2-yl)benzamide | LCMS (ES) m/z = 519.11 [M + 1]$^+$; ¹H NMR (400 MHz, DMSO-d6, vt NMR) δ 3.10-3.35 (m, 2H), 4.35-4.50 (m, 1H), 4.80-4.90 (m, 2H), 7.13 (dd, J = 8.0 and 5.2 Hz, 1H), 7.18-7.25 (m, 2H), 7.27 (d, J = 8.0 Hz, 1H), 7.37 (s, 1H), 7.49 (d, J = 8.0 Hz, 1H), 7.69 (t, J = 7.2 Hz, 1H), 7.81 (t, J = 7.6 Hz, 1H), 8.09 (d, J = 8.8 Hz, 1H), 8.32 (d, J = 4.4 Hz, 1H), 8.46 (d, J = 4.0 Hz, 1H), 9.23 (s, 1H), 10.60 (s, 1), 11.46 (s, 1H); Chiral purity (34:66); EC$_{50}$ = B. | A |
| 21 | 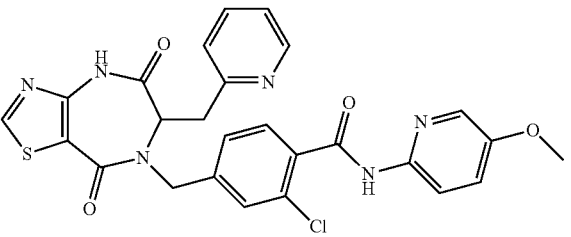<br>2-chloro-4-((5,8-dioxo-6-(pyridin-2-ylmethyl)-4,5,6,8-tetrahydro-7H-thiazolo[4,5-e][1,4]diazepin-7-yl)methyl)-N-(5-methoxypyridin-2-yl)benzamide | LCMS (ES) m/z = 549.16 [M + 1]$^+$; ¹H NMR (400 MHz, DMSO-d6) δ 2.90-3.15 and 3.55-3.65 (m, 2H), 3.81 (s, 3H), 4.10-5.20 (m, 3H), 7.10-7.30 (m, 3H), 7.37 (s, 1H), 7.45-7.52 (m, 2H), 7.70 (t, J = 6.0 Hz, 1H), 8.03-8.12 (m, 2H), 8.46 (br s, 1H), 9.28 (s, 1H), 10.82 (s, 1H), 11.74 (br s, 1H); EC$_{50}$ = B. | A |

TABLE 1-continued

| Ex. No. | Structure; IUPAC Name. | LCMS; ¹HNMR; cellular morphology EC$_{50}$ range (μM). | Synthesis Method |
|---|---|---|---|
| 22 | 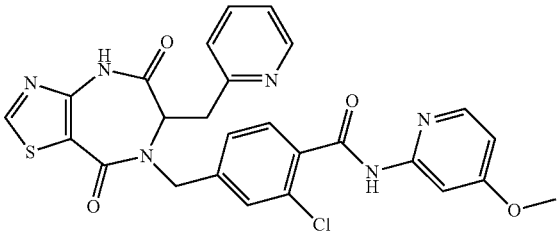<br>2-chloro-4-((5,8-dioxo-6-(pyridin-2-ylmethyl)-4,5,6,8-tetrahydro-7H-thiazolo[4,5-e][1,4]diazepin-7-yl)methyl)-N-(4-methoxypyridin-2-yl)benzamide | LCMS (ES) m/z = 549.16 [M + 1]⁺; ¹H NMR (400 MHz, DMSO-d6) δ 2.95-3.13 and 3.55-3.65 (m, 2H), 3.84 (s, 3H), 4.10-5.20 (m, 3H), 6.75 (dd, J = 4.8 and 2.0 Hz, 1H), 7.10-7.35 (m, 3H), 7.37 (s, 1H), 7.47 (d, J = 7.6 Hz, 1H), 7.70 (t, J = 7.2 Hz, 1H), 7.79 (s, 1H), 8.13 (d, J = 6.0 Hz, 1H), 8.45 (br s, 1H), 9.28 (s, 1H), 10.93 (s, 1H), 11.80 (br s, 1H); Chiral purity (15:85) Column Name: CHIRALPAK IB (4.6 · 250 )mm, 5μ, Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = A. | A |
| 23 | 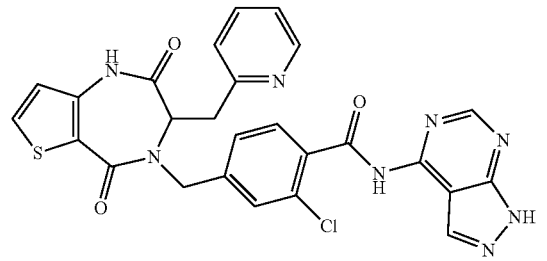<br>2-chloro-4-((2,5-dioxo-3-(pyridin-2-ylmethyl)-1,2,3,5-tetrahydro-4H-thieno[3,2-e][1,4]diazepin-4-yl)methyl)-N-(1H-pyrazolo[3,4-d]pyrimidin-4-yl)benzamide | LCMS (ES) m/z = 559.17 [M + 1]⁺; ¹H NMR (400 MHz, DMSO-d6) δ 2.90-3.10 and 3.50-3.62 (m, 2H), 4.10-5.05 (m, 3H), 6.86 (d, J = 4.8 Hz, 1H), 7.05-7.35 (m, 3H), 7.41 (s, 1H), 7.61 (d, J = 7.2 Hz, 1H), 7.70 (t, J = 7.2 Hz, 1H), 7.90 (d, J = 5.2 Hz, 1H), 8.40-8.50 (m, 2H), 8.63 (s, 1H), 10.90-11.30 (m, 2H); Chiral purity (14:86); Column Name: CHIRALPAK IB (4.6 · 250 )mm, 5μ, Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = C. | A |
| 24 | 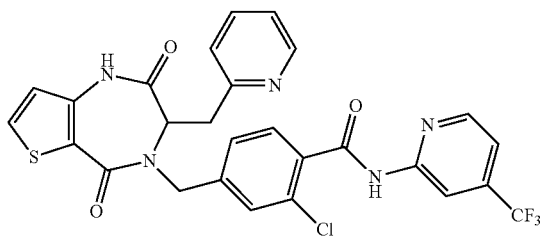<br>2-chloro-4-((2,5-dioxo-3-(pyridin-2-ylmethyl)-1,2,3,5-tetrahydro-4H-thieno[3,2-e][1,4]diazepin-4-yl)methyl)-N-(4-(trifluoromethyl)pyridin-2-yl)benzamide | LCMS (ES) m/z = 586.15 [M + 1]⁺; ¹H NMR (400 MHz, DMSO-d6) acetate salt δ 1.85 (s, 2H, acetate CH$_3$), 2.95-3.15 (m, 2H), 4.10-5.20 (m, 3H), 6.86 (d, J = 5.6 Hz, 1H), 7.05-7.30 (m, 3H), 7.38 (s, 1H), 7.53-7.58 (m, 2H), 7.70 (t, J = 7.2 Hz, 1H), 7.90 (d, J = 5.2 Hz, 1H), 78.40-8.51 (m, 2H), 8.62 (d, J = 5.2 Hz, 1H); Chiral purity (32:68); EC$_{50}$ = B. | A |

| Ex. No. | Structure; IUPAC Name. | LCMS; ¹HNMR; cellular morphology $EC_{50}$ range (μM). | Synthesis Method |
|---|---|---|---|
| 25 | 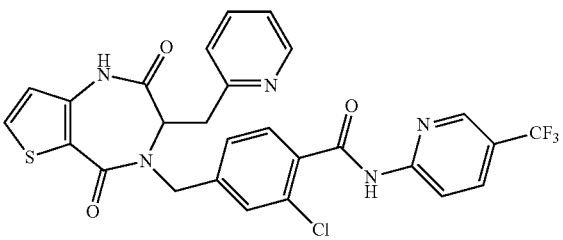<br>2-chloro-4-((2,5-dioxo-3-(pyridin-2-ylmethyl)-1,2,3,5-tetrahydro-4H-thieno[3,2-e][1,4]diazepin-4-yl)methyl)-N-(5-(trifluoromethyl)pyridin-2-yl)benzamide | LCMS (ES) m/z = 586.15 [M + 1]⁺; ¹H NMR (400 MHz, DMSO-d6) δ 2.95-3.12 and 3.50-3.65 (m, 2H), 4.10-5.20 (m, 3H), 6.86 (d, J = 4.8, 1H), 7.05-7.25 (m, 2H), 7.27 (d, J = 7.6 Hz, 1H), 7.38 (s, 1H), 7.53 (d, J = 8.0 Hz, 1H), 7.70 (t, J = 7.2 Hz, 1H), 7.89 (d, J = 5.2 Hz, 1H), 8.22 (dd, J = 9.2 and 2.4 Hz, 1H), 8.35 (d, J = 8.8 Hz, 1H), 8.46 (br s, 1H), 8.73 (s, 1H), 11.12 (br s, 1H), 11.46 (s, 1H); Chiral purity (12:88); Column Name: CHIRALPAK IC (4.6 · 250 )mm, 5μ, Mobile Phase: CO₂/MeOH (60:40), Flow rate: 3.0 mL/min, Flow mode: Isocratic, Column Temperature: 35° C., ABPR Pressure: 1500 psi; $EC_{50}$ = B. | A |
| 26 | 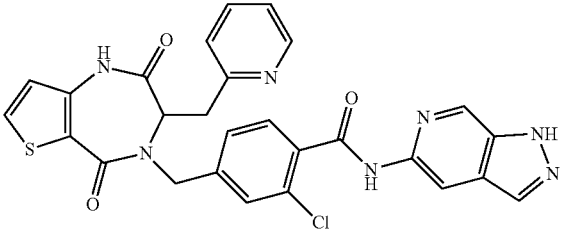<br>2-chloro-4-((2,5-dioxo-3-(pyridin-2-ylmethyl)-1,2,3,5-tetrahydro-4H-thieno[3,2-e][1,4]diazepin-4-yl)methyl)-N-(1H-pyrazolo[3,4-c]pyridin-5-yl)benzamide | LCMS (ES) m/z = 558.17 [M + 1]⁺; ¹H NMR (400 MHz, DMSO-d6) δ 2.90-3.10 and 3.40-3.55 (m, 2H), 3.99 (s, 3H), 4.14-5.10 (m, 3H), 6.86 (d, J = 4.8 Hz, 1H), 7.05-7.30 (m, 3H), 7.37 (s, 1H), 7.51 (d, J = 8.0 Hz, 1H), 7.70 (t, J = 7.2 Hz, 1H), 7.89 (d, J = 5.2 Hz, 1H), 8.09 (s, 1H), 8.40-8.52 (m, 2H), 11.13 (br s, 1H), 11.37 (s, 1H); Chiral purity (31:69) Column Name: CHIRALPAK IB N-5, (4.6 · 250 )mm, 5μ, Mobile Phase: CO₂/0.2% TEA in EtOH (60:40), Flow rate: 3.0 mL/min, Flow mode: Isocratic, Column Temperature: 35° C., ABPR Pressure: 1500 psi; $EC_{50}$ = B. | A |
| 27 | 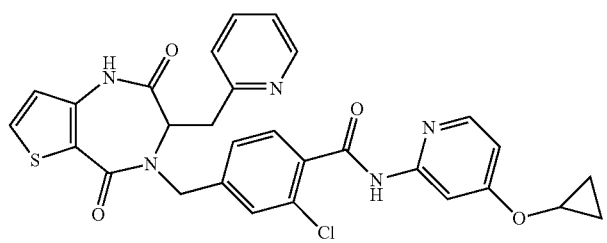<br>2-chloro-N-(4-cyclopropoxypyridin-2-yl)-4-((2,5-dioxo-3-(pyridin-2-ylmethyl)-1,2,3,5-tetrahydro-4H-thieno[3,2-e][1,4]diazepin-4-yl)methyl)benzamide | LCMS (ES) m/z = 574.21 [M + 1]⁺; ¹H NMR (400 MHz, DMSO-d6) δ 0.68-0.73 (m, 2H), 0.80-0.86 (m, 2H), 2.95-3.10 and 3.50-3.65 (m, 2H), 3.92-4.00 (m, 1H), 4.10-5.15 (m, 3H), 6.84-6.70 (m, 2H), 7.05-7.28 (m, 3H), 7.35 (s, 1H), 7.48 (d, J = 7.6 Hz, 1H), 7.70 (t, J = 7.2 Hz, 1H), 7.89 (d, J = 5.6 Hz, 1H), 7.94 (s, 1H), 8.14 (d, J = 5.6 Hz, 1H), 8.46 (br s, 1H), 10.93 (s, 1H), | A |

TABLE 1-continued

| Ex. No. | Structure; IUPAC Name. | LCMS; $^1$HNMR; cellular morphology $EC_{50}$ range (μM). | Synthesis Method |
|---|---|---|---|
| | | 11.13 (br s, 1H); Chiral purity (24.76); Column Name: CHIRALPAK IB N-5(4.6 · 250)mm, 5μ, Mobile Phase: $CO_2$/0.2% TEA in MeOH (60:40), Flow rate: 3.0 mL/min, Flow mode: Isocratic, Column Temperature: 35° C., ABPR Pressure: 1500 psi; $EC_{50}$ = A. | |
| 28 | 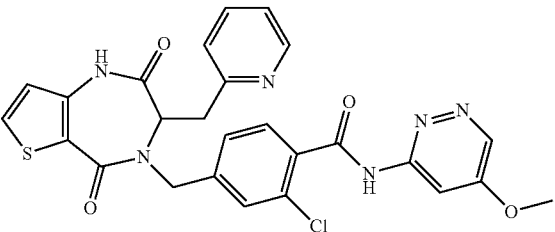<br>2-chloro-4-((2,5-dioxo-3-(pyridin-2-ylmethyl)-1,2,3,5-tetrahydro-4H-thieno[3,2-e][1,4]diazepin-4-yl)methyl)-N-(5-methoxypyridazin-3-yl)benzamide | LCMS (ES); m/z = 549.13 [M + 1]$^+$; $^1$H NMR (400 MHz, DMSO-d6) δ 2.90-3.10 and 3.55-3.65 (m, 2H), 4.10-5.15 (m, 3H), 6.85 (d, J = 4.8 Hz, 1H), 7.05-7.30 (m, 3H), 7.38 (s, 1H), 7.53 (d, J = 8.4 Hz, 1H), 7.70 (t, J = 7.2 Hz, 1H), 7.90 (d, J = 5.6 Hz, 1H), 7.98 (s, 1H), 8.46 (br s, 1H), 8.78 (d, J = 2.4 Hz, 1H), 11.15 (br s, 1H), 11.57 (s, 1H); Chiral purity (20:80); Column Name: CHIRALCEL OJ-H 4.6 · 250)mm, 5μ, Mobile Phase: $CO_2$/MeOH (60:40), Flow rate: 3.0 mL/min, Flow mode: Isocratic, Column Temperature: 35° C., ABPR Pressure: 1500 psi; $EC_{50}$ = C. | A |
| 29 | 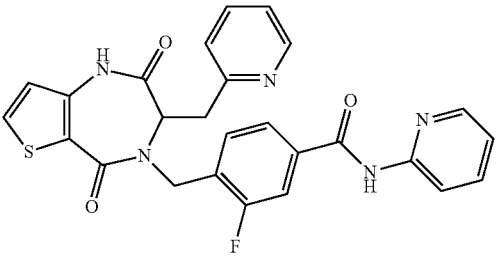<br>4-((2,5-dioxo-3-(pyridin-2-ylmethyl)-1,2,3,5-tetrahydro-4H-thieno[3,2-e][1,4]diazepin-4-yl)methyl)-3-fluoro-N-(pyridin-2-yl)benzamide | LCMS (ES) m/z = 502.19 [M + 1]$^+$; $^1$H NMR (400 MHz, DMSO-d6) δ 3.00-3.15 and 3.40-3.60 (m, 2H), 3.90-5.20 (m, 3H), 6.86 (d, J = 4.8 Hz, 1H), 7.05-7.35 (m, 4H), 7.71 (t, J = 7.2 Hz, 1H), 7.80-7.88 (m, 3H), 7.89 (d, J = 5.2 Hz, 1H), 8.14 (d, J = 8.4 Hz, 1H), 8.38 (d, J = 4.0 Hz, 1H), 8.50 (br s, 1H), 10.84 (s, 1H), 11.09 (br s, 1H); Chiral purity (57:43); Column Name: CHIRALCEL OJ-H (4.6 · 250)mm, 5μ Mobile Phase: $CO_2$/0.2% TEA in MeOH (60:40), Flow rate: 3.0 mL/min, Flow mode: Isocratic, Column Temperature: 35° C., ABPR Pressure: 1500 psi; $EC_{50}$ = B. | A |

| Ex. No. | Structure; IUPAC Name. | LCMS; $^1$HNMR; cellular morphology $EC_{50}$ range (μM). | Synthesis Method |
|---|---|---|---|
| 30 | 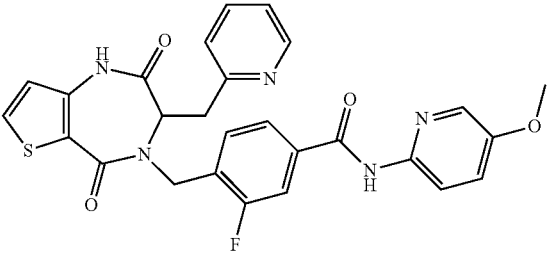<br>4-((2,5-dioxo-3-(pyridin-2-ylmethyl)-1,2,3,5-tetrahydro-4H-thieno[3,2-e][1,4]diazepin-4-yl)methyl)-3-fluoro-N-(5-methoxypyridin-2-yl)benzamide | LCMS (ES) m/z = 532.21 [M + 1]$^+$; $^1$H NMR (400 MHz, DMSO-d6) δ 3.00-3.15 and 3.40-3.60 (m, 2H), 3.83 (s, 3H), 3.90-5.15 (m, 3H), 6.86 (d, J = 5.2 Hz, 1H), 7.05-7.28 (m, 2H), 7.31 (d, J = 8.0 Hz, 1H), 7.47 (dd, J = 9.2 and 3.2 Hz, 1H), 7.71 (t, J = 7.2 Hz, 1H), 7.78-7.85 (m, 2H), 7.89 (d, J = 5.2 Hz, 1H), 8.06 (d, J = 9.2 Hz, 1H), 8.10 (d, J = 2.8 Hz, 1H), 8.50 (br s, 1H), 10.73 (s, 1H), 11.08 (br s, 1H); Chiral purity (80:20); Column Name: CHIRALCEL OJ-H (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; $EC_{50}$ = B. | A |
| 31 | 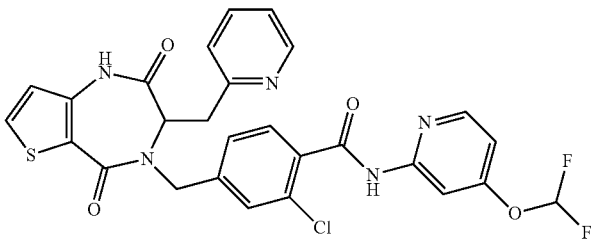<br>2-chloro-N-(4-(difluoromethoxy)pyridin-2-yl)-4-((2,5-dioxo-3-(pyridin-2-ylmethyl)-1,2,3,5-tetrahydro-4H-thieno[3,2-e][1,4]diazepin-4-yl)methyl)benzamide | LCMS (ES) m/z = 584.20 [M + 1]$^+$; $^1$H NMR (400 MHz, DMSO-d6) δ 2.95-3.10 and 3.50-3.65 (m, 2H), 4.10-5.15 (m, 3H), 6.85 (d, J = 5.6 Hz, 1H), 6.98 (dd, J = 9.2 and 2.0 Hz, 1H), 7.05-7.28 (m, 3H), 7.36 (s, 1H), 7.49 (d, J = 8.4 Hz, 1H), 7.51 (t, J = 73.2 Hz, 1H), 7.69 (t, J = 7.2 Hz, 1H), 7.89 (d, J = 5.6 Hz, 1H), 7.98 (s, 1H), 8.32 (d, J = 5.6 Hz, 1H), 8.46 (br s, 1H), 11.14 (br s, 1H), 11.22 (s, 1H); Chiral purity (23.77); Column Name: CHIRALPAK IC (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; $EC_{50}$ = A. | A |

TABLE 1-continued

| Ex. No. | Structure; IUPAC Name. | LCMS; $^1$HNMR; cellular morphology $EC_{50}$ range (μM). | Synthesis Method |
|---|---|---|---|
| 32 | 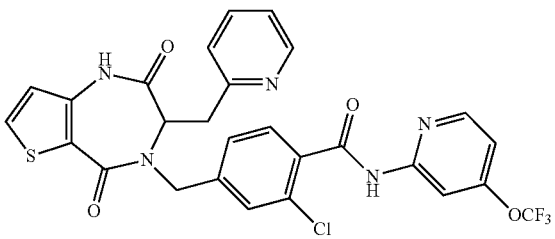  2-chloro-4-((2,5-dioxo-3-(pyridin-2-ylmethyl)-1,2,3,5-tetrahydro-4H-thieno[3,2-e][1,4]diazepin-4-yl)methyl)-N-(4-(trifluoromethoxy)pyridin-2-yl)benzamide | LCMS (ES) m/z = 602.18 [M + 1]$^+$; $^1$H NMR (400 MHz, DMSO-d6) δ 2.95-3.10 and 3.50-3.65 (m, 2H), 4.10-5.15 (m, 3H), 6.85 (d, J = 5.2 Hz, 1H), 7.05-7.30 (m, 4H), 7.37 (s, 1H), 7.52 (d, J = 8.4 Hz, 1H), 7.70 (t, J = 7.2 Hz, 1H), 7.90 (d, J = 5.6 Hz, 1H), 8.17 (s, 1H), 8.40-8.50 (m, 2H), 11.11 (br s, 1H), 11.41 (s, 1H); Chiral purity (22:78); Column Name: CHIRALPAK IC (4.6 × 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi; $EC_{50}$ = A. | A |
| 33 | 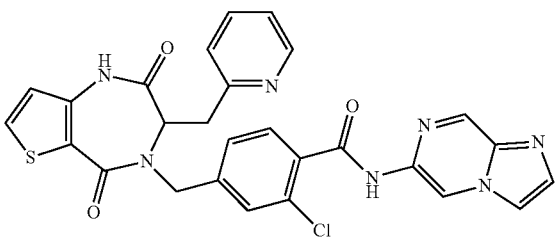  2-chloro-4-((2,5-dioxo-3-(pyridin-2-ylmethyl)-1,2,3,5-tetrahydro-4H-thieno[3,2-e][1,4]diazepin-4-yl)methyl)-N-(imidazo[1,2-a]pyrazin-6-yl)benzamide | LCMS (ES) m/z = 558.20 [M + 1]$^+$; $^1$H NMR (400 MHz, DMSO-d6) δ 2.95-3.10 and 3.50-3.65 (m, 2H), 4.10-5.20 (m, 3H), 6.87 (d, J = 5.6 Hz, 1H), 7.05-7.30 (m, 3H), 7.38 (s, 1H), 7.52 (d, J = 8.0 Hz, 1H), 7.70 (t, J = 8.0 Hz, 1H), 7.81 (s, 1H), 7.90 (d, J = 5.6 Hz, 1H), 8.28 (s, 1H), 8.47 (br s, 1H), 8.94 (s, 1H), 9.43 (s, 1H), 11.00-11.30 (br s, 2H); Chiral purity (21:79) Column Name: CHIRALPAK IB N-5 (4.6 · 250)mm, 5μ Mobile Phase: CO$_2$/0.2% TEA in MeOH (60:40) Flow rate: 3.0 mL/min Flow mode: Isocratic Column Temperature: 35° C. ABPR Pressure: 1500 psi; $EC_{50}$ = B. | A |
| 34 | 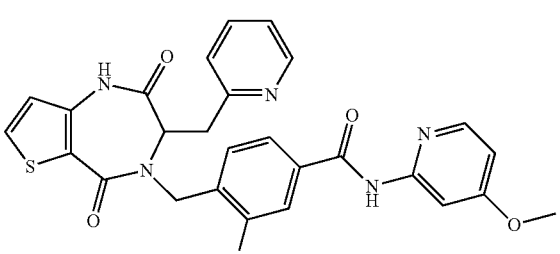  4-((2,5-dioxo-3-(pyridin-2-ylmethyl)-1,2,3,5-tetrahydro-4H-thieno[3,2-e][1,4]diazepin-4-yl)methyl)-3-fluoro-N-(4-methoxypyridin-2-yl)benzamide | LCMS (ES) m/z = 532.21 [M + 1]$^+$; $^1$H NMR (400 MHz, DMSO-d6) δ 3.00-3.15 and 3.40-3.55 (m, 2H), 3.84 (s, 3H), 3.90-5.20 (m, 3H), 6.78 (dd, J = 6.0 and 2.4 Hz, 1H), 6.86 (d, J = 5.2 Hz, 1H), 7.05-7.28 (m, 2H), 7.31 (d, J = 8.0 Hz, 1H), 7.71 (t, J = 7.2 Hz, 1H), 7.78-7.85 (m, 3H), 7.89 (d, J = 5.2 Hz, 1H), 8.19 (d, J = 5.6 Hz, 1H), 8.50 (br s, 1H), 10.82 (s, 1H), 11.08 (br s, 1H); Chiral purity (80:20); Column Name: CHIRALCEL OJ-H (4.6 · 250)mm, 5μ, Mobile Phase: | A |

TABLE 1-continued

| Ex. No. | Structure; IUPAC Name. | LCMS; ¹HNMR; cellular morphology EC$_{50}$ range (μM). | Synthesis Method |
|---|---|---|---|
| | | CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = A. | |
| 35 | 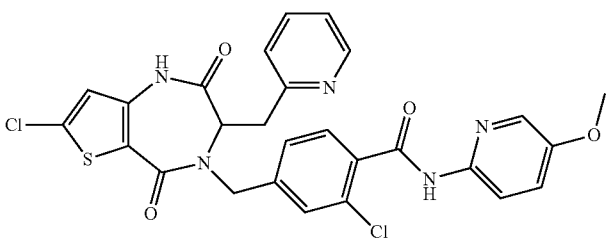<br>2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(5-methoxypyridin-2-yl)benzamide | LCMS (ES) m/z = 582.12 [M + 1]$^+$; ¹H NMR (400 MHz, DMSO-d6) δ 3.00-3.25 (m, 2H), 3.81 (s, 3H), 4.00-4.30 (m, 1H), 4.55-5.15 (m, 2H), 6.89 (s, 1H), 7.15-7.30 (m, 3H), 7.35 (s, 1H), 7.45-7.52 (m, 2H), 7.70 (t, J = 7.6 Hz, 1H), 8.05 (d, J = 2.4 Hz, 1H), 8.07 (d, J = 9.2 Hz, 1H), 8.46 (br s, 1H), 10.83 (s, 1H), 11.20 (br s, 1H); Chiral purity (30:70); Column Name: CHIRALPAK IB (4.6 · 250)mm, 5μ, Mobile Phase: CO2/0.2% TEA in MeOH (60:40), Flow rate: 3.0 mL/min, Flow mode: Isocratic, Column Temperature: 35° C., ABPR Pressure: 1500 psi; EC$_{50}$ = A. | A |
| 36 | 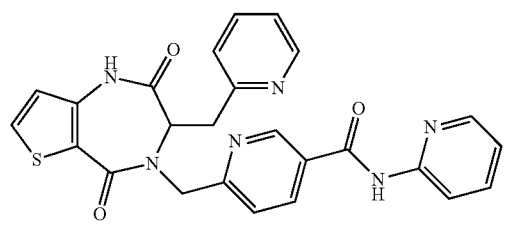<br>6-((2,5-dioxo-3-(pyridin-2-ylmethyl)-1,2,3,5-tetrahydro-4H-thieno[3,2-e][1,4]diazepin-4-yl)methyl)-N-(pyridin-2-yl)nicotinamide | LCMS (ES) m/z = 485.20 [M + 1]$^+$; ¹H NMR (400 MHz, DMSO-d6) δ 3.15-3.25 (m, 2H), 4.45-5.00 (m, 3H), 6.90 (d, J = 4.8 Hz, 1H), 7.15-7.25 (m, 3H), 7.33 (d, J = 8.0 Hz, 1H), 7.68 (t, J = 7.2 Hz, 1H), 7.80-7.86 (m, 2H), 8.13 (d, J = 8.4 Hz, 1H), 8.27 (dd, J = 8.4 and 2.4 Hz, 1H), 8.37 (d, J = 6.0 Hz, 1H), 8.46 (d, J = 4.4 Hz, 1H), 9.04 (d, J = 2.0 Hz, 1H), 10.68 (s, 1H), 10.81 (s, 1H); Chiral purity (14:86); Column Name: CHIRALPAK IB (4.6 · 250)mm, 5μ Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = C. | A |

TABLE 1-continued

| Ex. No. | Structure; IUPAC Name. | LCMS; ¹HNMR; cellular morphology EC$_{50}$ range (μM). | Synthesis Method |
|---|---|---|---|
| 37 | 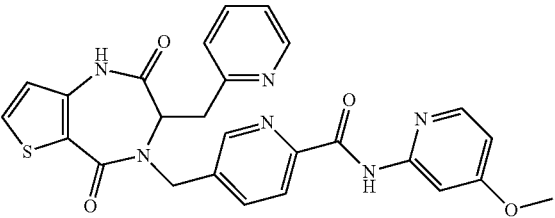<br>5-((2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)picolinamide | LCMS (ES) m/z = 515.23 [M + 1]$^+$; $^1$H NMR (400 MHz, DMSO-d6) δ 2.90-3.15 and 3.50-3.65 (m, 2H), 4.05-5.15 (m, 3H), 6.80 (dd, J = 5.6 and 2.4 Hz, 1H), 6.86 (d, J = 4.4 Hz, 1H), 7.05-7.25 (m, 2H), 7.66 (t, J = 6.8 Hz, 1H), 7.85-7.93 (m, 3H), 8.08 (d, J = 8.0 Hz, 1H), 8.20 (d, J = 6.0 Hz, 1H), 8.40 (br s, 1H), 8.60 (s, 1H), 10.29 (s, 1H), 1.13 (br s, 1H); EC$_{50}$ = C. | A |
| 38 | 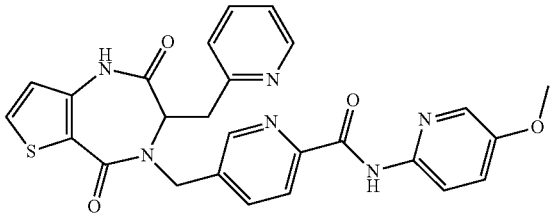<br>5-((2,5-dioxo-3-(pyridin-2-ylmethyl)-1,2,3,5-tetrahydro-4H-thieno[3,2-e][1,4]diazepin-4-yl)methyl)-N-(5-methoxypyridin-2-yl)picolinamide | LCMS (ES) m/z = 515.20 [M + 1]$^+$; $^1$H NMR (400 MHz, DMSO-d6) δ 2.95-3.10 and 3.50-3.62 (m, 2H), 3.83 (s, 3H), 4.25-5.25 (m, 3H), 6.86 (d, J = 4.8 Hz, 1H), 7.05-7.30 (m, 2H), 7.53 (dd, J = 9.2 and 2.8 Hz, 1H), 7.66 (t, J = 7.2 Hz, 1H), 7.86 (d, J = 8.0 Hz, 1H), 7.90 (d, J = 5.2 Hz, 1H), 8.07 (d, J = 8.4 Hz, 1H), 8.10 (d, J = 2.8 Hz, 1H), 8.18 (d, J = 8.8 Hz, 1H), 8.42 (br s, 1H), 8.59 (s, 1H), 10.27 (s, 1H), 11.12 (br s, 1H); Chiral purity (35:65); Column Name: CHIRALPAK IB N-5 (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = C. | A |
| 39 | 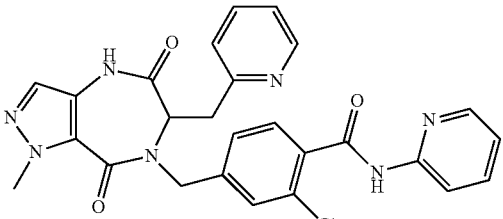<br>2-chloro-4-((1-methyl-5,8-dioxo-6-(pyiridn-2-ylmethyl)-4,5,6,8-tetrahydropyrazolo[4,3-e][1,4]diazepin-7(1H)-yl)methyl)-N-(pyridin-2-yl)benzamide | LCMS (ES) m/z = 516.24 [M + 1]$^+$; $^1$H NMR (400 MHz, DMSO-d6) δ 2.90-3.20 and 3.58-3.67 (m, 2H), 4.04 and 4.06 (2 × s, 3H), 4.60-5.15 (m, 3H), 7.14-7.35 (m, 5H), 7.44 (s, 1H), 7.49 (t, J = 5.6 Hz, 1H), 7.65-7.73 (m, 1H), 7.80-7.86 (m, 1H), 8.14 (d, J = 8.4 Hz, 1H), 8.33 (d, J = 5.6 Hz, 1H), 8.36-8.50 (m, 1H), 10.48 and 10.66 (2 × s, 1H), 10.96 (s, 1H); Chiral purity (42:57); Column Name: LUX Amylose-1 (4.6 · 250)mm, 5μ Mobile Phase: CO$_2$/Ethanol (60:40), Flow rate: 3.0 mL/min, Flow mode: Isocratic, Column Temperature: 35° C., ABPR Pressure: | A |

TABLE 1-continued

| Ex. No. | Structure; IUPAC Name. | LCMS; $^1$HNMR; cellular morphology $EC_{50}$ range (μM). | Synthesis Method |
|---|---|---|---|
| 40 | 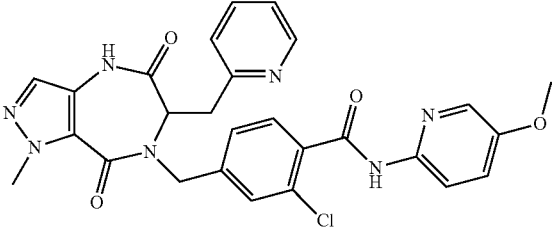<br>2-chloro-N-(5-methoxypyridin-2-yl)-4-((1-methyl-5,8-dioxo-6-(pyridin-2-ylmethyl)-4,5,6,8-tetrahydropyrazolo[4,3-e][1,4]diazepin-7(1H)-yl)methyl)benzamide | 1500 psi; $EC_{50}$ = B.<br><br>LCMS (ES) m/z = 546.26 [M + 1]+; $^1$H NMR (400 MHz, DMSO-d6) δ 2.90-3.20 and 3.58-3.67 (m, 2H), 3.81 (s, 3H), 4.04 and 4.06 (2 × s, 3H), 4.60-5.15 (m, 3H), 7.15-7.28 (m, 2H), 7.30-7.36 (m, 2H), 7.43-7.50 (m, 2H), 7.65-7.73 (m, 1H), 8.05 (d, J = 2.8 Hz, 1H), 8.08 (d, J = 8.8 Hz, 1H), 8.34-8.50 (m, 1H), 10.48 and 10.66 (2 × s, 1H), 10.82 and 10.83 (2 × s, 1H); Chiral purity (41.59); Column Name: CHIRALPAK IB N-5 (4.6 · 250)mm, 5μ, Mobile Phase: $CO_2$/0.2% TEA in MeOH (60:40), Flow rate: 3.0 mL/min, Flow mode: Isocratic, Column Temperature: 35° C., ABPR Pressure: 1500 psi; $EC_{50}$ = B. | A |
| 41 | 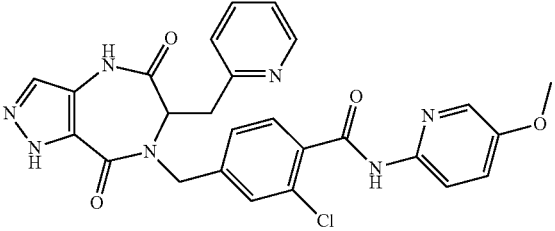<br>2-chloro-4-((5,8-dioxo-6-(pyridin-2-ylmethyl)-4,5,6,8-tetrahydropyrazolo[4,3-e][1,4]diazepin-7(1H)-yl)methyl)-N-(5-methoxypyridin-2-yl)benzamide | LCMS (ES) m/z = 532.28 [M + 1]+; $^1$H NMR (400 MHz, DMSO-d6) δ 2.85-3.10 and 3.50-3.65 (m, 2H), 3.81 (s, 3H), 4.00-5.15 (m, 3H), 6.65-7.55 (m, 8H), 7.60-7.75 (m, 1H), 8.00-8.50 (m, 2H), 10.25-10.90 (m, 2H), 13.50-13.85 (m, 1H); Chiral purity: (22:78); Column Name: CHIRALPAK IB (4.6 · 250)mm, 5μ, Mobile Phase: $CO_2$/0.2% TEA in MeOH (60:40), Flow rate: 3.0 mL/min, Flow mode: Isocratic, Column Temperature: 35° C., ABPR Pressure: 1500 psi; $EC_{50}$ = B. | A |
| 42 | 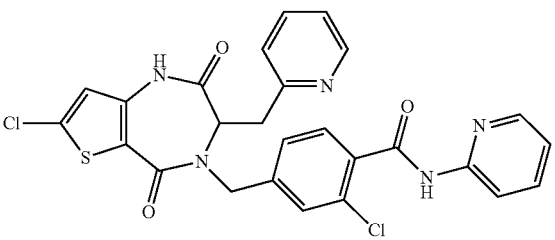<br>2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(pyiridn-2-yl)benzamide | LCMS (ES) m/z = 552.16 [M + 1]+; $^1$H NMR (400 MHz, DMSO-d6) δ 3.00-3.20 and 3.50-3.65 (m, 2H), 4.00-5.00 (m, 3H), 6.89 (s, 1H), 7.14-7.18 (m, 1H), 7.20-7.30 (m, 3H), 7.36 (s, 1H), 7.49 (d, J = 7.6 Hz, 1H), 7.71 (t, J = 6.8 Hz, 1H), 7.83 (t, J = 7.2 Hz, 1H), 8.14 (d, J = 8.0 Hz, 1H), 8.33 (d, J = 4.0 Hz, 1H), 8.46 (br s, 1H), 10.95 (s, 1H), 11.13 (br s, 1H); $EC_{50}$ = A. | A |

TABLE 1-continued

| Ex. No. | Structure; IUPAC Name. | LCMS; ¹HNMR; cellular morphology EC$_{50}$ range (μM). | Synthesis Method |
|---|---|---|---|
| 43 | 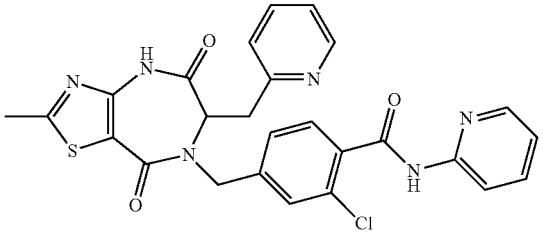<br>2-chloro-4-((2-methyl-5,8-dioxo-6-(pyridin-2-ylmethyl)-4,5,6,8-tetrahydro-7H-thiazolo[4,5-e][1,4]diazepin-7-yl)methyl)-N-(pyridin-2-yl)benzamide | LCMS (ES) m/z = 533.19 [M + 1]$^+$; $^1$H NMR (400 MHz, DMSO-d6, vt NMR) δ 2.66 (s, 3H), 2.95-3.15 (m, 2H), 4.00-5.20 (m, 3H), 7.15 (dd, J = 8.0 and 5.2 Hz, 1H), 7.18-7.28 (m, 3H), 7.35 (s, 1H), 7.48 (d, J = 8.0 Hz, 1H), 7.69 (t, J = 7.2 Hz, 1H), 7.82 (t, J = 7.6 Hz, 1H), 8.14 (d, J = 8.8 Hz, 1H), 8.32 (d, J = 4.4 Hz, 1H), 8.46 (d, J = 4.0 Hz, 1H), 9.23 (s, 1H), 10.96 (s, 1), 11.60 (br s, 1H); Chiral purity (2:98); Column Name: CHIRALPAK IB (4.6 · 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = D. | A |
| 44 | 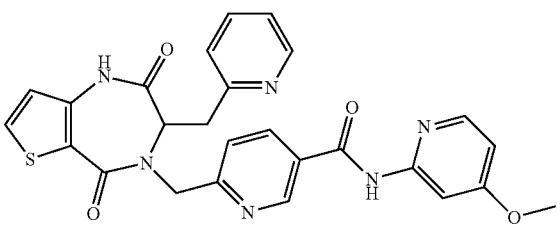<br>6-((2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)nicotinamide | LCMS (ES) m/z = 515.24 [M + 1]$^+$; $^1$H NMR (400 MHz, DMSO-d6) δ 3.00-3.20 and 3.50-3.65 (m, 2H), 3.85 (s, 3H), 4.10-5.20 (m, 3H), 6.79 (dd, J = 6.0 and 2.4 Hz, 1H), 6.87 (d, J = 5.2 Hz, 1H), 7.10-7.20 (m, 2H), 7.32 (d, J = 8.0 Hz, 1H), 7.70 (t, J = 7.2 Hz, 1H), 7.82 (d, J = 2.0 Hz, 1H), 7.89 (d, J = 5.2 Hz, 1H), 8.19 (d, J = 6.0 Hz, 1H), 8.28 (dd, J = 8.4 and 2.4 Hz, 1H), 8.46 (br s, 1H), 9.02 (d, J = 2.0 Hz, 1H), 10.89 (s, 1H), 11.06 (br s, 1H); Chiral purity (1:1); Column Name: CHIRALCEL OJH (4.6 · 150)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = B. | A |

TABLE 1-continued

| Ex. No. | Structure; IUPAC Name. | LCMS; ¹HNMR; cellular morphology $EC_{50}$ range (μM). | Synthesis Method |
|---|---|---|---|
| 45 | 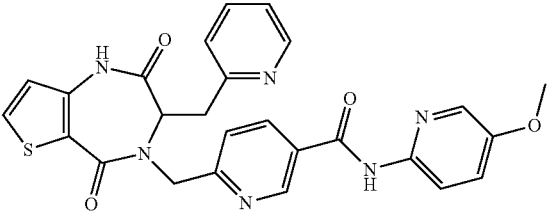<br>6-((2,5-dioxo-3-(pyridin-2-ylmethyl)-1,2,3,5-tetrahydro-4H-thieno[3,2-e][1,4]diazepin-4-yl)methyl)-N-(5-methoxypyiridn-2-yl)nicotinamide | LCMS (ES) m/z = 515.23 [M + 1]⁺; ¹H NMR (400 MHz, DMSO-d6) δ 3.00-3.20 (m, 2H), 3.82 (s, 3H), 4.10-5.20 (m, 3H), 6.86 (d, J = 5.2 Hz, 1H), 7.05-7.28 (m, 2H), 7.31 (d, J = 8.0 Hz, 1H), 7.49 (dd, J = 9.2 and 3.2 Hz, 1H), 7.69 (t, J = 7.2 Hz, 1H), 7.88 (d, J = 5.2 Hz, 1H), 9.06-8.12 (m, 2H), 8.25 (dd, J = 8.0 and 2.0 Hz, 1H), 8.45 (br s, 1H), 9.01 (d, J = 2.0 Hz, 1H), 10.89 (s, 1H), 11.06 (br s, 1H); Chiral purity (1:1); Column Name: CHIRALCEL OJH (4.6 · 150)mm, 5μ, Mobile Phase: $CO_2$/0.2% TEA in MeOH (60:40), Flow rate: 3.0 mL/min, Flow mode: Isocratic, Column Temperature: 35° C., ABPR Pressure: 1500 psi; $EC_{50}$ = C. | A |
| 46 | 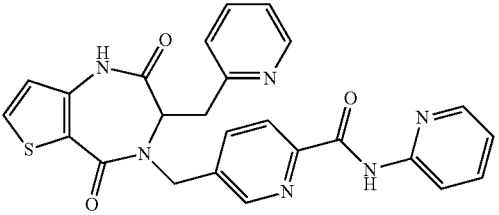<br>5-((2,5-dioxo-3-(pyridin-2-ylmethyl)-1,2,3,5-tetrahydro-4H-thieno[3,2-e][1,4]diazepin-4-yl)methyl)-N-(pyridin-2-yl)picolinamide | LCMS (ES) m/z = 485.22 [M + 1]⁺; ¹H NMR (400 MHz, DMSO-d6) δ 2.90-3.10 and 3.50-3.65 (m, 2H), 4.25-4.20 (m, 3H), 6.86 (d, J = 5.2 Hz, 1H), 7.05-7.24 (m, 3H), 7.66 (t, J = 7.2 Hz, 1H), 7.87-7.95 (m, 3H), 8.09 (d, J = 8.0 Hz, 1H), 8.25 (d, J = 8.4 Hz, 1H), 8.39 (dd, J = 4.8 and 1.2 Hz, 1H), 8.42 (br s, 1H), 8.61 (s, 1H), 10.35 (s, 1H), 11.12 (s, 1H); Chiral purity (1:1); Column Name: CHIRALCEL OJH (4.6 · 150)mm, 5μ Mobile Phase: $CO_2$/0.2% TEA in MeOH (60:40), Flow rate: 3.0 mL/min, Flow mode: Isocratic, Column Temperature: 35° C., ABPR Pressure: 1500 psi; $EC_{50}$ = C. | A |

TABLE 1-continued

| Ex. No. | Structure; IUPAC Name. | LCMS; ¹HNMR; cellular morphology $EC_{50}$ range (μM). | Synthesis Method |
|---|---|---|---|
| 47 | 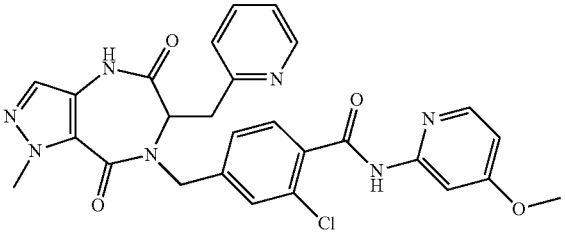2-chloro-N-(4-methoxypyridin-2-yl)-4-((1-methyl-5,8-dioxo-6-(pyridin-2-ylmethyl)-4,5,6,8-tetrahydropyrazolo[4,3-e][1,4]diazepin-7(1H)-yl)methyl)benzamide | LCMS (ES) m/z = 546.10 [M + 1]⁺; ¹H NMR (400 MHz, DMSO-d6) δ 2.90-3.20 and 3.58-3.67 (m, 2H), 4.04 and 4.06 (2 × s, 3H), 4.60-5.15 (m, 3H), 6.76 (dd, J = 5.6 and 2.0 Hz, 1H), 7.15-7.36 (m, 4H), 7.40-7.50 (m, 2H), 7.65-7.73 (m, 1H), 7.80-7.86 (m, 1H), 7.79 (s, 1H), 8.13 (d, J = 5.6 Hz, 1H), 8.36-8.50 (m, 1H), 10.48 and 10.66 (2 × s, 1H), 10.96 (s, 1H); $EC_{50}$ = A. | B |
| 48 | 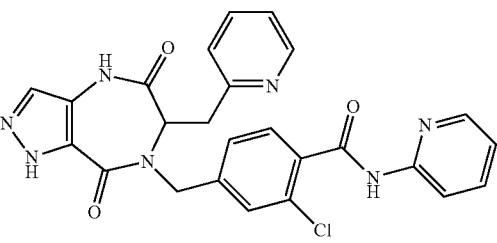2-chloro-4-((5,8-dioxo-6-(pyridin-2-ylmethyl)-4,5,6,8-tetrahydropyrazolo[4,3-e][1,4]diazepin-7(1H)-yl)methyl)-N-(pyridin-2-yl)benzamide | LCMS (ES) m/z = 502.19 [M + 1]⁺; ¹H NMR (400 MHz, DMSO-d6) δ 2.85-3.10, 3.12-3.25 and 3.50-3.65 (m, 2H), 4.10-5.15 (m, 3H), 7.05-7.34 (m, 4H), 7.37 (s, 1H), 7.40-7.48 (m, 1H), 7.49 (d, J = 8.0 Hz, 1H), 7.68 (t, J = 8.0 Hz, 1H), 7.83 (t, J = 8.4 Hz, 1H), 8.14 (d, J = 8.4 Hz, 1H), 8.33 (d, J = 3.6 Hz, 1H), 8.35-8.50 (m, 1H), 10.40-10.70 (m, 1H), 10.96 (s, 1H), 13.69 (br s, 1H); Chiral purity (24:76); Column Name: CHIRALPAK IB N-5 (4.6 · 250)mm, 5μ, Mobile Phase: CO2/0.2% TEA in MeOH (60:40), Flow rate: 3.0 mL/min, Flow mode: Isocratic, Column Temperature: 35° C., ABPR Pressure: 1500 psi; $EC_{50}$ = D. | A |
| 49 | 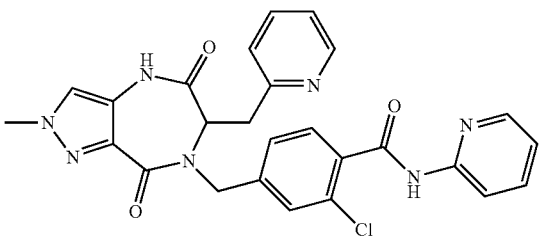2-chloro-4-((2-methyl-5,8-dioxo-6-(pyridin-2-ylmethyl)-2,5,6,8-tetrahydropyrazolo[4,3-e][1,4]diazepin-7(4H)-yl)methyl)-N-(pyridin-2-yl)benzamide | LCMS (ES) m/z = 516.24 [M + 1]⁺; ¹H NMR (400 MHz, DMSO-d6) δ 2.85-3.03, 3.15-3.25 and 3.50-3.60 (m, 2H), 3.93 (s, 3H), 4.15-5.15 (m, 3H), 7.00-7.30 (m, 4H), 7.34 (s, 1H), 7.48 (d, J = 7.2 Hz, 1H), 7.63-7.73 (m, 2H), 7.83 (t, J = 8.4 Hz, 1H), 8.14 (d, J = 7.6 Hz, 1H), 8.33 (d, J = 3.6 Hz, 1H), 8.35-8.50 (m, 1H), 10.33 and 10.49 (2 × s, 1H), 10.94 and 10.97 (2 × s, 1H); Chiral purity (30:70); Column Name: CHIRALPAK IB (4.6 · 150)mm, 5μ, Mobile Phase: CO₂/0.2% TEA in MeOH (60:40), Flow rate: 3.0 mL/min, Flow mode: Isocratic, | A |

TABLE 1-continued

| Ex. No. | Structure; IUPAC Name. | LCMS; ¹HNMR; cellular morphology EC$_{50}$ range (μM). | Synthesis Method |
| --- | --- | --- | --- |
| | | Column Temperature: 35° C., ABPR Pressure: 1500 psi; EC$_{50}$ = C. | |
| 50 | 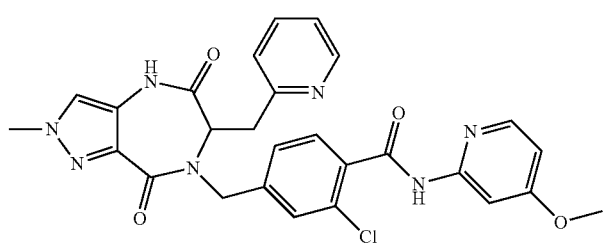<br>2-chloro-N-(4-methoxypyridin-2-yl)-4-((2-methyl-5,8-dioxo-6-(pyridin-2-ylmethyl)-2,5,6,8-tetrahydropyrazolo[4,3-e][1,4]diazepin-7(4H)-yl)methyl)benzamide | LCMS (ES) m/z = 546.23 [M + 1]⁺; ¹H NMR (400 MHz, DMSO-d6) δ 2.85-3.03, 3.15-3.25 and 3.50-3.60 (m, 2H), 3.84 (s, 3H), 3.93 (s, 3H), 4.15-5.15 (m, 3H), 6.76 (dd, J = 5.6 and 2.0 Hz, 1H), 7.00-7.30 (m, 3H), 7.33 (s, 1H), 7.48 (d, J = 7.2 Hz, 1H), 7.60-7.73 (m, 2H), 7.79 (s, 1H), 8.13 (d, J = 6.0 Hz, 1H), 8.35-8.50 (m, 1H), 10.33 and 10.49 (2 × s, 1H), 10.90 and 10.94 (2 × s, 1H); Chiral purity (25:75); Column Name: CHIRALPAK IB N-5 (4.6 · 150)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = B. | A |
| 51 | 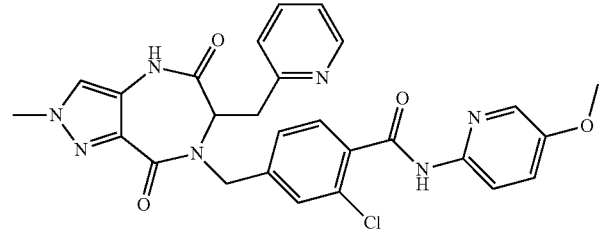<br>2-chloro-N-(5-methoxypyridin-2-yl)-4-((2-methyl-5,8-dioxo-6-(pyridin-2-ylmethyl)-2,5,6,8-tetrahydropyrazolo[4,3-e][1,4]diazepin-7(4H)-yl)methyl)benzamide | LCMS (ES) m/z = 546.26 [M + 1]⁺; ¹H NMR (400 MHz, DMSO-d6) δ 2.85-3.03, 3.15-3.25 and 3.50-3.60 (m, 2H), 3.81 (s, 3H), 3.93 (s, 3H), 4.15-5.15 (m, 3H), 7.00-7.30 (m, 3H), 7.33 (s, 1H), 7.45-7.50 (m, 2H), 7.60-7.73 (m, 2H), 8.04 (d, J = 2.4 Hz, 1H), 8.08 (d, J = 8.8 Hz, 1H), 8.35-8.50 (m, 1H), 10.33 and 10.49 (2 × s, 1H), 10.80 and 10.93 (2 × s, 1H); Chiral purity (38:62); Column Name: CHIRALPAK IB N-5 (4.6 · 150)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = C. | A |

TABLE 1-continued

| Ex. No. | Structure; IUPAC Name. | LCMS; $^1$HNMR; cellular morphology $EC_{50}$ range (μM). | Synthesis Method |
|---|---|---|---|
| 52 | 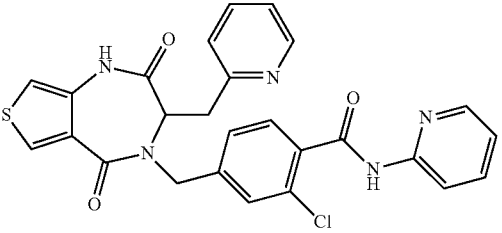<br>2-chloro-4-((2,5-dioxo-3-(pyridin-2-ylmethyl)-2,3-dihydro-1H-thieno[3,4-e][1,4]diazepin-4(5H)-yl)methyl)-N-(pyridin-2-yl)benzamide | LCMS (ES) m/z = 518.19 [M + 1]$^+$; $^1$H NMR (400 MHz, DMSO-d6) δ 2.80-3.12, 3.12-3.22 and 3.50-3.62 (m, 2H), 4.15-5.20 (m, 3H), 7.00-7.20 (m, 3H), 7.22-7.42 (m, 3H), 7.48 (d, J = 8.0 Hz, 1H), 7.63-7.72 (m, 1H), 7.83 (t, J = 8.4 Hz, 1H), 8.14 (d, J = 8.4 Hz, 1H), 8.26 (d, J = 3.6 Hz, 1H), 8.33 (d, J = 3.6 Hz, 1H), 8.35-8.50 (m, 1H), 10.54 and 10.72 (2 × s, 1H), 10.96 (s, 1H). Chiral purity (13:87); Column Name: CHIRALPAK IB (4.6 · 250)mm, 5μ, Mobile Phase: $CO_2$/0.2% TEA in MeOH (60:40), Flow rate: 3.0 mL/min, Flow mode: Isocratic, Column Temperature: 35° C., ABPR Pressure: 1500 psi; $EC_{50}$ = B. | A |
| 53 | 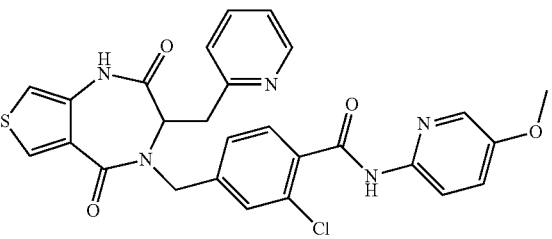<br>2-chloro-4-((2,5-dioxo-3-(pyridin-2-ylmethyl)-2,3-dihydro-1H-thieno[3,4-e][1,4]diazepin-4(5H)-yl)methyl)-N-(5-methoxypyridin-2-yl)benzamide | LCMS (ES) m/z = 548.22 [M + 1]$^+$; $^1$H NMR (400 MHz, DMSO-d6) δ 2.80-3.02, 3.12-3.22 and 3.50-3.62 (m, 2H), 3.81 (s, 3H), 4.15-5.15 (m, 3H), 7.03 (d, J = 4.0 Hz, 1H), 7.15-7.32 (m, 3H), 7.33-7.39 (m, 1H), 7.45-7.52 (m, 2H), 7.63-7.72 (m, 1H), 8.05 (d, J = 2.8 Hz, 1H), 8.08 (d, J = 9.2 Hz, 1H), 8.26 (d, J = 3.6 Hz, 1H), 8.35-8.50 (m, 1H), 10.54 and 10.72 (2 × s, 1H), 10.81 and 10.83 (2 × s, 1H); Chiral purity (14:86); Column Name: CHIRALPAK IB (4.6 · 250)mm, 5μ, Mobile Phase: $CO_2$/MeOH (60:40), Flow rate: 3.0 mL/min, Flow mode: Isocratic, Column Temperature: 35° C., ABPR Pressure: 1500 psi; $EC_{50}$ = A. | A |

| Ex. No. | Structure; IUPAC Name. | LCMS; $^1$HNMR; cellular morphology $EC_{50}$ range (μM). | Synthesis Method |
|---|---|---|---|
| 54 | 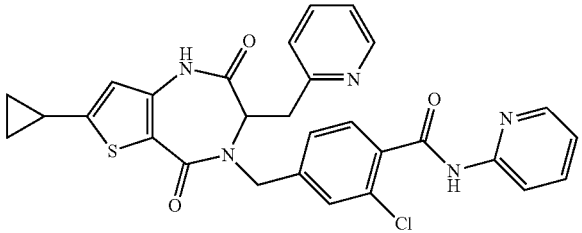<br>2-chloro-4-((7-cyclopropyl-2,5-dioxo-3-(pyridin-2-ylmethyl)-1,2,3,5-tetrahydro-4H-thieno[3,2-e][1,4]diazepin-4-yl)methyl)-N-(pyridin-2-yl)benzamide | LCMS (ES) m/z = 558.21 [M + 1]$^+$; $^1$H NMR (400 MHz, DMSO-d6) δ 0.80-0.87 (m, 2H), 1.08-1.15 (m, 2H), 2.18-2.26 (m, 1H), 2.95-3.15 and 3.45-3.60 (m, 2H), 4.05-5.15 (m, 3H), 6.59 (br s, 1H), 7.05-7.36 (m, 4H), 7.33 (s, 1H), 7.48 (d, J = 8.0 Hz, 1H), 7.70 (t, J = 7.2 Hz, 1H), 7.82 (t, J = 7.2 Hz, 1H), 8.14 (d, J = 8.4 Hz, 1H), 8.32 (d, J = 3.6 Hz, 1H), 8.46 (br s, 1H), 10.90-11.10 (m, 2H); Chiral purity (41:59); Column Name: CHIRALPAK IB (4.6 · 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = A. | A |
| 55 | 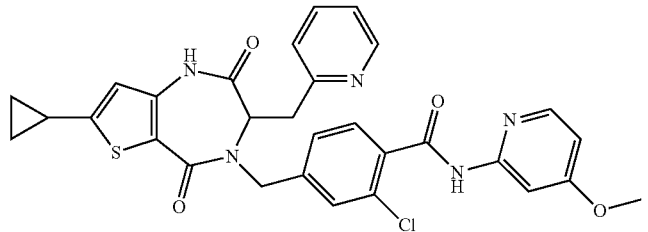<br>2-chloro-4-((7-cyclopropyl-2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)benzamide | LCMS (ES) m/z = 588.26 [M + 1]$^+$; $^1$H NMR (400 MHz, DMSO-d6) δ 0.70-0.80 (m, 2H), 1.08-1.15 (m, 2H), 2.18-2.26 (m, 1H), 2.95-3.12 and 3.45-3.55 (m, 2H), 3.84 (s, 3H), 4.05-5.20 (m, 3H), 6.59 (br s, 1H), 6.76 (dd, J = 6.0 Hz, 1H), 7.05-7.27 (m, 3H), 7.32 (s, 1H), 7.46 (d, J = 8.0 Hz, 1H), 7.70 (t, J = 7.2 Hz, 1H), 7.79 (s, 1H), 8.13 (d, J = 6.0 Hz, 1H), 8.44 (br s, 1H), 10.92 (s, 1H), 11.04 (br s, 1H); Chiral purity (42:58); Column Name: CHIRALPAK IB (4.6 · 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = A. | A |
| 56 | 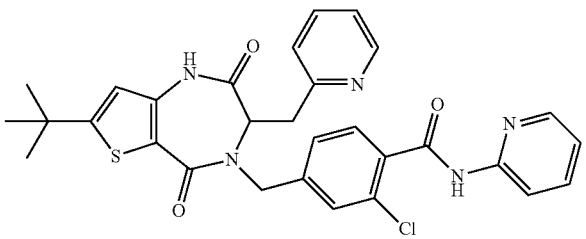<br>4-((7-(tert-butyl)-2,5-dioxo-3-(pyridin-2-ylmethyl)-1,2,3,5-tetrahydro-4H-thieno[3,2-e][1,4]diazepin-4-yl)methyl)-2-chloro-N-(pyridin-2-yl)benzamide | LCMS (ES) m/z = 574.24 [M + 1]$^+$; $^1$H NMR (400 MHz, DMSO-d6) δ 1.36 (s, 9H), 2.96-3.15 and 34.5-3.55 (m, 2H), 4.00-5.20 (m, 3H), 6.65 (s, 1H), 7.05-7.26 (m, 4H), 7.33 (s, 1H), 7.46 (d, J = 8.0 Hz, 1H), 7.71 (t, J = 8.0 Hz, 1H), 7.83 (t, J = 7.6 Hz, 1H), 8.14 (d, J = 8.2 Hz, 1H), 8.33 (d, J = 3.6 Hz, 1H), 8.46 (br s, 1H), 10.96 (s, 1H), 11.04 (br s, 1H); Chiral | A |

TABLE 1-continued

| Ex. No. | Structure; IUPAC Name. | LCMS; ¹HNMR; cellular morphology EC$_{50}$ range (μM). | Synthesis Method |
|---|---|---|---|
| | | purity (43:57); Column Name: CHIRALPAK IBN-5 (4.6 · 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi: EC$_{50}$ = D. | |
| 57 | 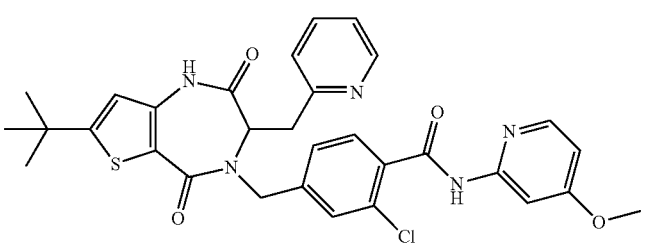<br>4-((7-(tert-butyl)-2,5-dioxo-3-(pyridin-2-ylmethyl)-1,2,3,5-tetrahydro-4H-thieno[3,2-e][1,4]diazepin-4-yl)methyl)-2-chloro-N-(4-methoxypyridin-2-yl)benzamide | LCMS (ES) m/z = 604.26 [M + 1]⁺; ¹H NMR (400 MHz, DMSO-d6) δ 1.38 (s, 9H), 2.96-3.15 and 3.45-3.65 (m, 2H), 3.84 (s, 3H), 4.00-5.15 (m, 3H), 6.65 (s, 1H), 6.76 (dd, J = 5.6 and 2.4 Hz, 1H), 7.05-7.28 (m, 3H), 7.33 (s, 1H), 7.46 (d, J = 8.0 Hz, 1H), 7.70 (t, J = 7.6 Hz, 1H), 7.79 (s, 1H), 8.13 (d, J = 5.6 Hz, 1H), 8.46 (br s, 1H), 10.92 (s, 1H), 11.04 (br s, 1H); Chiral purity (42:58); Column Name: CHIRALPAK IBN-5 (4.6 · 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi: EC$_{50}$ = B. | A |
| 58 | 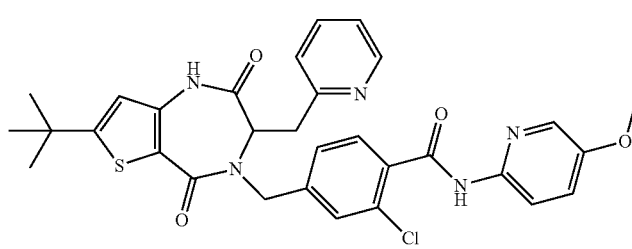<br>4-((7-(tert-butyl)-2,5-dioxo-3-(pyridin-2-ylmethyl)-1,2,3,5-tetrahydro-4H-thieno[3,2-e][1,4]diazepin-4-yl)methyl)-2-chloro-N-(5-methoxypyridin-2-yl)benzamide | LCMS (ES) m/z = 604.26 [M + 1]⁺; ¹H NMR (400 MHz, DMSO-d6) δ 1.36 (s, 9H), 2.96-3.15 and 3.45-3.65 (m, 2H), 3.81 (s, 3H), 4.00-5.15 (m, 3H), 6.65 (s, 1H), 7.05-7.28 (m, 3H), 7.32 (s, 1H), 7.43-7.50 (m, 2H), 7.71 (t, J = 7.6 Hz, 1H), 8.04 (d, J = 2.8 Hz, 1H), 8.07 (d, J = 9.2 Hz, 1H), 8.46 (br s, 1H), 10.82 (s, 1H), 11.03 (br s, 1H); Chiral purity (43:57); Column Name: CHIRALPAK IB (4.6 · 250)mm, 5μ, Mobile Phase: CO$_2$/0.2% TEA in MeOH (80:20), Flow rate: 3.0 mL/min, Flow mode: Isocratic, Column Temperature: 35° C., ABPR Pressure: 1500 psi: EC$_{50}$ = B. | A |

TABLE 1-continued

| Ex. No. | Structure; IUPAC Name. | LCMS; ¹HNMR; cellular morphology EC$_{50}$ range (μM). | Synthesis Method |
|---|---|---|---|
| 59 | 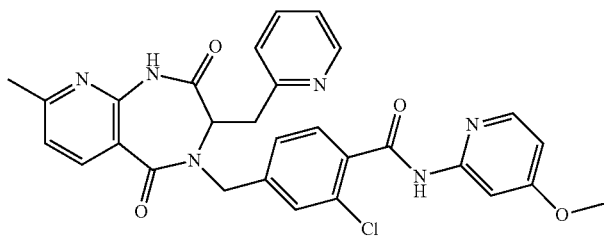<br>2-chloro-N-(4-methoxypyridin-2-yl)-4-((8-methyl-2,5-dioxo-3-(pyridin-2-ylmethyl)-1,2,3,5-tetrahydro-4H-pyrido[2,3-e][1,4]diazepin-4-yl)methyl)benzamide | LCMS (ES) m/z = 557.26 [M + 1]$^+$; $^1$H NMR (400 MHz, DMSO-d6) δ 2.85-3.00, 3.15-3.25 and 3.55-3.65 (m, 2H), 3.84 (s, 3H), 4.25-5.05 (m, 3H), 6.76 (dd, J = 6.0 and 2.8 Hz, 1H), 7.03-7.37 (m, 4H), 7.40 (s, 1H), 7.46 (d, J = 8.0 Hz, 1H), 7.63-7.70 (m, 1H), 7.79 (s, 1H), 8.06-8.20 (m, 2H), 8.35-8.47 (m, 1H), 10.85-11.00 (m, 2H); Chiral purity (59:41); Column Name: CHIRALPAK OJH (4.6 · 25)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = C. | C |
| 60 | 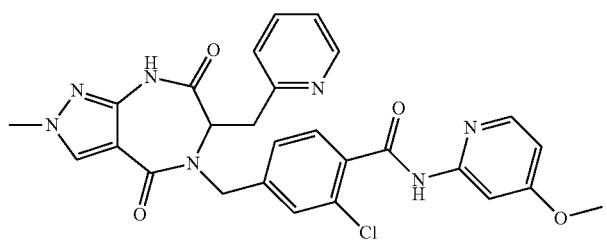<br>2-chloro-N-(4-methoxypyridin-2-yl)-4-((2-methyl-4,7-dioxo-6-(pyridin-2-ylmethyl)-2,6,7,8-tetrahydropyrazolo[3,4-e][1,4]diazepin-5(4H)-yl)methyl)benzamide | LCMS (ES) m/z = 546.29 [M + 1]$^+$; $^1$H NMR (400 MHz, DMSO-d6) δ 2.95-3.20 and 3.50-3.65 (m, 2H), 3.84 (s, 6H), 4.00-5.20 (m, 3H), 6.75 (dd, J = 6.0 and 2.4 Hz, 1H), 7.05-7.30 (m, 3H), 7.32 (s, 1H), 7.46 (d, J = 8.0 Hz, 1H), 7.67 (t, J = 6.8 Hz, 1H), 7.79 (s, 1H), 8.13 (d, J = 7.6 Hz, 1H), 8.25 (s, 1H), 8.35-8.52 (m, 1H), 10.80-11.10 (m, 2H); EC$_{50}$ = B. | A |
| 61 | 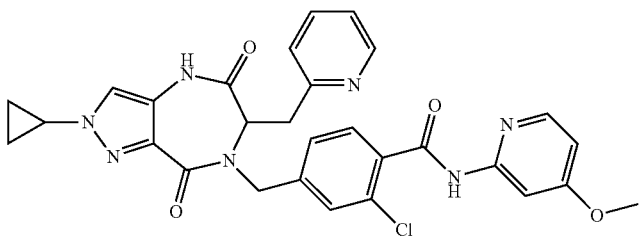<br>2-chloro-4-((2-cyclopropyl-5,8-dioxo-6-(pyridin-2-ylmethyl)-2,5,6,8-tetrahydropyrazolo[4,3-e][1,4]diazepin-7(4H)-yl)methyl)-N-(4-methoxypyridin-2-yl)benzamide | LCMS (ES) m/z = 572.32 [M + 1]$^+$; $^1$H NMR (400 MHz, DMSO-d6) δ 1.00-1.10 (m, 2H), 1.12-1.26 (m, 2H), 2.83-3.03, 3.15-3.24 and 3.50-3.60 (m, 2H), 3.84 (s, 3H), 3.88-3.95 (m, 1H), 4.15-5.12 (m, 3H), 6.76 (dd, J = 5.6 nd 2.4 Hz, 1H), 7.00-7.30 (m, 3H), 7.33 (s, 1H), 7.46 (d, J = 6.0 Hz, 1H), 7.60-7.83 (m, 3H), 8.13 (d, J = 5.6 Hz, 1H), 8.35-8.50 (m, 1H), 10.33 and 10.49 (2 × s, 1H), 10.90 and 10.94 (2 × s, 1H); Chiral purity (45:55); Column Name: CHIRALPAK IB (4.6 · 150)mm, 5μ, Mobile Phase: CO$_2$/MeOH (60:40), Flow rate: 3.0 mL/min, Flow mode: Isocratic, Column Temperature: 35° C., ABPR Pressure: 1500 psi: EC$_{50}$ = A. | A |

TABLE 1-continued

| Ex. No. | Structure; IUPAC Name. | LCMS; ¹HNMR; cellular morphology EC$_{50}$ range (μM). | Synthesis Method |
|---|---|---|---|
| 62 | 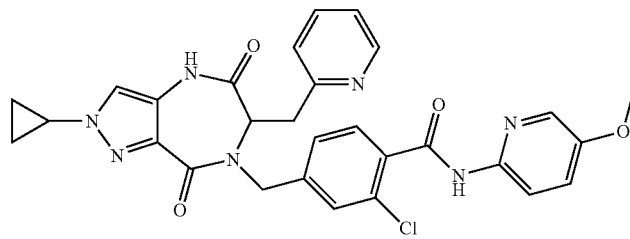<br>2-chloro-4-((2-cyclopropyl-5,8-dioxo-6-(pyridin-2-ylmethyl)-2,5,6,8-tetrahydropyrazolo[4,3-e][1,4]diazepin-7(4H)-yl)methyl)-N-(5-methoxypyridin-2-yl)benzamide | LCMS (ES) m/z = 572.32 [M + 1]⁺; ¹H NMR (400 MHz, DMSO-d6) δ 1.00-1.10 (m, 2H), 1.12-1.26 (m, 2H), 2.83-3.03, 3.15-3.24 and 3.50-3.60 (m, 2H), 3.81 (s, 3H), 3.88-3.95 (m, 1H), 4.15-5.10 (m, 3H), 7.00-7.30 (m, 3H), 7.33 (s, 1H), 7.45-7.50 (m, 2H), 7.62-7.77 (m, 2H), 8.04 (d, J = 2.8 Hz, 1H), 8.08 (d, J = 8.8 Hz, 1H), 8.37-7.50 (m, 1H), 10.34 and 10.49 (2 × s, 1H), 10.81 and 10.84 (2 × s, 1H); Chiral purity (45:55); Column Name: CHIRALPAK IB (4.6 · 150)mm, 5μ, Mobile PHase: CO$_2$/MeOH (60:40), Flow rate: 3.0 mL/min, Flow mode: Isocratic, Column Temperature: 35° C., ABPR Pressure: 1500 psi; EC$_{50}$ = B. | A |
| 63 | 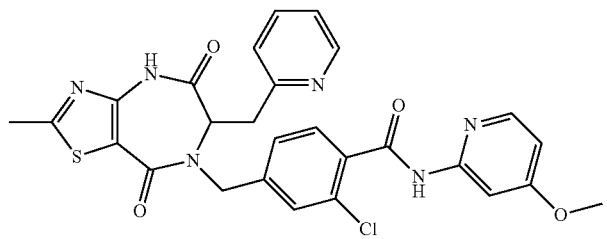<br>2-chloro-N-(4-methoxypyridin-2-yl)-4-((2-methyl-5,8-dioxo-6-(pyridin-2-ylmethyl)-4,5,6,8-tetrahydro-7H-thiazolo[4,5-e][1,4]diazepin-7-yl)methyl)benzamide | LCMS (ES) m/z = 563.02 [M + 1]⁺; ¹H NMR (400 MHz, DMSO-d6) δ 2.68 (s, 3H), 2.95-3.15 and 3.50-3.65 (m, 2H), 3.84 (s, 3H), 4.10-5.20 (m, 3H), 6.75 (dd, J = 6.0 and 2.4 Hz, 1H), 7.10-7.30 (m, 3H), 7.35 (s, 1H), 7.47 (d, J = 8.0 Hz, 1H), 7.70 (t, J = 6.8 Hz, 1H), 7.79 (s, 1H), 8.13 (d, J = 8.0 Hz, 1H), 8.46 (br s, 1H), 10.93 (s, 1H), 11.69 (br s, 1H); EC$_{50}$ = A. | A |
| 64 | 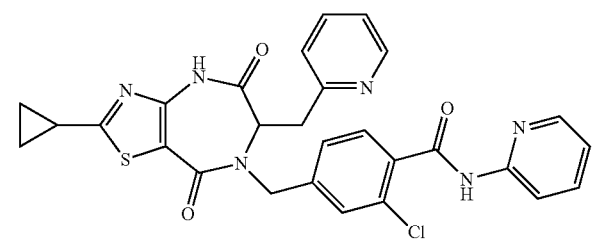<br>2-chloro-4-((2-cyclopropyl-5,8-dioxo-6-(pyridin-2-ylmethyl)-4,5,6,8-tetrahydro-7H-thiazolo[4,5-e][1,4]diazepin-7-yl)methyl)-N-(pyridin-2-yl)benzamide | LCMS (ES) m/z = 559.24 [M + 1]⁺; ¹H NMR (400 MHz, DMSO-d6) δ 1.00-1.10 (m, 2H), 1.12-1.36 (m, 2H), 2.40-2.45 (m,1H), 3.00-3.15 and 3.50-3.65 (m, 2H), 4.00-5.18 (m, 3H), 7.12-7.28 (m, 4H), 7.35 (s, 1H), 7.70 (t, J = 8.4 Hz, 1H), 7.83 (t, J = 9.2 Hz, 1H), 8.14 (d, J = 7.6 Hz, 1H), 8.33 (d, J = 3.6 Hz, 1H), 8.46 (br s, 1H), 10.96 (s, 1H), 11.58 (br s, 1H); Chiral purity (62:38); Column Name: CHIRALCEL OJH (4.6 · 250)mm, 5μ, Mobile Phase: CO$_2$/0.2% TEA in MeOH (60:40), Flow rate: 3.0 mL/min, Flow mode: Isocratic, | A |

| Ex. No. | Structure; IUPAC Name. | LCMS; ¹HNMR; cellular morphology $EC_{50}$ range (μM). | Synthesis Method |
|---|---|---|---|
| | | Column Temperature: 35° C., ABPR Pressure: 1500 psi; $EC_{50}$ = C. | |
| 65 | 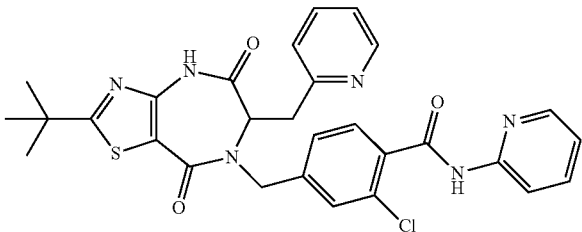<br>4-((2-(tert-butyl)-5,8-dioxo-6-(pyridin-2-ylmethyl)-4,5,6,8-tetrahydro-7H-thiazolo[4,5-e][1,4]diazepin-7-yl)methyl)-2-chloro-N-(pyridin-2-yl)benzamide | LCMS (ES) m/z = 575.28 [M + 1]⁺; ¹H NMR (400 MHz, DMSO-d6) δ 1.42 (s, 9H), 3.00-3.18 and 3.55-3.65 (m, 2H), 4.00-5.20 (m, 3H), 7.13-7.18 (m, 1H), 7.20-7.28 (m, 3H), 7.35 (s, 1H), 7.48 (d, J = 7.6 Hz, 1H), 7.71 (t, J = 7.6 Hz, 1H), 7.83 (t, J = 7.2 Hz, 1H), 8.14 (d, J = 8.4 Hz, 1H), 8.33 (d, J = 4.0 Hz, 1H), 8.46 (br s, 1H), 10.96 (s, 1H), 11.65 (br s, 1H); Chiral purity (47:53); Column Name: CHIRALPAK IC (4.6 · 250)mm, 5μ, Mobile Phase: $CO_2$/0.2% TEA in MeOH (80:20), Flow rate: 3.0 mL/min, Flow mode: Isocratic, Column Temperature: 35° C., ABPR Pressure: 1500 psi; $EC_{50}$ = C. | A |
| 66 | 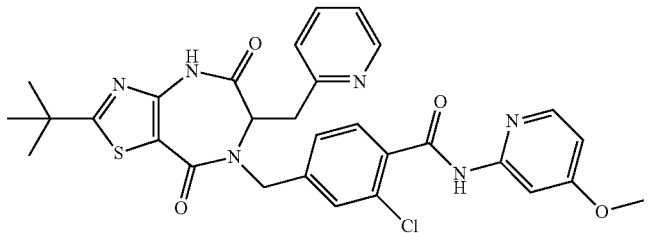<br>4-((2-(tert-butyl)-5,8-dioxo-6-(pyridin-2-ylmethyl)-4,5,6,8-tetrahydro-7H-thiazolo[4,5-e][1,4]diazepin-7-yl)methyl)-2-chloro-N-(4-methoxypyridin-2-yl)benzamide | LCMS (ES) m/z = 605.07 [M + 1]⁺; ¹H NMR (400 MHz, DMSO-d6) δ 1.41 (s, 9H), 3.00-3.15 and 3.55-3.65 (m, 2H), 4.00-5.20 (m, 3H), 6.76 (dd, J = 5.6 and 2.0 Hz, 1H), 7.10-7.28 (m, 3H), 7.35 (s, 1H), 7.46 (d, J = 7.6 Hz, 1H), 7.71 (t, J = 7.6 Hz, 1H), 7.79 (s, 1H), 8.13 (d, J = 5.6 Hz, 1H), 8.46 (br s, 1H), 10.93 (s, 1H), 11.64 (br s, 1H); Chiral purity (16:84); Column Name: CHIRALPAK IB-N (4.6 · 250)mm, 5μ, Mobile Phase: $CO_2$/0.2% TEA in MeOH (80:20), Flow rate: 3.0 mL/min, Flow mode: Isocratic, Column Temperature: 35° C., ABPR Pressure: 1500 psi; $EC_{50}$ = C. | A |

| Ex. No. | Structure; IUPAC Name. | LCMS; ¹HNMR; cellular morphology EC$_{50}$ range (μM). | Synthesis Method |
|---|---|---|---|
| 67 | 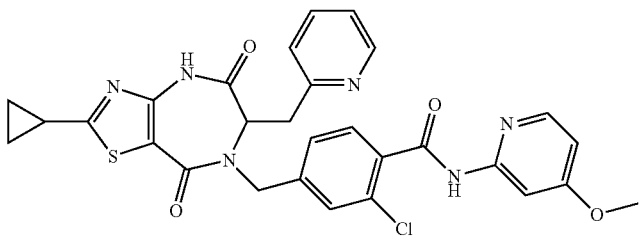<br>2-chloro-4-((2-cyclopropyl-5,8-dioxo-6-(pyridin-2-ylmethyl)-4,5,6,8-tetrahydro-7H-thiazolo[4,5-e][1,4]diazepin-7-yl)methyl)-N-(4-methoxypyridin-2-yl)benzamide | LCMS (ES) m/z = 589.05 [M + 1]⁺; ¹H NMR (400 MHz, DMSO-d6) δ 1.00-1.11 (m, 2H), 1.16-1.30 (m, 2H), 2.40-2.45 (m, 1H), 3.00-3.15 and 3.50-3.65 (m, 2H), 3.84 (s, 3H), 4.00-5.20 (m, 3H), 6.75 (dd, J = 5.6 and 2.0 Hz, 1H), 7.10-7.28 (m, 3H), 7.34 (s, 1H), 7.46 (d, J = 8.0 Hz, 1H), 7.70 (t, J = 8.0 Hz, 1H), 7.79 (s, 1H), 8.13 (d, J = 6.0 Hz, 1H), 8.46 (br s, 1H), 10.93 (s, 1H), 11.58 (br s, 1H); Chiral purity (20:80); Column NAME: CHIRALPAK IB (4.6 · 250)mm, 5μ, Mobile Phase: CO₂/0.2% TEA in MeOH (60:40), Flow rate: 3.0 mL/min, Flow mode: Isocratic, Column Temperature: 35° C., ABPR Pressure: 1500 psi; EC$_{50}$ = B. | A |
| 68 | 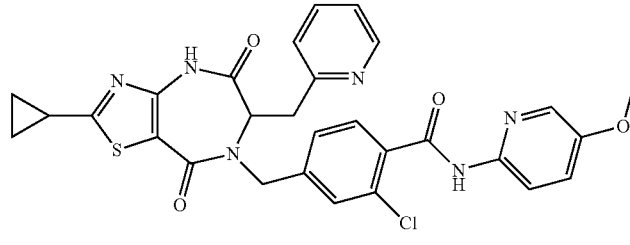<br>2-chloro-4-((2-cyclopropyl-5,8-dioxo-6-(pyridin-2-ylmethyl)-4,5,6,8-tetrahydro-7H-thiazolo[4,5-e][1,4]diazepin-7-yl)methyl)-N-(5-methoxypyridin-2-yl)benzamide | LCMS (ES) m/z = 589.01 [M + 1]⁺; ¹H NMR (400 MHz, DMSO-d6) δ 1.00-1.10 (m, 2H), 1.20-1.26 (m, 2H), 3.00-3.15 and 3.50-3.62 (m, 2H), 3.81 (s, 3H), 4.05-5.15 (m, 3H), 7.12-7.30 (m, 3H), 7.34 (s, 1H), 7.44-7.50 (m, 2H), 7.70 (t, J = 7.6 Hz, 1H), 8.04 (d, J = 2.8 Hz, 1H), 8.07 (d, J = 9.2 Hz, 1H), 8.46 (br s, 1H), 10.83 (s, 1H), 11.53 (br s, 1H); Chiral purity (83:17); Column Name: CHIRALCEL OJH (4.6 · 250)mm, 5μ, Mobile Phase: CO₂/0.2% TEA in MeOH (60:40), Flow rate: 3.0 mL/min, Flow mode: Isocratic, Column Temperature: 35° C., ABPR Pressure: 1500 psi; EC$_{50}$ = B. | A |
| 69 | 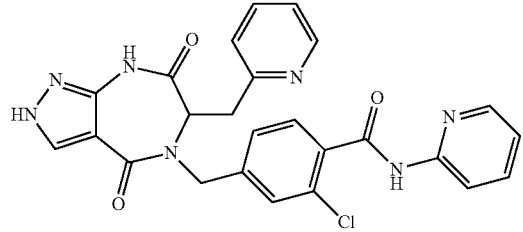<br>2-chloro-4-((4,7-dioxo-6-(pyridin-2-ylmethyl)-2,6,7,8-tetrahydropyrazolo[3,4-e][1,4]diazepin-5(4H)-yl)methyl)-N-(pyridin-2-yl)benzamide | LCMS (ES) m/z = 502.22 [M + 1]⁺; ¹H NMR (400 MHz, DMSO-d6) δ 2.90-3.20 and 3.50-3.65 (m, 2H), 4.05-5.20 (m, 3H), 7.08 (s, 1H), 7.15 (dd, J = 6.8 and 4.8 Hz, 1H), 7.20-7.30 (m, 2H), 7.34 (s, 1H), 7.48 (d, J = 8.0 Hz, 1H), 7.68 (t, J = 7.2 Hz, 1H), 7.84 (t, J = 7.2 Hz, 1H), 8.14 (d, J = 8.4 Hz, 1H), 8.29 (s, 1H), 8.32 (d, J = 3.6 Hz, 1H), 8.36-8.52 (m, 1H), 10.80-11.10 (m, 2H), 13.20 (s, 1H); | A |

TABLE 1-continued

| Ex. No. | Structure; IUPAC Name. | LCMS; ¹HNMR; cellular morphology $EC_{50}$ range (μM). | Synthesis Method |
|---|---|---|---|
| | | Chiral purity (28:72); Column Name: LUX I CELLULOSE-5 (4.6 · 150)mm, 5μ, Mobile Phase: $CO_2$/0.2% TEA in MeOH (60:40), Flow rate: 3.0 mL/min, Flow mode: Isocratic, Column Temperature: 35° C., ABPR Pressure: 1500 psi; $EC_{50}$ = C. | |
| 70 | 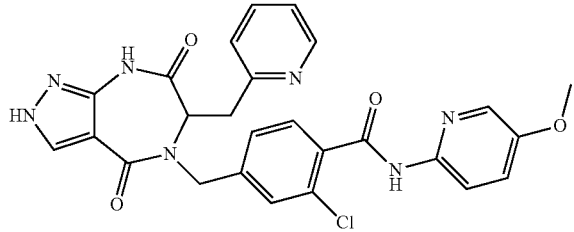  2-chloro-4-((4,7-dioxo-6-(pyridin-2-ylmethyl)-2,6,7,8-tetrahydropyrazolo[3,4-e][1,4]diazepin-5(4H)-yl)methyl)-N-(5-methoxypyridin-2-yl)benzamide | LCMS (ES) m/z = 532.24 [M + 1]⁺; ¹H NMR (400 MHz, DMSO-d6) δ 2.90-3.20 and 3.50-3.75 (m, 2H), 3.81 (s, 3H), 4.05-5.20 (m, 3H), 7.05-7.40 (m, 4H), 7.43-7.52 (m, 2H), 7.69 (t, J = 7.2 Hz, 1H), 8.04 (d, J = 2.4 Hz, 1H), 8.08 (d, J = 8.8 Hz, 1H), 8.29 (s, 1H), 8.35-8.43 (m, 1H), 10.84 (s, 1H), 11.02 (s, 1H), 13.19 (s, 1H); Chiral purity (26:74); Column Name: CHIRALPAK ID (4.6 · 250)mm, 5μ, Mobile Phase: $CO_2$/0.2% TEA in MeOH (60:40), Flow rate: 3.0 mL/min, Flow mode: Isocratic, Column Temperature: 35° C., ABPR Pressure: 1500 psi; $EC_{50}$ = C. | A |
| 71 | 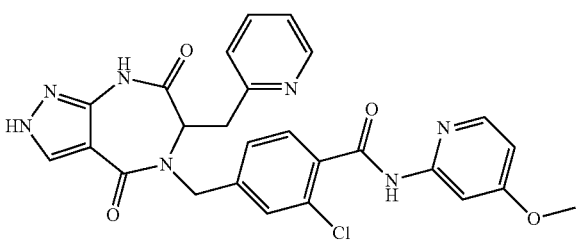  2-chloro-4-((4,7-dioxo-6-(pyridin-2-ylmethyl)-2,6,7,8-tetrahydropyrazolo[3,4-e][1,4]diazepin-5(4H)-yl)methyl)-N-(4-methoxypyridin-2-yl)benzamide | LCMS (ES) m/z = 532.24 [M + 1]⁺; ¹H NMR (400 MHz, DMSO-d6) δ 2.90-3.20 and 3.50-3.65 (m, 2H), 3.84 (s, 3H), 4.00-5.20 (m, 3H), 6.75 (dd, J = 6.0 and 2.4 Hz, 1H), 7.05-7.30 (m, 3H), 7.33 (s, 1H), 7.46 (d, J = 8.0 Hz, 1H), 7.68 (t, J = 6.8 Hz, 1H), 7.79 (s, 1H), 8.13 (d, J = 8.0 Hz, 1H), 8.26 (s, 1H), 8.35-8.50 (m, 1H), 10.70-11.20 (m, 2H), 13.00 (br s, 1H); $EC_{50}$ = B. | A |
| 72 | 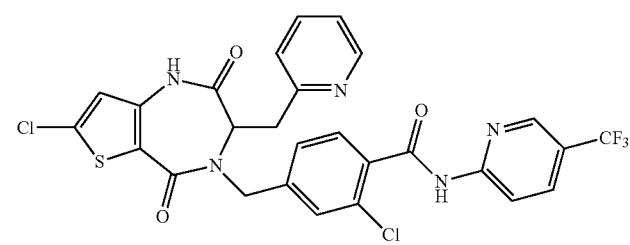  2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(5-(trifluoromethyl)pyridin-2-yl)benzamide | LCMS (ES) m/z = 620.11 [M + 1]⁺; ¹H NMR (400 MHz, DMSO-d6) δ 3.00-3.20 and 3.50-3.65 (m, 2H), 4.10-5.20 (m, 3H), 6.89 (s, 1H), 7.15-7.30 (m, 3H), 7.38 (s, 1H), 7.53 (d, J = 8.0 Hz, 1H), 7.70 (t, J = 8.0 Hz, 1H), 8.23 (dd, J = 8.8 and 2.0 Hz, 1H), 8.35 (d, J = 8.8 Hz, 1H), 8.46 (br s, 1H), 8.74 (s, 1H), 11.15 (br s, 1H), 11.48 (s, 1H); Chiral purity (94:6); Column Name: | A |

TABLE 1-continued

| Ex. No. | Structure; IUPAC Name. | LCMS; ¹HNMR; cellular morphology EC₅₀ range (μM). | Synthesis Method |
|---|---|---|---|
| | | CHIRALCELL OJH (4.6 · 250)mm, 5μ, Mobile Phase: CO₂/MeOH (60:40), Flow rate: 3.0 mL/min, Flow mode: Isocratic, Column Temperature: 35° C., ABPR Pressure: 1500 psi; EC₅₀ = A. | |
| 73 | 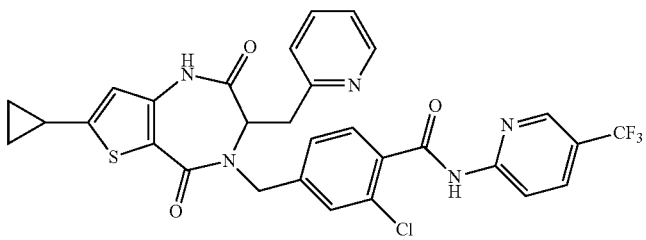<br>2-chloro-4-((7-cyclopropyl-2,5-dioxo-3-(pyridin-2-ylmethyl)-1,2,3,5-tetrahydro-4H-thieno[3,2-e][1,4]diazepin-4-yl)methyl)-N-(5-(trifluoromethyl)pyridin-2-yl)benzamide | LCMS (ES) m/z = 626.22 [M + 1]⁺; ¹H NMR (400 MHz, DMSO-d6) δ 0.70-0.80 (m, 2H), 1.06-1.15 (m, 2H), 2.18-2.26 (m, 1H), 2.97-3.15 and 3.50-3.65 (m, 2H), 4.05-5.15 (m, 3H), 6.59 (br s, 1H), 7.05-7.30 (m, 3H), 7.35 (s, 1H), 7.52 (d, J = 8.0 Hz, 1H), 7.70 (t, J = 7.2 Hz, 1H), 8.23 (dd, J = 8.8 and 2.0 Hz, 1H), 8.35 (d, J = 8.8 Hz, 1H), 8.46 (br s, 1H), 8.74 (s, 1H), 11.05 (br s, 1H), 11.48 (s, 1H); Chiral purity (19:81); Column Name: CHIRALPAK IB (4.6 · 250)mm, 5μ, Mobile Phase: CO₂/0.2% TEA in MeOH (60:40), Flow rate: 3.0 mL/min, Flow mode: Isocratic, Column Temperature: 35° C., ABPR Pressure: 1500 psi; EC₅₀ = A. | A |
| 74 | 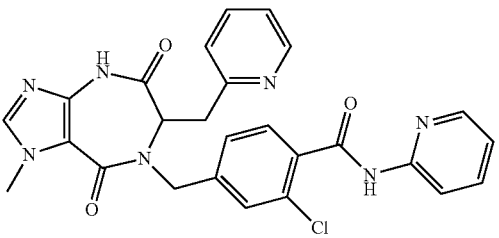<br>2-chloro-4-((1-methyl-5,8-dioxo-6-(pyridin-2-ylmethyl)-4,5,6,8-tetrahydroimidazo[4,5-e][1,4]diazepin-7(1H)-yl)methyl)-N-(pyridin-2-yl)benzamide | LCMS (ES) m/z = 516.27 [M + 1]⁺; ¹H NMR (400 MHz, DMSO-d6) δ 2.90-3.20 and 3.60-3.67 (m, 2H), 3.95-5.10 (m, 3H), 7.12-7.42 (m, 5H), 7.48 (t, J = 6.8 Hz, 1H), 7.66-7.73 (m, 1H), 7.78-7.84 (m, 2H), 8.12-8.20 (m, 1H), 8.33-8.50 (m, 2H), 10.90-11.10 (m, 2H); Chiral purity (16:84); Column Name: CHIRALPAK IB-N (4.6 · 250)mm, 5μ, Mobile Phase: CO₂/0.2% TEA in MeOH (80:20), Flow rate: 3.0 mL/min, Flow mode: Isocratic, Column Temperature: 35° C., ABPR Pressure: 1500 psi; EC₅₀ = C. | A |

TABLE 1-continued

| Ex. No. | Structure; IUPAC Name. | LCMS; ¹HNMR; cellular morphology $EC_{50}$ range (μM). | Synthesis Method |
|---|---|---|---|
| 75 | 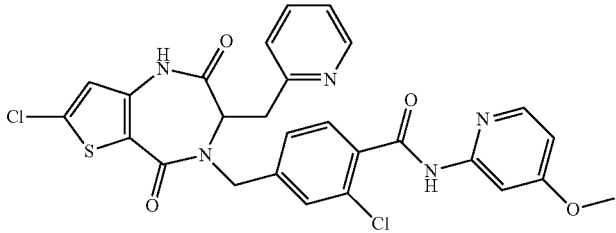<br>2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)benzamide | LCMS (ES) m/z = 582.21 [M + 1]⁺; ¹H NMR (400 MHz, DMSO-d6) δ 3.05-3.15 and 3.50-3.60 (m, 2H), 3.84 (s, 3H), 4.10-5.20 (m, 3H), 6.75 (dd, J = 5.6 and 1.2 Hz, 1H), 6.88 (s, 1H), 7.10-7.26 (m, 3H), 7.35 (s, 1H), 7.47 (d, J = 7.6 Hz, 1H), 7.70 (t, J = 7.6 Hz, 1H), 7.79 (s, 1H), 8.13 (d, J = 5.6 Hz, 1H), 8.46 (br s, 1H), 10.93 (s, 1H), 11.24 (br s, 1H); Chiral purity (1:1); Column Name: CHIRALPAK-IB (4.6 · 250)mm, 5μ, Mobile Phase: CO₂/0.2% TEA in MeOH (60:40), Flow rate: 3.0 mL/min, Flow mode: Isocratic, Column Temperature: 35° C., ABPR Pressure: 1500 psi; $EC_{50}$ = A. | A |
| 76 | 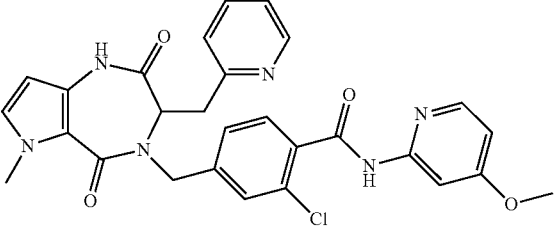<br>2-chloro-N-(4-methoxypyridin-2-yl)-4-((1-methyl-5,8-dioxo-6-(pyridin-2-ylmethyl)-4,5,6,8-tetrahydroimidazo[4,5-e][1,4]diazepin-7(1H)-yl)methyl)benzamide | LCMS (ES) m/z = 546.26 [M + 1]⁺; ¹H NMR (400 MHz, DMSO-d6) δ 2.93-3.20 and 3.75-3.70 (m, 2H), 3.84 (s, 6H), 3.95-5.10 (m, 3H), 6.75 (dd, J = 3.6 and 2.4 Hz, 1H), 7.12-7.42 (m, 4H), 7.44 (t, J = 6.8 Hz, 1H), 7.68 (t, J = 7.6 Hz, 1H), 7.79 s, 1H), 7.83 (s, 1H), 8.13 (d, J = 6.0 Hz, 1 H), 8.36-8.52 (m, 1H), 10.85-11.10 (m, 2H); Chiral purity (18:82); Column Name: CHIRALPAK IB-N (4.6 · 250)mm, 5μ, Mobile Phase: CO₂/0.2% TEA in MeOH (80:20), Flow rate: 3.0 mL/min, Flow mode: Isocratic, Column Temperature: 35° C., ABPR Pressure: 1500 psi; $EC_{50}$ = A. | A |
| 77 | 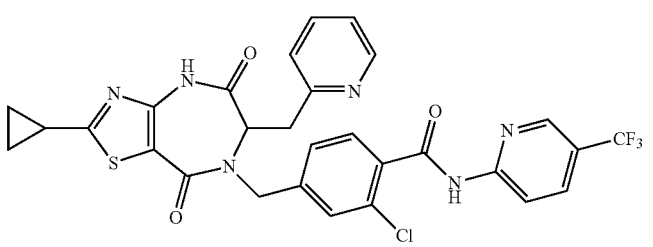<br>2-chloro-4-((2-cyclopropyl-5,8-dioxo-6-(pyridin-2-ylmethyl)-4,5,6,8-tetrahydro-7H-thiazolo[4,5-e][1,4]diazepin-7-yl)methyl)-N-(5-(trifluoromethyl)pyridin-2-yl)benzamide | LCMS (ES) m/z = 627.23 [M + 1]⁺; ¹H NMR (400 MHz, DMSO-d6) δ 1.00-1.15 (m, 2H), 1.20-1.28 (m, 2H), 1.42-1.46 (m, 1H), 2.95-3.15 and 3.45-3.60 (m, 2H), 4.05-5.20 (m, 3H), 6.89 (s, 1H), 7.10-7.30 (m, 3H), 7.38 (s, 1H), 7.52 (d, J = 8.0 Hz, 1H), 7.70 (t, J = 7.6 Hz, 1H), 8.23 (dd, J = 8.8 and 2.4 Hz, 1H), 8.35 (d, J = 8.8 Hz, 1H), 8.46 (br s, 1H), 8.74 (s, 1H), 11.48 (s, 1H), 11.56 (br s, 1H); Chiral purity (70:30); | A |

TABLE 1-continued

| Ex. No. | Structure; IUPAC Name. | LCMS; ¹HNMR; cellular morphology EC$_{50}$ range (μM). | Synthesis Method |
|---|---|---|---|
| | | Column Name: CHIRALCELL OJH (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = B. | |
| 78 | 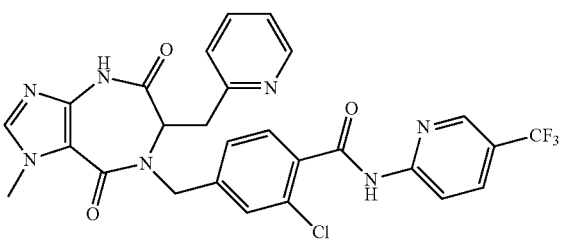<br>2-chloro-4-((1-methyl-5,8-dioxo-6-(pyridin-2-ylmethyl)-4,5,6,8-tetrahydroimidazo[4,5-e][1,4]diazepin-7(1H)-yl)methyl)-N-(5-(trifluoromethyl)pyridin-2-yl)benzamide | LCMS (ES) m/z = 584.23 [M + 1]; ¹H NMR (400 MHz, DMSO-d6) δ 2.95-3.20 and 3.60-3.70 (m, 2H), 3.84 (s, 3H), 4.00-5.10 (m, 3H), 7.10-7.45 (m, 4H), 7.52 (t, J = 6.0 Hz, 1H), 7.66-7.75 (m, 1H), 7.83 (s, 1H), 8.20-8.25 (m, 1H), 8.35-8.50 (m, 2H), 8.74 (s, 1H), 10.92 and 11.04 (2 s, 1H), 11.46 (s, 1H); Chiral purity (81:19); Column Name: LUX CELLULOSE-2 (4.6 · 250)mm, 5μ, Mobile Phase: CO$_2$/0.2% TEA in MeOH (80:20), Flow rate: 3.0 mL/min, Flow mode: Isocratic, Column Temperature: 35° C., ABPR Pressure: 1500 psi; EC$_{50}$ = C. | A |
| 79 | 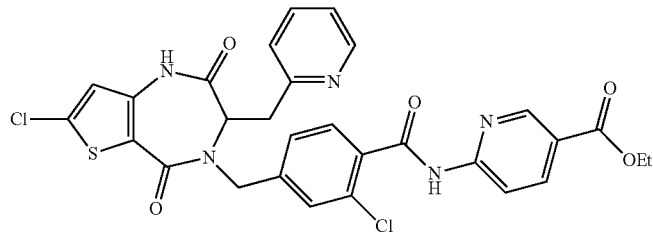<br>ethyl 6-(2-chloro-4-((7-chloro-2,5-dioxo-3-(pyridin-2-ylmethyl)-1,2,3,5-tetrahydro-4H-thieno[3,2-e][1,4]diazepin-4-yl)methyl)benzamido)nicotinate | LCMS (ES) m/z = 624.13 [M + 1]⁺; ¹H NMR (400 MHz, DMSO-d6) δ 1.33 (t, J = 6.8 Hz, 3H), 3.05-3.15 and 3.50-3.60 (m, 2H), 3.87 (s, 3H), 4.32 (q, J = 7.2 Hz, 2H), 4.10-5.20 (m, 3H), 6.89 (s, 1H), 7.05-7.03 (m, 3H), 7.37 (s, 1H), 7.52 (d, J = 8.0 Hz, 1H), 7.70 (t, J = 7.6 Hz, 1H), 8.29-8.35 (m, 2H), 8.46 (br s, 1H), 8.86 (s, 1H), 11.21 (br s, 1H), 11.44 (s, 1H); Chiral purity (25:75); Column Name: CHIRALPAK-IB (4.6 · 250)mm, 5μ, Mobile Phase: CO$_2$ in MeOH (60:40), Flow rate: 3.0 mL/min, Flow mode: Isocratic, Column Temperature: 35° C., ABPR Pressure: 1500 psi; EC$_{50}$ = A. | A |

TABLE 1-continued

| Ex. No. | Structure; IUPAC Name. | LCMS; ¹HNMR; cellular morphology EC$_{50}$ range (μM). | Synthesis Method |
|---|---|---|---|
| 80 | 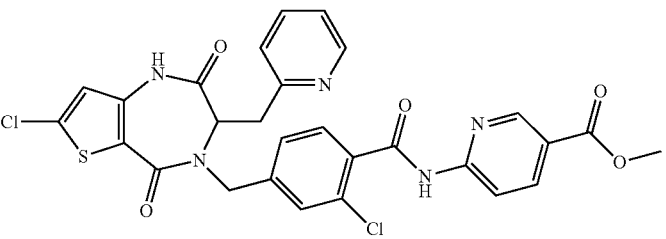<br>methyl 6-(2-chloro-4-((7-chloro-2,5-dioxo-3-(pyridin-2-ylmethyl)-1,2,3,5-tetrahydro-4H-thieno[3,2-e][1,4]diazepin-4-yl)methyl)benzamido)nicotinate | LCMS (ES) m/z = 610.00 [M + 1]$^+$; $^1$H NMR (400 MHz, DMSO-d6) δ 3.05-3.15 and 3.50-3.60 (m, 2H), 3.87 (s, 3H), 4.10-5.20 (m, 3H), 6.89 (s, 1H), 7.15-7.30 (m, 3H), 7.38 (s, 1H), 7.52 (d, J = 8.0 Hz, 1H), 7.70 (t, J = 7.6 Hz, 1H), 7.28-7.38 (m, 2H), 8.46 (br s, 1H), 8.86 (s, 1H), 11.23 (s, 1H), 11.44 (s, 1H); Chiral purity (1:1); Column Name: CHIRALPAK-IB (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi: EC$_{50}$ = A. | A |
| 81 | 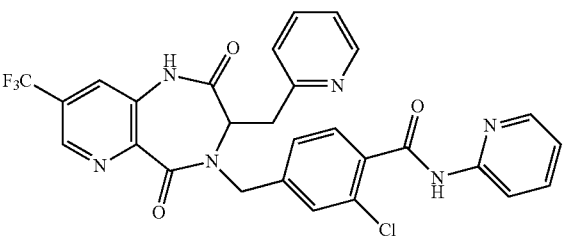<br>2-chloro-4-((2,5-dioxo-3-(pyridin-2-ylmethyl)-8-(trifluoromethyl)-1,2,3,5-tetrahydro-4H-pyrido[3,2-e][1,4]diazepin-4-yl)methyl)-N-(pyridin-2-yl)benzamide | LCMS (ES) m/z = 581.20 [M + 1]$^+$; $^1$H NMR (400 MHz, DMSO-d6) δ 2.75-2.95 (m, 1H), 3.48-3.57 (m, 1H), 4.44-5.18 (m, 3H), 7.00-7.35 (m, 5H), 7.46-7.53 (m, 1H), 7.63-7.71 (m, 1H), 7.83 (t, J = 7.2 Hz, 1H), 7.90-7.98 (m, 1H), 8.10-8.20 (m, 1H), 8.33-8.47 (m, 2H), 8.94 (s, 1H), 10.88 (s, 1H), 10.96 (s, 1H); Chiral purity (1:1); Column Name: CHIRALPAK-IBN-5 (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = A. | C |
| 82 | 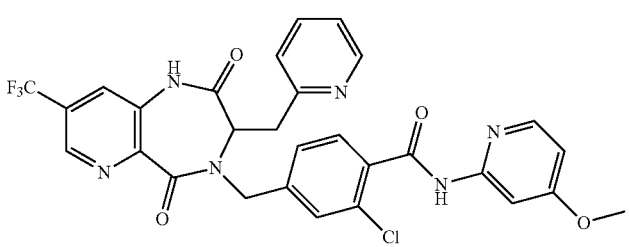<br>2-chloro-4-((2,5-dioxo-3-(pyridin-2-ylmethyl)-8-(trifluoromethyl)-1,2,3,5-tetrahydro-4H-pyrido[3,2-e][1,4]diazepin-4-yl)methyl)-N-(4-methoxypyridin-2-yl)benzamide | LCMS (ES) m/z = 611.19 [M + 1]$^+$; $^1$H NMR (400 MHz, DMSO-d6) δ 2.75-2.95 (m, 1H), 3.48-3.56 (m, 1H), 3.85 (s, 1H), 4.45-5.18 (m, 3H), 6.76 (dd, J = 6.4 and 2.4 Hz, 1H), 7.00-7.36 (m, 4H), 7.45-7.51 (m, 1H), 7.63-7.70 (m, 1H), 7.80 (s, 1H), 7.90-7.97 (m, 1H), 8.14 (d, J = 5.6 Hz, 1H), 8.35-8.45 (m, 1H), 8.94 (s, 1H), 10.80-11.00 (m, 2H); Chiral purity (1:1); Column Name: CHIRALPAK-IBN-5 (4.6 · 250)mm, 5μ, Mobile Phase: CO$_2$/0.2% TEA in | C |

TABLE 1-continued

| Ex. No. | Structure; IUPAC Name. | LCMS; ¹HNMR; cellular morphology EC$_{50}$ range (μM). | Synthesis Method |
|---|---|---|---|
| | | MeOH (60:40), Flow rate: 3.0 mL/min, Flow mode: Isocratic, Column Temperature: 35° C., ABPR Pressure: 1500 psi; EC$_{50}$ = A. | |
| 83 | 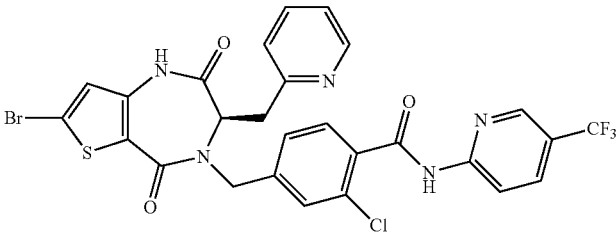<br>(R)-4-((7-bromo-2,5-dioxo-3-(pyridin-2-ylmethyl)-1,2,3,5-tetrahydro-4H-thieno[3,2-e][1,4]diazepin-4-yl)methyl)-2-chloro-N-(5-(trifluoromethyl)pyridin-2-yl)benzamide | LCMS (ES) m/z = 664.08, 666.09 [M + 1]⁺; ¹H NMR (400 MHz, DMSO-d$_6$) δ 3.00-3.20 and 3.50-3.60 (m, 2H), 4.10-5.20 (m, 3H), 6.97 (s, 1H), 7.10-7.30 (m, 3H), 7.38 (s, 1H), 7.53 (d, J = 8.0 Hz, 1H), 7.70 (t, J = 7.6 Hz, 1H), 8.23 (dd, J = 8.8 and 2.0 Hz, 1H), 8.35 (d, J = 9.2 Hz, 1H), 8.46 (br s, 1H), 8.74 (s, 1H), 11.22 (br s, 1H), 11.49 (s, 1H); Chiral purity (9:91); Column Name: LUX Cellulose-2 (4.6 · 250)mm, 5μ, Mobile Phase: CO$_2$ in MeOH (60:40), Flow rate: 3.0 mL/min, Flow mode: Isocratic, Column Temperature: 35° C., ABPR Pressure: 1500 psi; EC$_{50}$ = A. | A |
| 84 | 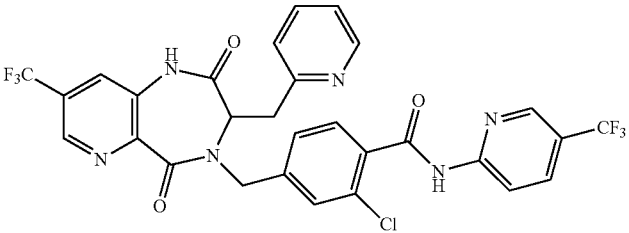<br>2-chloro-4-((2,5-dioxo-3-(pyridin-2-ylmethyl)-8-(trifluoromethyl)-1,2,3,5-tetrahydro-4H-pyrido[3,2-e][1,4]diazepin-4-yl)methyl)-N-(5-(trifluoromethyl)pyridin-2-yl)benzamide | LCMS (ES) m/z = 649.21 [M + 1]⁺; ¹H NMR (400 MHz, DMSO-d6) δ 2.78-2.98 (m, 1H), 3.48-3.56 (m, 1H), 4.45-5.18 (m, 3H), 7.00-7.40 (m, 4H), 7.50-7.55 (m, 1H), 7.63-7.70 (m, 1H), 7.90-7.97 (m, 1H), 8.23 (dd, J = 9.2 and 2.8 Hz, 1H), 8.35-8.45 (m, 2H), 8.74 (s, 1H), 8.94 (s, 1H), 10.85 (br s, 1H), 11.48 (s, 1H); Chiral purity (1:1); Column Name: LUX Cellulose 2 (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = A. | C |

TABLE 1-continued

| Ex. No. | Structure; IUPAC Name. | LCMS; ¹HNMR; cellular morphology EC$_{50}$ range (μM). | Synthesis Method |
|---|---|---|---|
| 85 | 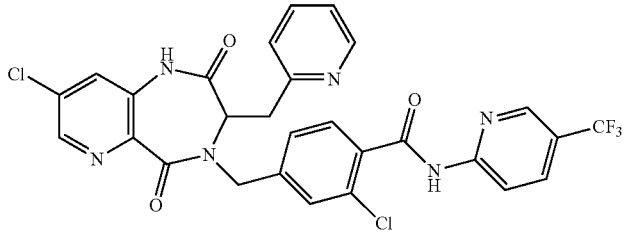<br>2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(5-(trifluoromethyl)pyridin-2-yl)benzamide | LCMS (ES) m/z = 615.16 [M + 1]$^+$; $^1$H NMR (400 MHz, DMSO-d6) δ 2.75-2.94 (m, 1H), 3.48-3.56 (m, 1H), 7.00-7.40 (m, 4H), 7.50-7.55 (m, 1H), 7.63-7.73 (m, 2H), 7.83-7.87 (m, 1H), 8.34-8.46 (m, 2H), 8.61 (s, 1H), 8.74 (s, 1H), 10.75-10.90 (m, 1H), 11.43-1.152 (m, 1H); Chiral purity (13:87); Column Name: CHIRALPAK IB (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = A. | C |
| 86 | 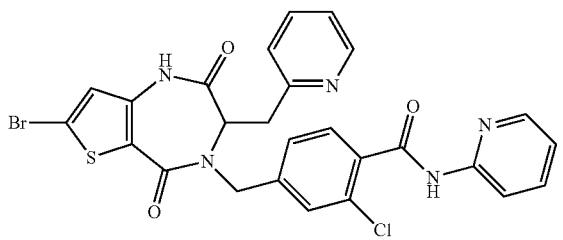<br>4-((7-bromo-2,5-dioxo-3-(pyridin-2-ylmethyl)-1,2,3,5-tetrahydro-4H-thieno[3,2-e][1,4]diazepin-4-yl)methyl)-2-chloro-N-(pyridin-2-yl)benzamide | LCMS (ES) m/z = 596.07, 598.09 [M + 1]$^+$; $^1$H NMR (400 MHz, DSO-d6) δ 3.00-3.20 and 3.50-3.60 (m, 2H), 4.10-5.15 (m, 3H), 6.97 (s, 1H), 7.13-7.28 (m, 4H), 7.36 (s, 1H), 7.49 (d, J = 8.0 Hz, 1H), 7.71 (t, J = 7.6 Hz, 1H), 7.83 (t, J = 8.4 Hz, 1H), 8.12-8.20 (m, 1H), 8.33 (d, J = 3.6 Hz, 1H), 8.46 (br s, 1H), 10.97 (s, 1H), 11.22 (br s, 1H); Chiral purity (17:83); Column Name: CHIRALPAK IB (4.6 · 250)mm, 5μ, Mobile Phase = CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = A. | A |
| 87 | 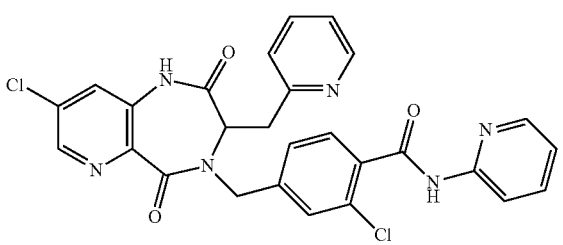<br>2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(pyridin-2-yl)benzamide | LCMS (ES) m/z = 547.21 [M + 1]$^+$; $^1$H NMR (400 MHz, DMSO-d6) δ 2.75-2.95 (m, 1H), 3.48-3.56 (m, 1H), 4.40-5.15 (m, 3H), 7.15-7.34 (m, 4H), 7.35 (s, 1H), 7.46-7.52 (m, 1H), 7.64-7.74 (m, 2H), 7.80-7.86 (m, 1H), 8.13-8.20 (m, 1H), 8.33-8.46 (m, 2H), 8.60 (d, J = 2.0 Hz, 1H), 10.90-11.00 (m, 2H); EC$_{50}$ = A. | C |

| Ex. No. | Structure; IUPAC Name. | LCMS; ¹HNMR; cellular morphology $EC_{50}$ range (μM). | Synthesis Method |
|---|---|---|---|
| 88 | 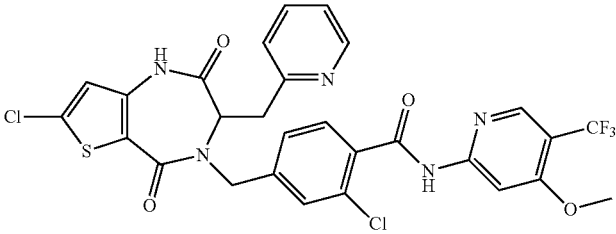<br>2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(4-methoxy-5-(trifluoromethyl)pyridin-2-yl)benzamide | LCMS (ES) m/z = 650.17 [M + 1]⁺; H NMR (400 MHz, DMSO-d6) δ 3.05-3.25 (m, 2H), 3.99 (s, 3H), 4.10-5.20 (m, 3H), 6.89 (s, 1H), 7.15-7.30 (m, 3H), 7.37 (s, 1H), 7.51 (d, J = 8.0 Hz, 1H), 7.70 (t, J = 7.6 Hz, 1H), 8.08 (s, 1H), 8.44-8.52 (m, 2H), 11.18 (br s, 1H), 11.40 (s, 1H); Chiral purity (33:67); Column Name: CHIRALPAK IB (4.6 · 250)mm, 5μ, Mobile Phase: $CO_2$ in MeOH (60:40), Flow rate: 3.0 mL/min, Flow mode: Isocratic, Column Temperature: 35° C., ABPR Pressure: 1500 psi; $EC_{50}$ = A. | A |
| 89 | 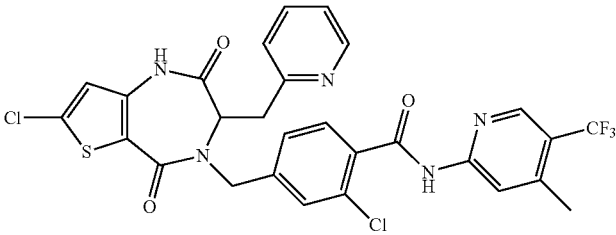<br>2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(4-methyl-5-(trifluoromethyl)pyridin-2-yl)benzamide | LCMS (ES) m/z = 634.12 [M + 1]⁺; ¹H NMR (400 MHz, DMSO-d6) δ 2.49 (s, 3H), 3.00-3.20 (m, 2H), 4.10-5.00 (m, 3H), 6.88 (s, 1H), 7.15-7.30 (m, 3H), 7.37 (s, 1H), 7.51 (d, J = 8.0 Hz, 1H), 7.70 (t, J = 7.6 Hz, 1H), 8.24 (s, 1H), 8.46 (br s, 1H), 8.59 (s, 1H), 11.20 (br s, 1H), 11.38 (s, 1H); Chiral purity (23:77); Column Name: CHIRALPAK IB (4.6 · 250)mm, 5μ, Mobile Phase: $CO_2$ in MeOH (60:4), Flow rate: 3.0 mL/min, Flow mode: Isocratic, Column Temperature: 35° C., ABPR Pressure: 1500 psi; $EC_{50}$ = A. | A |
| 90 | 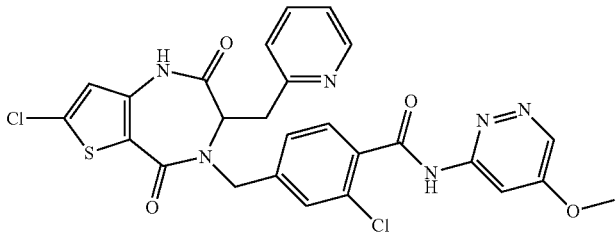<br>2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(5-methoxypyridazin-3-yl)benzamide | LCMS (ES) m/z = 583.12 [M + 1]⁺; ¹H NMR (400 MHz, DMSO-d6) δ 3.05-3.20 (m, 2H), 3.93 (s, 3H), 4.10-5.10 (m, 3H), 6.89 (s, 1H), 7.15-7.30 (m, 3H), 7.38 (s, 1H), 7.53 (d, J = 8.0 Hz, 1H), 7.70 (t, J = 7.6 Hz, 1H), 7.98 (s, 1H), 8.46 (br s, 1H), 8.79 (d, J = 2.8 Hz, 1H), 11.24 (br s, 1H), 11.57 (s, 1H); Chiral purity (19:81); Column Name: CHIRALPAK IB (4.6 · 250)mm, 5μ, Mobile Phase: $CO_2$ in MeOH (60:40), Flow rate: 3.0 mL/min, Flow mode: Isocratic, Column Temperature: 35° C., ABPR Pressure: 1500 psi; $EC_{50}$ = B. | A |

TABLE 1-continued

| Ex. No. | Structure; IUPAC Name. | LCMS; ¹HNMR; cellular morphology EC$_{50}$ range (μM). | Synthesis Method |
|---|---|---|---|
| 91 | 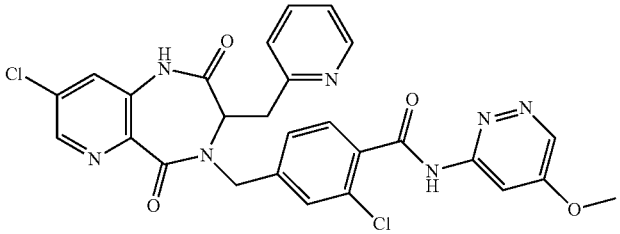<br>2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(5-methoxypyridazin-3-yl)benzamide | LCMS (ES) m/z = 578.17 [M + 1]⁺; ¹H NMR (400 MHz, DMSO-d6) δ 2.75-3.05 and 3.48-3.60 (m, 2H), 3.93 (s, 3H), 4.45-4.90 (m, 3H), 6.85-7.40 (m, 5H), 7.44-7.52 (m, 1H), 7.55-7.63 (m, 1H), 7.98 (s, 1H), 8.08 (br s, 1H), 8.30-8.42 (m, 1H), 8.75 (s, 1H), 11.30-11.80 (br s, 2H); Chiral purity (43:57); Column Name: CHIRALPAK IB (4.6 · 250)mm, 5μ, Mobile Phase: CO$_2$ in MeOH (60:40), Flow rate: 3.0 mL/min, Flow mode: Isocratic, Column Temperature: 35° C., ABPR Pressure: 1500 psi; EC$_{50}$ = B. | C |
| 92 | 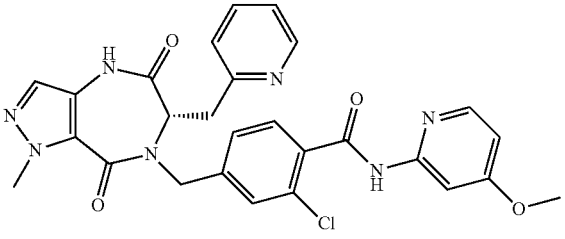<br>(S)-2-chloro-N-(4-methoxypyridin-2-yl)-4-((1-methyl-5,8-dioxo-6-(pyridin-2-ylmethyl)-4,5,6,8-tetrahydropyrazolo[4,3-e][1,4]diazepin-7(1H)-yl)methyl)benzamide | LCMS (ES) m/z = 546.20 [M + 1]⁺; ¹H NMR (400 MHz, DMSO-d6) δ 2.85-3.25 and 3.56-3.68 (m, 2H), 3.84 (s, 3H), 4.04 and 4.06 (2 × s, 3H), 4.60-5.15 (m, 3H), 6.76 (dd, J = 5.6 and 2.0 Hz, 1H), 7.15-7.35 (m, 5H), 7.43-7.50 (m, 1H), 7.65-7.73 (m, 1H), 7.78 (s, 1H), 8.14 (d, J = 6.0 Hz, 1H), 8.38 and 8.48 (m, 1H), 10.49 and 10.66 (2 × s, 1H), 10.93 (s, 1H); EC$_{50}$ = B. | B |
| 93 | 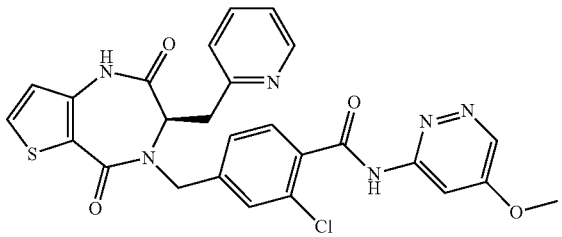<br>(R)-2-chloro-4-((2,5-dioxo-3-(pyridin-2-ylmethyl)-1,2,3,5-tetrahydro-4H-thieno[3,2-e][1,4]diazepin-4-yl)methyl)-N-(5-methoxypyridazin-3-yl)benzamide | LCMS (ES) m/z = 549.09 [M + 1]⁺; ¹H NMR (400 MHz, DMSO-d6) δ 2.90-3.10 and 3.55-3.65 (m, 2H), 4.10-5.15 (m, 3H), 6.85 (d, J = 4.8 Hz, 1H), 7.05-7.30 (m, 3H), 7.38 (s, 1H), 7.53 (d, J = 8.4 Hz, 1H), 7.70 (t, J = 7.2 Hz, 1H), 7.90 (d, J = 5.6 Hz, 1H), 7.98 (s, 1H), 8.46 (br s, 1H), 8.78 (d, J = 2.4 Hz, 1H), 11.15 (br s, 1H), 11.57 (s, 1H); Chiral purity (>98%); Column Name: CHIRALCEL OJ-H (4.6 · 250)mm, 5μ, Mobile Phase: CO$_2$/MeOH (60:40), Flow rate: 3.0 mL/min, Flow mode: Isocratic, Column Temperature: 35° C., ABPR Pressure: 1500 psi; EC$_{50}$ = C. | A |

| Ex. No. | Structure; IUPAC Name. | LCMS; ¹HNMR; cellular morphology EC$_{50}$ range (μM). | Synthesis Method |
|---|---|---|---|
| 94 | 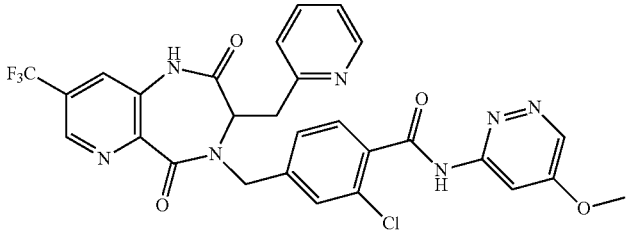<br>2-chloro-4-((2,5-dioxo-3-(pyridin-2-ylmethyl)-8-(trifluoromethyl)-1,2,3,5-tetrahydro-4H-pyrido[3,2-e][1,4]diazepin-4-yl)methyl)-N-(5-methoxypyridazin-3-yl)benzamide | LCMS (ES) m/z = 612.06 [M + 1]⁺; ¹H NMR (400 MHz, DMSO-d6) δ 2.75-2.95 and 3.48-3.55 (m, 2H), 3.94 (s, 3H), 4.45-5.20 (m, 3H), 7.00-7.40 (m, 4H), 7.55-7.58 (m, 1H), 7.60-7.70 (m, 1H), 7.88-8.02 (m, 2H), 8.35-8.45 (m, 1H), 8.79 (d, J = 2.8 Hz, 1H), 8.94 (s, 1H), 10.80-11.00 (m, 1H), 11.56 (s, 1H); Chiral purity (43:57); Column Name: CHIRALPAK IB (4.6 · 250)mm, 5μ, Mobile Phase: CO$_2$ in MeOH (60:40), Flow rate: 3.0 mL/min, Flow mode: Isocratic, Column Temperature: 35° C., ABPR Pressure: 1500 psi; EC$_{50}$ = D. | C |
| 95 | 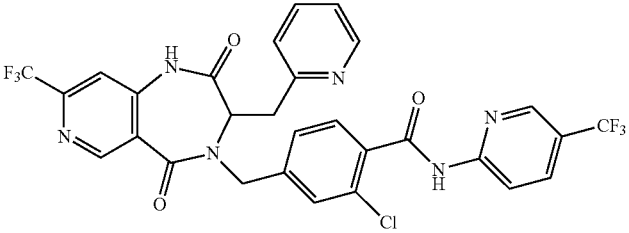<br>2-chloro-4-((2,5-dioxo-3-(pyridin-2-ylmethyl)-8-(trifluoromethyl)-1,2,3,5-tetrahydro-4H-pyrido[4,3-e][1,4]diazepin-4-yl)methyl)-N-(5-(trifluoromethyl)pyridin-2-yl)benzamide | LCMS (ES) m/z = 649.06 [M + 1]⁺; ¹H NMR (400 MHz, DMSO-d6) δ 2.90-3.05 (m, 1H), 3.52-3.65 (m, 1H), 4.30-5.20 (m, 3H), 7.10-7.38 (m, 3H), 7.40-7.48 (m, 1H), 75.2-7.62 (m, 2H), 7.64-7.74 (m, 1H), 8.22-8.78 (m, 1H), 8.34-8.50 (m, 2H), 8.74 (s, 1H), 9.08 (s, 1H), 11.25-11.65 (m, 1H); Chiral purity (1:1); Column Name: LUX Cellulose 2 (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; EC$_{50}$ = A. | C |
| 96 | 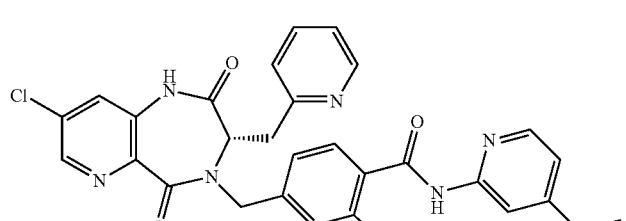<br>(S)-2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(4-methoxypyridin-2-yl)benzamide | LCMS (ES) m/z = 577.26 [M + 1]⁺; H NMR (400 MHz, DMSO-d6) δ 2.70-2.86, 3.10-3.20 and 3.50-3.60 (m, 2H), 3.85 (s, 3H), 4.40-4.90 (m, 3H), 6.73 (d, J = 5.2 Hz, 1H), 6.90-7.32 (m, 3H), 7.35 (s, 1H), 7.40-7.50 (m, 2H), 7.60 (br s, 1H), 7.75 (s, 1H), 8.13 (d, J = 5.2 Hz, 1H), 8.28 (s, 1H), 8.36 (br s, 1H), 10.52 (br s, 1H); EC$_{50}$ = A. | C |

TABLE 1-continued

| Ex. No. | Structure; IUPAC Name. | LCMS; $^1$HNMR; cellular morphology $EC_{50}$ range (μM). | Synthesis Method |
|---|---|---|---|
| 97 | 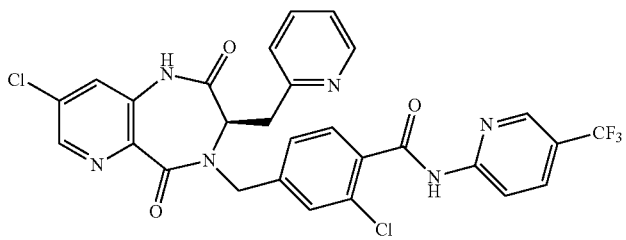<br>(R)-2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(5-(trifluoromethyl)pyridin-2-yl)benzamide | LCMS (ES) m/z = 615.12 [M + 1]$^+$; $^1$H NMR (400 MHz, DMSO-d6) δ 2.75-2.95 (m, 1H), 3.48-3.60 (m, 1H), 3.85 (s, 3H), 4.44-5.15 (m, 3H), 6.75-7.50 (m, 6H), 7.60-7.72 (m, 2H), 7.79 (s, 1H), 8.14 (d, J = 5.2 Hz, 1H), 8.35-8.46 (m, 1H), 8.61 (s, 1H), 10.75-11.00 (m, 2H); Chiral purity (>99%); Column Name: CHIRALPAK-IB (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; $EC_{50}$ = A. | C |
| 98 | 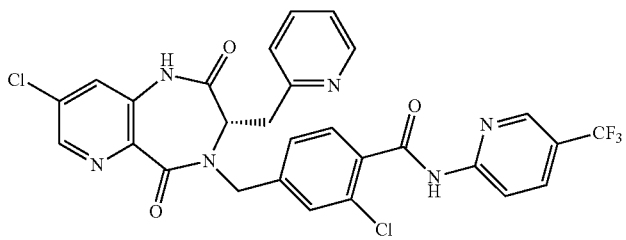<br>(S)-2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(5-(trifluoromethyl)pyridin-2-yl)benzamide | LCMS (ES) m/z = 615.12 [M + 1]$^+$; H NMR (400 MHz, DMSO-d6) δ 2.75-2.95 (m, 1H), 3.48-3.60 (m, 1H), 3.85 (s, 3H), 4.44-5.15 (m, 3H), 6.75-7.50 (m, 6H), 7.60-7.72 (m, 2H), 7.79 (s, 1H), 8.14 (d, J = 5.2 Hz, 1H), 8.35-8.46 (m, 1H), 8.61 (s, 1H), 10.75-11.00 (m, 2H); Chiral purity (>99%); Column Name: CHIRALPAK-IB (4.6 · 250)mm, 5μ, Mobile Phase: CO$_2$/0.2% TEA in MeOH (60:40), Flow rate: 3.0 mL/min, Flow mode: Isocratic, Column Temperature: 35° C., ABPR Pressure: 1500 psi; $EC_{50}$ = A. | C |

Biological Evaluation

The exemplified compounds of the present disclosure were tested in the cell-based morphology assay, and assay results were reported in Table 1 together with other analytical data.

Cell-Based Assay Details:

The exemplified compounds of the present disclosure were tested in the *Clostridium difficile* toxin B morphological profiling assay and results are reported in Table 1 together with other analytical data. The morphological consequences elicited by Human umbilical vein endothelial cells (HUVEC) exposed to TCdB were assessed using an experimental protocol adapted from Bray et al., Nat Protoc. 2016 September; 11(9): 1757-1774, reference in patent and quantified using Recursion's proprietary image analysis methods described in U.S. Pat. No. 10,146,914. HUVECs (Lonza) were seeded in 1536 well microtiter plates (789866, Greiner bio-one) coated with PDL and collagen and incubated in EGM2 (Lonza) for 24 hours at 37 C and a 5% CO2 atmosphere. After 24 hours of incubation, HUVEC were pretreated with compounds dissolved in DMSO and exposed to 5 ng/mL TCdB (ListLabs) with an Echo acoustic dispenser (Labcyte). Upon conclusion of TCdB incubation 24 hours post toxin exposure, cells were treated with mitotracker deep red (Invitrogen) and subsequently fixed in 2.6% PFA, permeabilized in a solution of triton X-100, and stained with a solution of Hoechst, ConA, Syto14, WGA, and Phalloidin in HBSS (all Invitrogen). The cells were then imaged, and images were processed with Cell Profiler to extract cell-level morphological features. A proprietary algorithm was then used to determine the feature profile associated with toxin exposure as compared to healthy, unexposed cells. These profiles were used to define a vector by which we would evaluate all wells in the assay on a 0-1 scale (0 being healthy, and 1 is defined as toxin treated). Profiles from compound-treated toxin-exposed are projected onto this axis to approximate the level of similarity to disease or healthy of the well. Compound values are then fit to a 4-parameter log agonist-response equation to calculate an $EC_{50}$ value.

What is claimed is:

1. A compound of Formula (I):

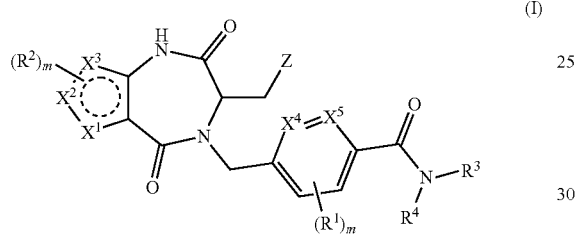

(I)

or a stereoisomer, a tautomer, or a pharmaceutically acceptable salt thereof;
wherein
$X^1$, $X^2$, and $X^3$ are each independently $CR^2$, N, $NR^5$, O, or S;
$X^4$ and $X^5$ are each independently C(H) or N;
m is an integer of 0, 1, or 2;
Z is a 6- to 10-membered aryl or, 5- to 10-membered heteroaryl containing 1 to 3 heteroatoms independently selected from N, O, and S;
$R^1$ and $R^2$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;
$R^3$ and $R^4$ are each independently hydrogen, $C_{1-6}$ alkyl, alkylamino, haloalkyl, alkoxy, haloalkoxy, 6- to 10-membered aryl, 5- to 10-membered heteroaryl containing 1 to 3 heteroatoms independently selected from N, O, and S, 3- to 10-membered carbocyclyl, or 4- to 10-membered heterocyclyl containing 1 to 3 heteroatoms independently selected from N, O, and S, wherein the aryl, heteroaryl, carbocyclyl, and heterocyclyl are independently substituted with 0 to 5 $R^5$;
$R^5$ is hydrogen, halo, cyano, hydroxyl, amino, $C_{1-6}$ alkyl, alkylamino, haloalkyl, hydroxyalkyl, hydroxycycloalkyl, aminoalkyl, alkoxyalkyl, haloalkoxyalkyl, alkoxy, haloalkoxy or $—C(O)OR^6$; and
$R^6$ is hydrogen or $C_{1-6}$ alkyl.

2. The compound according to claim 1, or a stereoisomer, a tautomer, or a pharmaceutically acceptable salt thereof; wherein the

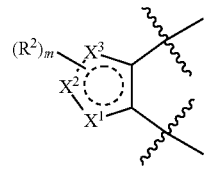

moiety is

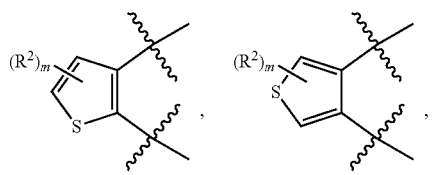

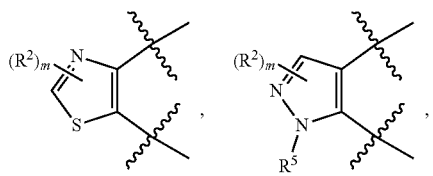

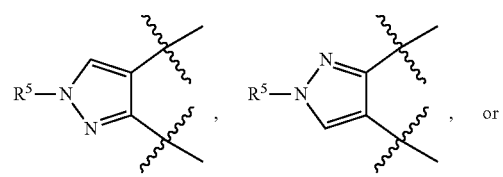

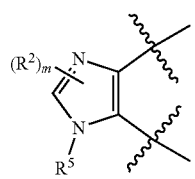

3. The compound according to claim 1, or a stereoisomer, a tautomer, or a pharmaceutically acceptable salt thereof; wherein:
$R^3$ is hydrogen and $R^4$ is selected from

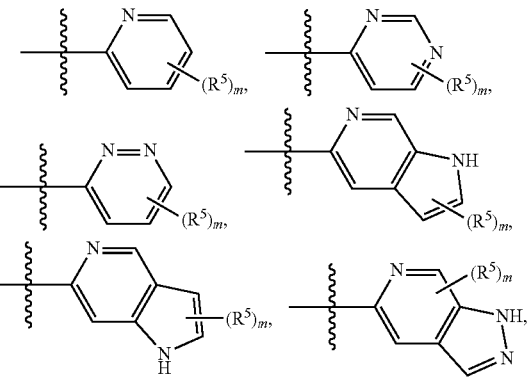

-continued

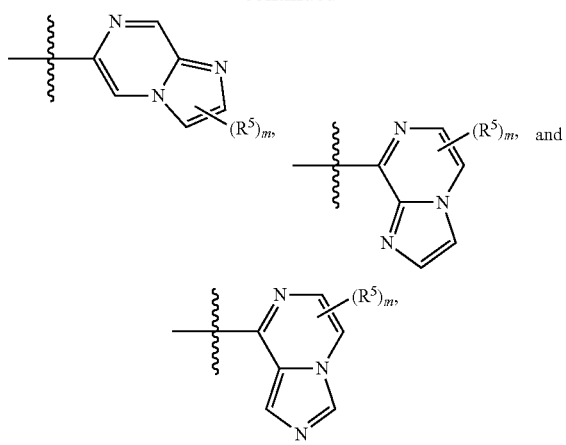

m is an integer of 0, 1 or 2 and $R^5$ is the same as defined in claim 1.

4. The compound of claim 1, which is represented by Formula (Ia):

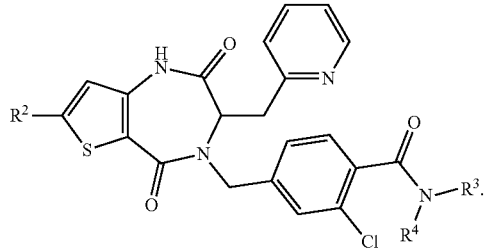

(Ia)

5. The compound of claim 1, which is represented by Formula (Ib):

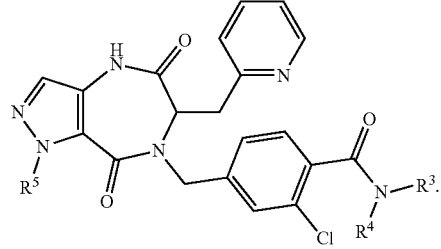

(Ib)

6. The compound according to claim 1, or a stereoisomer, a tautomer, or a pharmaceutically acceptable salt thereof; wherein: $R^3$ is hydrogen, $R^4$ is

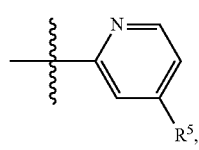

and $R^5$ is as defined in claim 1.

7. The compound of claim 1, which is represented by Formula (Ic):

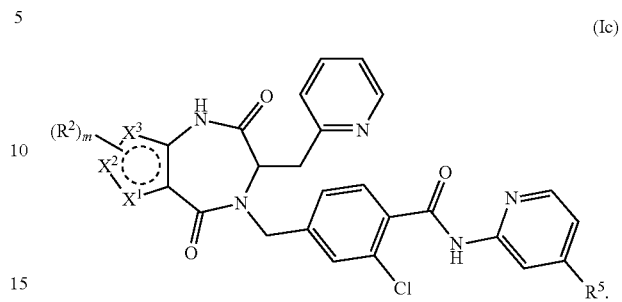

(Ic)

8. The compound of claim 1, which is represented by Formula (Id):

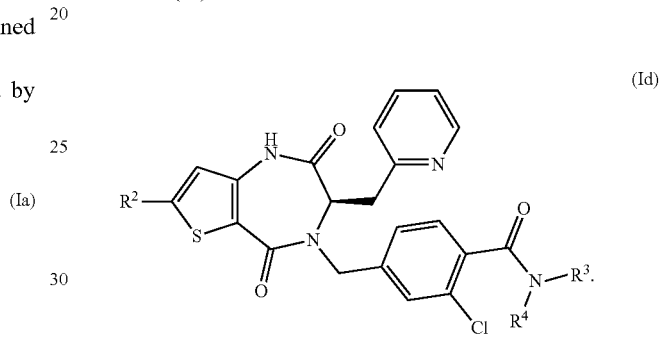

(Id)

9. The compound of claim 1, which is represented by Formula (Ie):

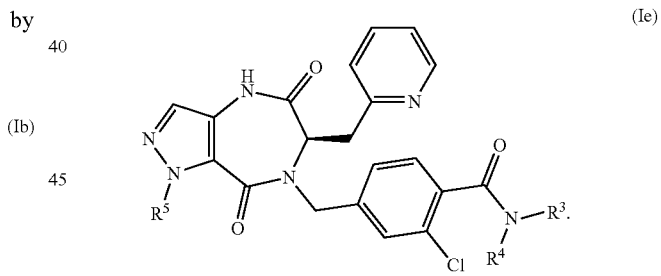

(Ie)

10. The compound of claim 1, which is represented by Formula (If):

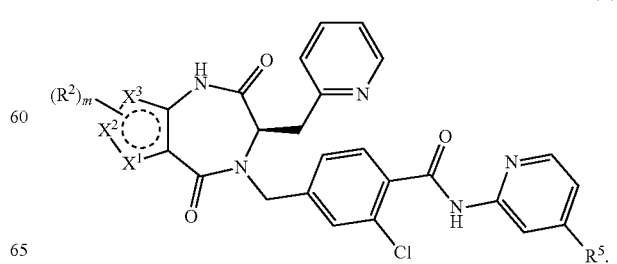

(If)

11. A compound which is represented by Formula (II):

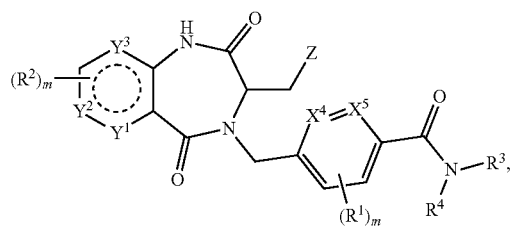

wherein
- $Y^1$, $Y^2$, and $X^3$ are each independently $CR^2$, or N, provided that at least one $Y^1$, $Y^2$, and $Y^3$ is N; $X^4$ and $X^5$ are each independently C(H) or N;
- m is an integer of 0, 1, or 2;
- Z is a 6- to 10-membered aryl or, 5- to 10-membered heteroaryl containing 1 to 3 heteroatoms independently selected from N, O, and S;
- $R^1$ and $R^2$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;
- $R^3$ and $R^4$ are each independently hydrogen, $C_{1-6}$ alkyl, alkylamino, haloalkyl, alkoxy, or haloalkoxy, 6- to 10-membered aryl, 5- to 10-membered heteroaryl containing 1 to 3 heteroatoms independently selected from N, O, and S, 3- to 10-membered carbocyclyl, or 4- to 10-membered heterocyclyl containing 1 to 3 heteroatoms independently selected from N, O, and S, wherein the aryl, heteroaryl, carbocyclyl, and heterocyclyl are independently substituted with 0 to 5 $R^5$; and
- $R^5$ is hydrogen, halo, cyano, hydroxyl, amino, $C_{1-6}$ alkyl, alkylamino, haloalkyl, hydroxyalkyl, hydroxycycloalkyl, aminoalkyl, alkoxyalkyl, haloalkoxyalkyl, alkoxy, haloalkoxy or —C(O)OR$^6$; and
- $R^6$ is hydrogen or $C_{1-6}$ alkyl, it should be understood by one skilled in the art that the dashed circle denotes an aromatic ring formed by $Y^1$, $Y^2$, $Y^3$, and the carbon atoms.

12. A compound selected from:

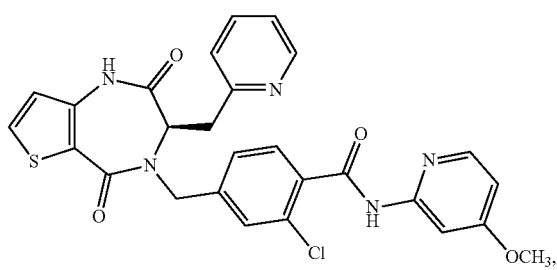

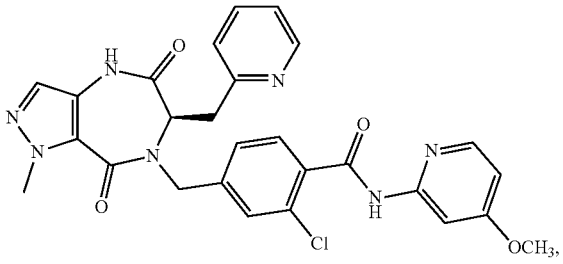

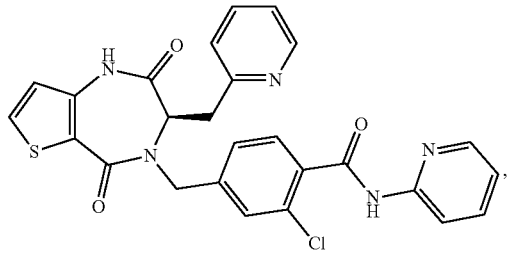

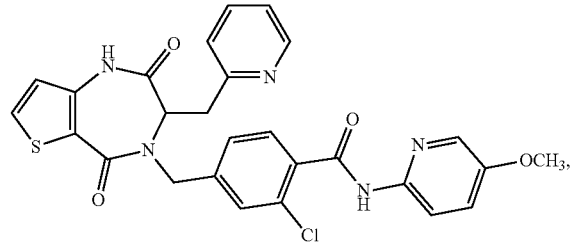

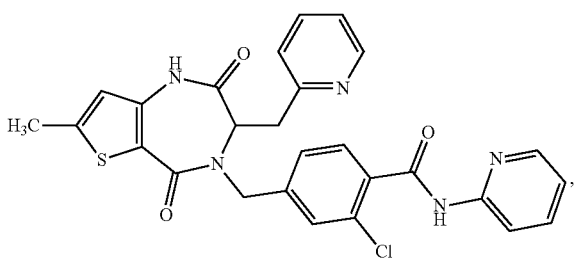

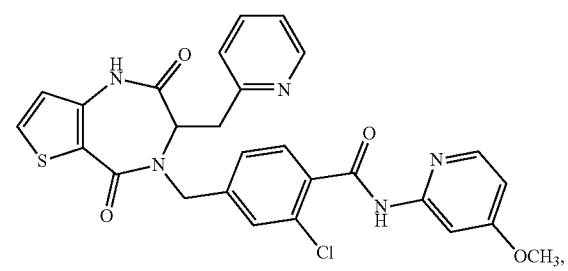

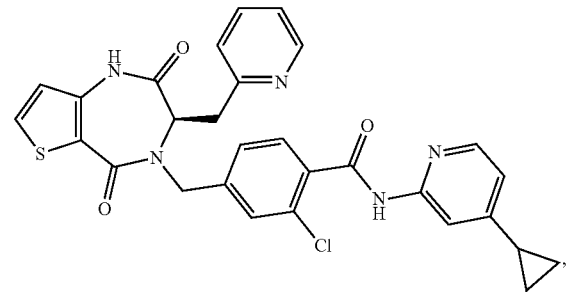

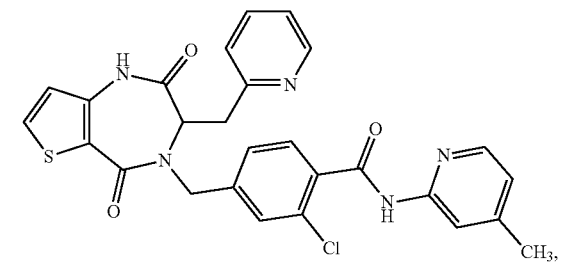

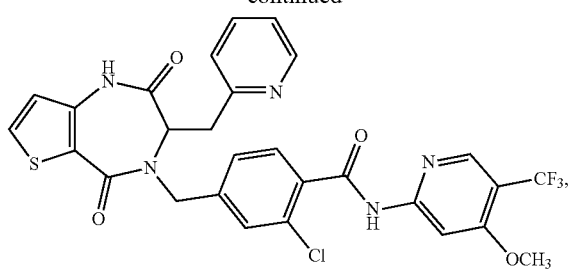
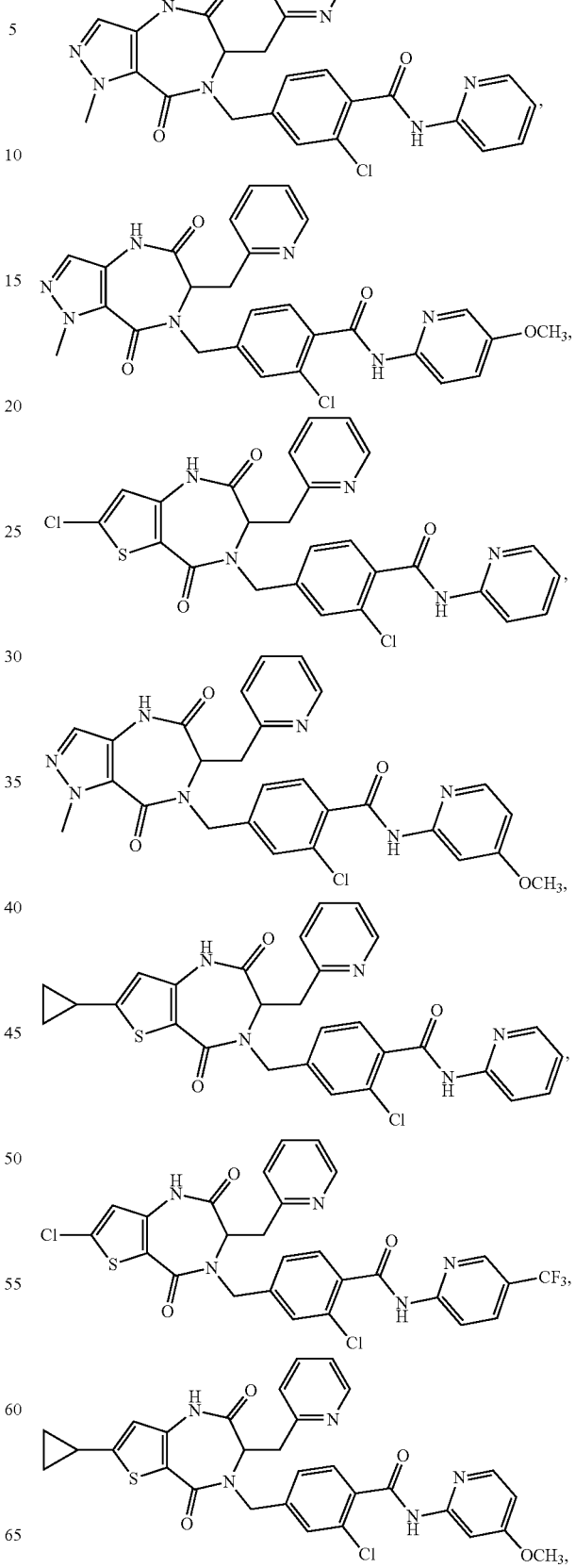

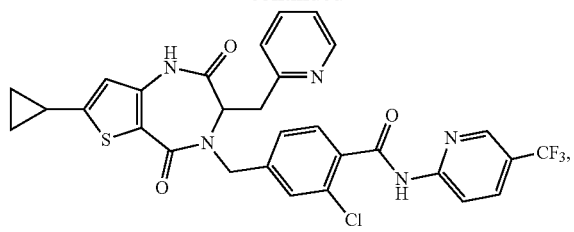
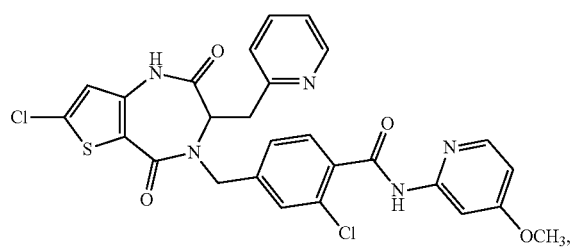
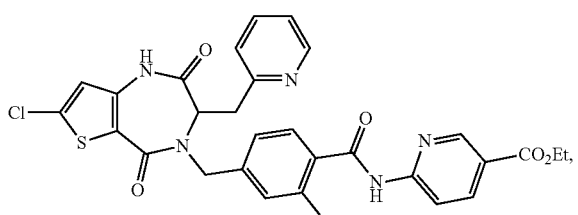
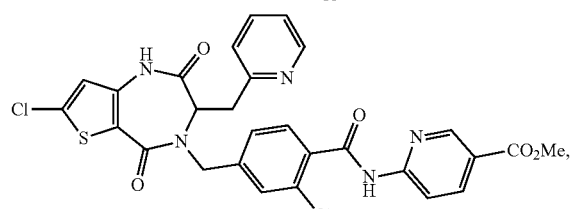
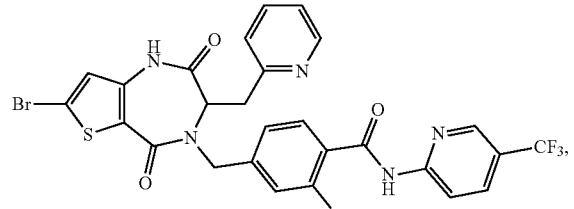
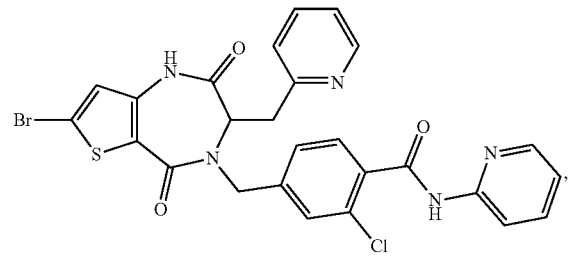
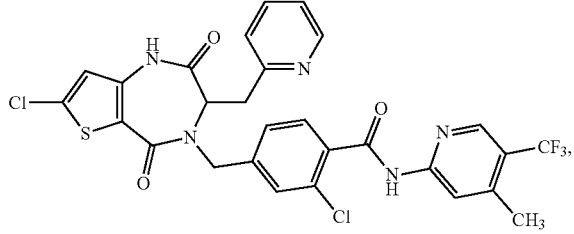
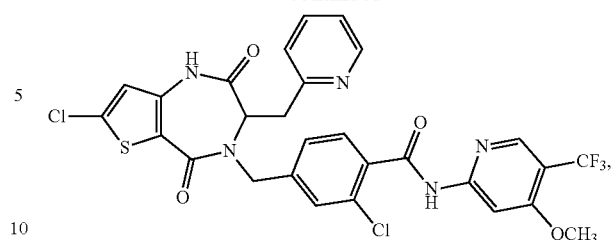
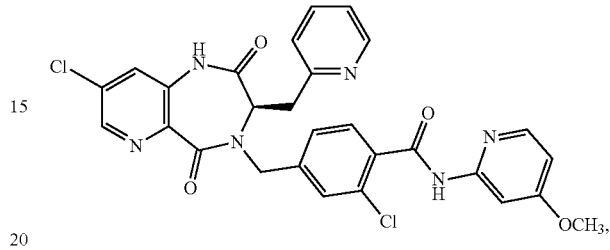
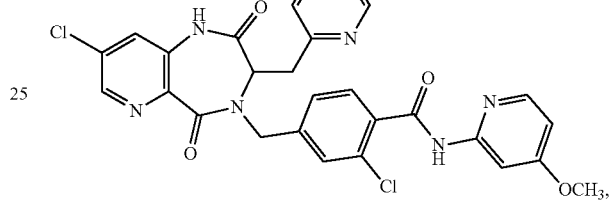
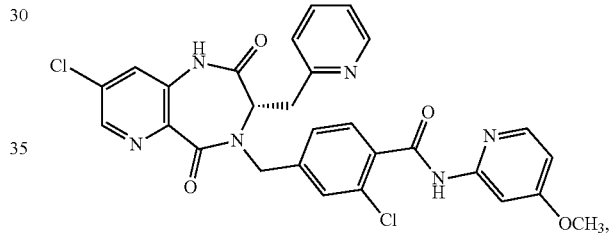
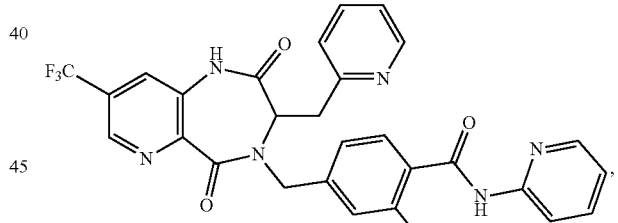
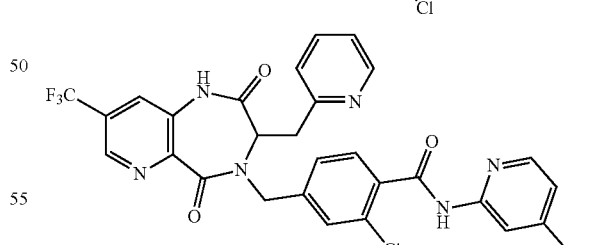
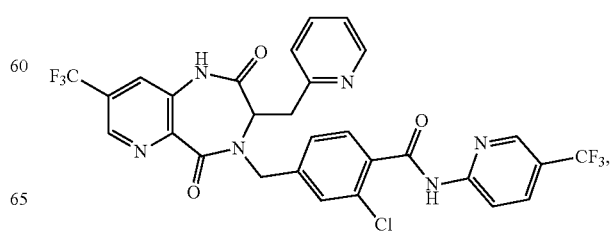

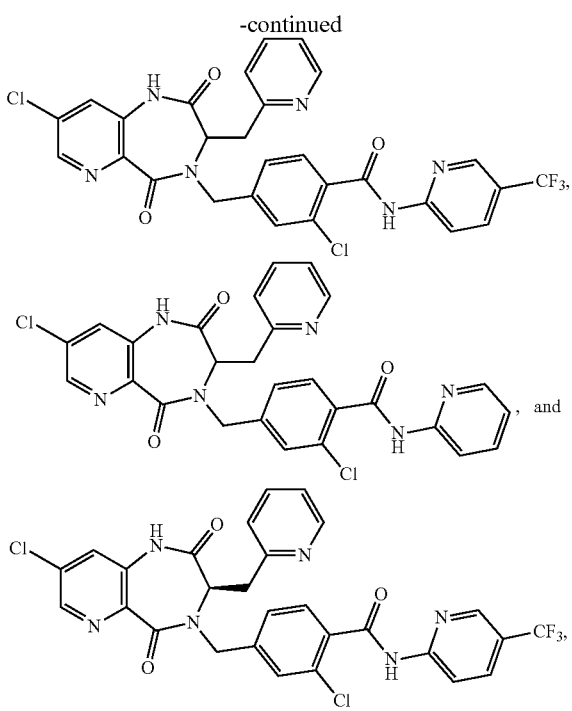

or a stereoisomer, a tautomer, or a pharmaceutically acceptable salt thereof.

13. A compound which is selected from:
(R)-2-chloro-4-((2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)benzamide;
(R)-2-chloro-N-(4-methoxypyridin-2-yl)-4-((1-methyl-5,8-dioxo-6-(pyridin-2-ylmethyl)-4,5,6,8-tetrahydropyrazolo[4,3-e][1,4]diazepin-7(1H)-yl)methyl)benzamide;
(R)-2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(4-methoxypyridin-2-yl)benzamide;
2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(4-methoxypyridin-2-yl)benzamide;
(R)-2-chloro-4-((2,5-dioxo-3-(pyridin-2-ylmethyl)-1,2,3,5-tetrahydro-4H-thieno[3,2-e][1,4]diazepin-4-yl)methyl)-N-(pyridin-2-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(5-methoxypyridin-2-yl)benzamide;
2-chloro-4-((7-methyl-2,5-dioxo-3-(pyridin-2-ylmethyl)-1,2,3,5-tetrahydro-4H-thieno[3,2-e][1,4]diazepin-4-yl)methyl)-N-(pyridin-2-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)benzamide;
2-chloro-4-((2,5-dioxo-3-(pyridin-2-ylmethyl)-1,2,3,5-tetrahydro-4H-pyrido[2,3-e][1,4]diazepin-4-yl)methyl)-N-(pyridin-2-yl)benzamide;
2-chloro-4-((2,5-dioxo-3-(pyridin-2-ylmethyl)-1,2,3,5-tetrahydro-4H-pyrido[2,3-e][1,4]diazepin-4-yl)methyl)-N-(5-methoxypyridin-2-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(4-methylpyridin-2-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(1H-pyrrolo[2,3-c]pyridin-5-yl)benzamide;
2-chloro-4-((2,5-dioxo-3-(pyridin-2-ylmethyl)-1,2,3,5-tetrahydro-4H-pyrido[2,3-e][1,4]diazepin-4-yl)methyl)-N-(4-methoxypyridin-2-yl)benzamide;
(R)-2-chloro-N-(4-cyclopropylpyridin-2-yl)-4-((2,5-dioxo-3-(pyridin-2-ylmethyl)-1,2,3,5-tetrahydro-4H-thieno[3,2-e][1,4]diazepin-4-yl)methyl)benzamide;
(R)-2-chloro-4-((2,5-dioxo-3-(pyridin-2-ylmethyl)-1,2,3,5-tetrahydro-4H-thieno[3,2-e][1,4]diazepin-4-yl)methyl)-N-(1H-pyrrolo[3,2-c]pyridin-6-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(6-methoxypyrimidin-4-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(imidazo[1,2-a]pyrazin-8-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(imidazo[1,5-a]pyrazin-8-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(4-methoxy-5-(trifluoromethyl)pyridin-2-yl)benzamide;
2-chloro-4-((5,8-dioxo-6-(pyridin-2-ylmethyl)-4,5,6,8-tetrahydro-7H-thiazolo[4,5-e][1,4]diazepin-7-yl)methyl)-N-(pyridin-2-yl)benzamide;
2-chloro-4-((5,8-dioxo-6-(pyridin-2-ylmethyl)-4,5,6,8-tetrahydro-7H-thiazolo[4,5-e][1,4]diazepin-7-yl)methyl)-N-(5-methoxypyridin-2-yl)benzamide;
2-chloro-4-((5,8-dioxo-6-(pyridin-2-ylmethyl)-4,5,6,8-tetrahydro-7H-thiazolo[4,5-e][1,4]diazepin-7-yl)methyl)-N-(4-methoxypyridin-2-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(1H-pyrazolo[3,4-d]pyrimidin-4-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(4-(trifluoromethyl)pyridin-2-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(5-(trifluoromethyl)pyridin-2-yl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(1H-pyrazolo[3,4-c]pyridin-5-yl)benzamide;
2-chloro-N-(4-cyclopropoxypyridin-2-yl)-4-((2,5-dioxo-3-(pyridin-2-ylmethyl)-1,2,3,5-tetrahydro-4H-thieno[3,2-e][1,4]diazepin-4-yl)methyl)benzamide;
2-chloro-4-((2,5-dioxo-3-(pyridin-2-ylmethyl)-1,2,3,5-tetrahydro-4H-thieno[3,2-e][1,4]diazepin-4-yl)methyl)-N-(5-methoxypyridazin-3-yl)benzamide;
4-((2,5-dioxo-3-(pyridin-2-ylmethyl)-1,2,3,5-tetrahydro-4H-thieno[3,2-e][1,4]diazepin-4-yl)methyl)-3-fluoro-N-(pyridin-2-yl)benzamide;
4-((2,5-dioxo-3-(pyridin-2-ylmethyl)-1,2,3,5-tetrahydro-4H-thieno[3,2-e][1,4]diazepin-4-yl)methyl)-3-fluoro-N-(5-methoxypyridin-2-yl)benzamide;
2-chloro-N-(4-(difluoromethoxy)pyridin-2-yl)-4-((2,5-dioxo-3-(pyridin-2-ylmethyl)-1,2,3,5-tetrahydro-4H-thieno[3,2-e][1,4]diazepin-4-yl)methyl)benzamide;

2-chloro-4-((2,5-dioxo-3-(pyridin-2-ylmethyl)-1,2,3,5-tetrahydro-4H-thieno[3,2-e][1,4]diazepin-4-yl)methyl)-N-(4-(trifluoromethoxy)pyridin-2-yl)benzamide;

2-chloro-4-((2,5-dioxo-3-(pyridin-2-ylmethyl)-1,2,3,5-tetrahydro-4H-thieno[3,2-e][1,4]diazepin-4-yl)methyl)-N-(imidazo[1,2-a]pyrazin-6-yl)benzamide;

4-((2,5-dioxo-3-(pyridin-2-ylmethyl)-1,2,3,5-tetrahydro-4H-thieno[3,2-e][1,4]diazepin-4-yl)methyl)-3-fluoro-N-(4-methoxypyridin-2-yl)benzamide;

2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(5-methoxypyridin-2-yl)benzamide;

6-((2,5-dioxo-3-(pyridin-2-ylmethyl)-1,2,3,5-tetrahydro-4H-thieno[3,2-e][1,4]diazepin-4-yl)methyl)-N-(pyridin-2-yl)nicotinamide;

5-((2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)picolinamide;

5-((2,5-dioxo-3-(pyridin-2-ylmethyl)-1,2,3,5-tetrahydro-4H-thieno[3,2-e][1,4]diazepin-4-yl)methyl)-N-(5-methoxypyridin-2-yl)picolinamide;

2-chloro-4-((1-methyl-5,8-dioxo-6-(pyridin-2-ylmethyl)-4,5,6,8-tetrahydropyrazolo[4,3-e][1,4]diazepin-7(1H)-yl)methyl)-N-(pyridin-2-yl)benzamide;

2-chloro-N-(5-methoxypyridin-2-yl)-4-((1-methyl-5,8-dioxo-6-(pyridin-2-ylmethyl)-4,5,6,8-tetrahydropyrazolo[4,3-e][1,4]diazepin-7(1H)-yl)methyl)benzamide;

2-chloro-4-((5,8-dioxo-6-(pyridin-2-ylmethyl)-4,5,6,8-tetrahydropyrazolo[4,3-e][1,4]diazepin-7(1H)-yl)methyl)-N-(5-methoxypyridin-2-yl)benzamide;

2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(pyridin-2-yl)benzamide;

2-chloro-4-((2-methyl-5,8-dioxo-6-(pyridin-2-ylmethyl)-4,5,6,8-tetrahydro-7H-thiazolo[4,5-e][1,4]diazepin-7-yl)methyl)-N-(pyridin-2-yl)benzamide;

6-((2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)nicotinamide;

6-((2,5-dioxo-3-(pyridin-2-ylmethyl)-1,2,3,5-tetrahydro-4H-thieno[3,2-e][1,4]diazepin-4-yl)methyl)-N-(5-methoxypyridin-2-yl)nicotinamide;

5-((2,5-dioxo-3-(pyridin-2-ylmethyl)-1,2,3,5-tetrahydro-4H-thieno[3,2-e][1,4]diazepin-4-yl)methyl)-N-(pyridin-2-yl)picolinamide;

2-chloro-N-(4-methoxypyridin-2-yl)-4-((1-methyl-5,8-dioxo-6-(pyridin-2-ylmethyl)-4,5,6,8-tetrahydropyrazolo[4,3-e][1,4]diazepin-7(1H)-yl)methyl)benzamide;

2-chloro-4-((5,8-dioxo-6-(pyridin-2-ylmethyl)-4,5,6,8-tetrahydropyrazolo[4,3-e][1,4]diazepin-7(1H)-yl)methyl)-N-(pyridin-2-yl)benzamide;

2-chloro-4-((2-methyl-5,8-dioxo-6-(pyridin-2-ylmethyl)-2,5,6,8-tetrahydropyrazolo[4,3-e][1,4]diazepin-7(4H)-yl)methyl)-N-(pyridin-2-yl)benzamide;

2-chloro-N-(4-methoxypyridin-2-yl)-4-((2-methyl-5,8-dioxo-6-(pyridin-2-ylmethyl)-2,5,6,8-tetrahydropyrazolo[4,3-e][1,4]diazepin-7(4H)-yl)methyl)benzamide;

2-chloro-N-(5-methoxypyridin-2-yl)-4-((2-methyl-5,8-dioxo-6-(pyridin-2-ylmethyl)-2,5,6,8-tetrahydropyrazolo[4,3-e][1,4]diazepin-7(4H)-yl)methyl)benzamide;

2-chloro-4-((2,5-dioxo-3-(pyridin-2-ylmethyl)-2,3-dihydro-1H-thieno[3,4-e][1,4]diazepin-4(5H)-yl)methyl)-N-(pyridin-2-yl)benzamide;

2-chloro-4-((2,5-dioxo-3-(pyridin-2-ylmethyl)-2,3-dihydro-1H-thieno[3,4-e][1,4]diazepin-4(5H)-yl)methyl)-N-(5-methoxypyridin-2-yl)benzamide;

2-chloro-4-((7-cyclopropyl-2,5-dioxo-3-(pyridin-2-ylmethyl)-1,2,3,5-tetrahydro-4H-thieno[3,2-e][1,4]diazepin-4-yl)methyl)-N-(pyridin-2-yl)benzamide;

2-chloro-4-((7-cyclopropyl-2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)benzamide;

4-((7-(tert-butyl)-2,5-dioxo-3-(pyridin-2-ylmethyl)-1,2,3,5-tetrahydro-4H-thieno[3,2-e][1,4]diazepin-4-yl)methyl)-2-chloro-N-(pyridin-2-yl)benzamide;

4-((7-(tert-butyl)-2,5-dioxo-3-(pyridin-2-ylmethyl)-1,2,3,5-tetrahydro-4H-thieno[3,2-e][1,4]diazepin-4-yl)methyl)-2-chloro-N-(4-methoxypyridin-2-yl)benzamide;

4-((7-(tert-butyl)-2,5-dioxo-3-(pyridin-2-ylmethyl)-1,2,3,5-tetrahydro-4H-thieno[3,2-e][1,4]diazepin-4-yl)methyl)-2-chloro-N-(5-methoxypyridin-2-yl)benzamide;

2-chloro-N-(4-methoxypyridin-2-yl)-4-((8-methyl-2,5-dioxo-3-(pyridin-2-ylmethyl)-1,2,3,5-tetrahydro-4H-pyrido[2,3-e][1,4]diazepin-4-yl)methyl)benzamide;

2-chloro-N-(4-methoxypyridin-2-yl)-4-((2-methyl-4,7-dioxo-6-(pyridin-2-ylmethyl)-2,6,7,8-tetrahydropyrazolo[3,4-e][1,4]diazepin-5(4H)-yl)methyl)benzamide;

2-chloro-4-((2-cyclopropyl-5,8-dioxo-6-(pyridin-2-ylmethyl)-2,5,6,8-tetrahydropyrazolo[4,3-e][1,4]diazepin-7(4H)-yl)methyl)-N-(4-methoxypyridin-2-yl)benzamide;

2-chloro-4-((2-cyclopropyl-5,8-dioxo-6-(pyridin-2-ylmethyl)-2,5,6,8-tetrahydropyrazolo[4,3-e][1,4]diazepin-7(4H)-yl)methyl)-N-(5-methoxypyridin-2-yl)benzamide;

2-chloro-N-(4-methoxypyridin-2-yl)-4-((2-methyl-5,8-dioxo-6-(pyridin-2-ylmethyl)-4,5,6,8-tetrahydro-7H-thiazolo[4,5-e][1,4]diazepin-7-yl)methyl)benzamide;

2-chloro-4-((2-cyclopropyl-5,8-dioxo-6-(pyridin-2-ylmethyl)-4,5,6,8-tetrahydro-7H-thiazolo[4,5-e][1,4]diazepin-7-yl)methyl)-N-(pyridin-2-yl)benzamide;

4-((2-(tert-butyl)-5,8-dioxo-6-(pyridin-2-ylmethyl)-4,5,6,8-tetrahydro-7H-thiazolo[4,5-e][1,4]diazepin-7l1)methyl)-2-chloro-N-(pyridin-2-yl)benzamide;

4-((2-(tert-butyl)-5,8-dioxo-6-(pyridin-2-ylmethyl)-4,5,6,8-tetrahydro-7H-thiazolo[4,5-e][1,4]diazepin-7l1)methyl)-2-chloro-N-(4-methoxypyridin-2-yl)benzamide;

2-chloro-4-((2-cyclopropyl-5,8-dioxo-6-(pyridin-2-ylmethyl)-4,5,6,8-tetrahydro-7H-thiazolo[4,5-e][1,4]diazepin-7-yl)methyl)-N-(4-methoxypyridin-2-yl)benzamide;

2-chloro-4-((2-cyclopropyl-5,8-dioxo-6-(pyridin-2-ylmethyl)-4,5,6,8-tetrahydro-7H-thiazolo[4,5-e][1,4]diazepin-7-yl)methyl)-N-(5-methoxypyridin-2-yl)benzamide;

2-chloro-4-((4,7-dioxo-6-(pyridin-2-ylmethyl)-2,6,7,8-tetrahydropyrazolo[3,4-e][1,4]diazepin-5(4H)-yl)methyl)-N-(pyridin-2-yl)benzamide;

2-chloro-4-((4,7-dioxo-6-(pyridin-2-ylmethyl)-2,6,7,8-tetrahydropyrazolo[3,4-e][1,4]diazepin-5(4H)-yl)methyl)-N-(5-methoxypyridin-2-yl)benzamide;

2-chloro-4-((4,7-dioxo-6-(pyridin-2-ylmethyl)-2,6,7,8-tetrahydropyrazolo[3,4-e][1,4]diazepin-5(4H)-yl)methyl)-N-(4-methoxypyridin-2-yl)benzamide;

2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(5-(trifluoromethyl)pyridin-2-yl)benzamide;

2-chloro-4-((7-cyclopropyl-2,5-dioxo-3-(pyridin-2-ylmethyl)-1,2,3,5-tetrahydro-4H-thieno[3,2-e][1,4]diazepin-4-yl)methyl)-N-(5-(trifluoromethyl)pyridin-2-yl)benzamide;

2-chloro-4-((1-methyl-5,8-dioxo-6-(pyridin-2-ylmethyl)-4,5,6,8-tetrahydroimidazo[4,5-e][1,4]diazepin-7(1H)-yl)methyl)-N-(pyridin-2-yl)benzamide;

2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(4-methoxypyridin-2-yl)benzamide;

2-chloro-N-(4-methoxypyridin-2-yl)-4-((1-methyl-5,8-dioxo-6-(pyridin-2-ylmethyl)-4,5,6,8-tetrahydroimidazo[4,5-e][1,4]diazepin-7(1H)-yl)methyl)benzamide;

2-chloro-4-((2-cyclopropyl-5,8-dioxo-6-(pyridin-2-ylmethyl)-4,5,6,8-tetrahydro-7H-thiazolo[4,5-e][1,4]diazepin-7-yl)methyl)-N-(5-(trifluoromethyl)pyridin-2-yl)benzamide;

2-chloro-4-((1-methyl-5,8-dioxo-6-(pyridin-2-ylmethyl)-4,5,6,8-tetrahydroimidazo[4,5-e][1,4]diazepin-7(1H)-yl)methyl)-N-(5-(trifluoromethyl)pyridin-2-yl)benzamide;

ethyl 6-(2-chloro-4-((7-chloro-2,5-dioxo-3-(pyridin-2-ylmethyl)-1,2,3,5-tetrahydro-4H-thieno[3,2-e][1,4]diazepin-4-yl)methyl)benzamido)nicotinate;

methyl 6-(2-chloro-4-((7-chloro-2,5-dioxo-3-(pyridin-2-ylmethyl)-1,2,3,5-tetrahydro-4H-thieno[3,2-e][1,4]diazepin-4-yl)methyl)benzamido)nicotinate;

(R)-4-((7-bromo-2,5-dioxo-3-(pyridin-2-ylmethyl)-1,2,3,5-tetrahydro-4H-thieno[3,2-e][1,4]diazepin-4-yl)methyl)-2-chloro-N-(5-(trifluoromethyl)pyridin-2-yl)benzamide;

2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(pyridin-2-yl)benzamide;

2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(4-methoxypyridin-2-yl)benzamide;

2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(5-(trifluoromethyl)pyridin-2-yl)benzamide;

4-((7-bromo-2,5-dioxo-3-(pyridin-2-ylmethyl)-1,2,3,5-tetrahydro-4H-thieno[3,2-e][1,4]diazepin-4-yl)methyl)-2-chloro-N-(pyridin-2-yl)benzamide;

2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(4-methoxy-5-(trifluoromethyl)pyridin-2-yl)benzamide;

2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(4-methyl-5-(trifluoromethyl)pyridin-2-yl)benzamide;

2-chloro-4-((7-chloro-2,5-dioxo-3-(pyridin-2-ylmethyl)-1,2,3,5-tetrahydro-4H-thieno[3,2-e][1,4]diazepin-4-yl)methyl)-N-(5-methoxypyridazin-3-yl)benzamide;

2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(5-methoxypyridazin-3-yl)benzamide;

(S)-2-chloro-N-(4-methoxypyridin-2-yl)-4-((1-methyl-5,8-dioxo-6-(pyridin-2-ylmethyl)-4,5,6,8-tetrahydropyrazolo[4,3-e][1,4]diazepin-7(1H)-yl)methyl)benzamide;

(R)-2-chloro-4-((2,5-dioxo-3-(pyridin-2-ylmethyl)-1,2,3,5-tetrahydro-4H-thieno[3,2-e][1,4]diazepin-4-yl)methyl)-N-(5-methoxypyridazin-3-yl)benzamide;

2-chloro-4-((2,5-dioxo-3-(pyridin-2-ylmethyl)-8-(trifluoromethyl)-1,2,3,5-tetrahydro-4H-pyrido[3,2-e][1,4]diazepin-4-yl)methyl)-N-(5-methoxypyridazin-3-yl)benzamide;

(S)-2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(4-methoxypyridin-2-yl)benzamide;

(R)-2-chloro-4-((8-chloro-2,5-dioxo-3-(pyridin-2-ylmethyl)-1,2,3,5-tetrahydro-4H-pyrido[3,2-e][1,4]diazepin-4-yl)methyl)-N-(5-(trifluoromethyl)pyridin-2-yl)benzamide;

or a stereoisomer, a tautomer, or a pharmaceutically acceptable salt thereof.

14. A pharmaceutical composition comprising a pharmaceutically acceptable carrier and a compound of claim 1, or a stereoisomer, a tautomer, or a pharmaceutically acceptable salt thereof.

15. A method of making a compound of claim 1 or a stereoisomer, a tautomer, or a pharmaceutically acceptable salt thereof according to Schemes 1 or 2 below:

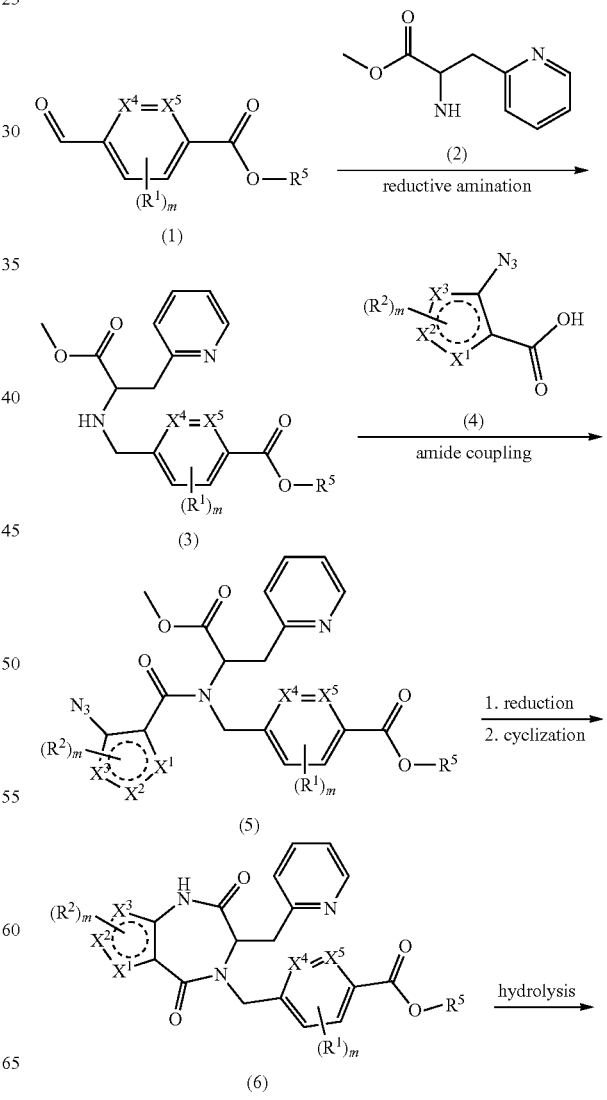

-continued

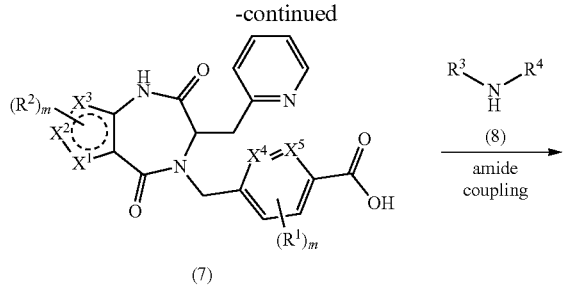
(7)

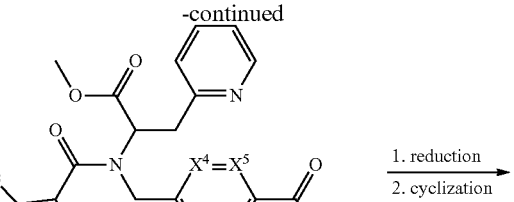
(8) amide coupling

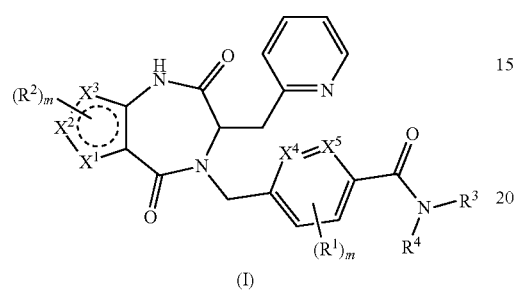
(I)

-continued

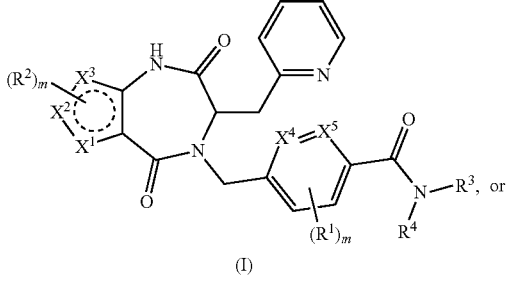
(13)

1. reduction
2. cyclization

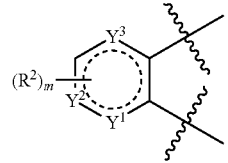
(I), or wherein m, $X^1$, $X^2$, $X^3$, $X^4$, $X^5$, $R^1$, $R^2$, $R^3$, $R^4$, $R^5$, and $R^6$ areas defined in claim 1, and wherein for Scheme I:
- joining intermediate 1 with intermediate 2 through a reductive amination to give intermediate 3;
- amide coupling intermediate 3 with carboxylic acid 4 to give amide 5;
- reducing amide 5 to give diazepinedione 6;
- hydrolyzing diazepinedione 6 to yield carboxylic acid 7;
- amide coupling amine intermediate 8 with carboxylic acid 7 to yield product I;

and wherein for Scheme II:
- amide coupling of amine intermediate 8 with carboxylic acid 9 to yield intermediate 10;
- vinylation of intermediate 10, followed by oxidative cleavage to give aldehyde intermediate 11;
- joining intermediate 11 with intermediate 2 to give intermediate 12;
- amide coupling of intermediate 12 with carboxylic acid 4 to give amide 13; and
- reducing amide 13 to yield product I.

16. A method of treating a *C. difficile* infection in a subject in need thereof, the method comprising administering a therapeutically-effective amount of a compound of claim 1 or a stereoisomer, a tautomer, or a pharmaceutically acceptable salt.

17. The method of claim 16, further comprising administering a therapeutically-effective amount of a second therapeutic agent comprising vancomycin, fidaxomicin, or metronidazole.

18. The compound according to claim 11, or a stereoisomer, a tautomer, or a pharmaceutically acceptable salt thereof; wherein the

SCHEME 2

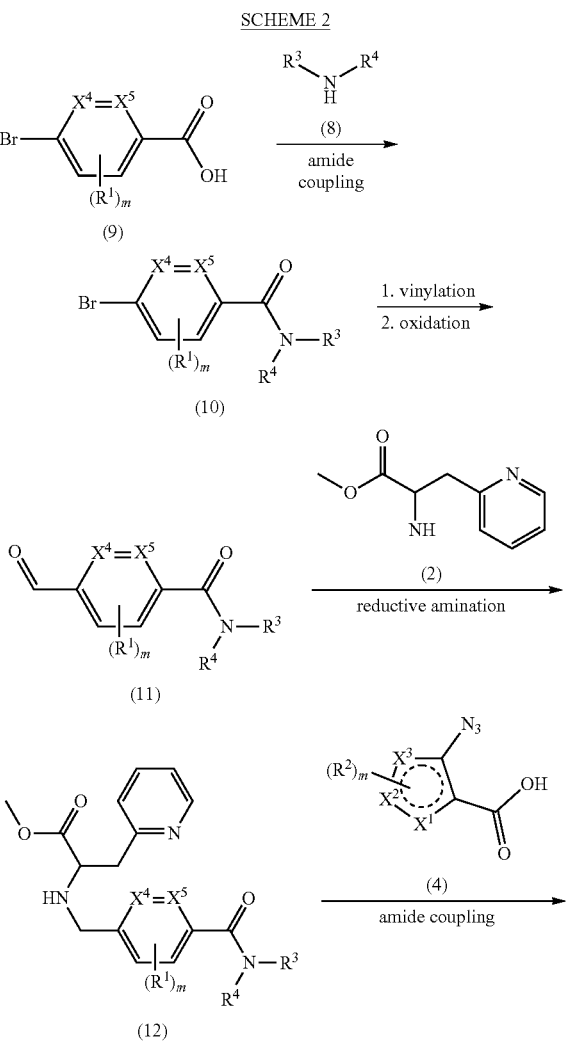

moiety is

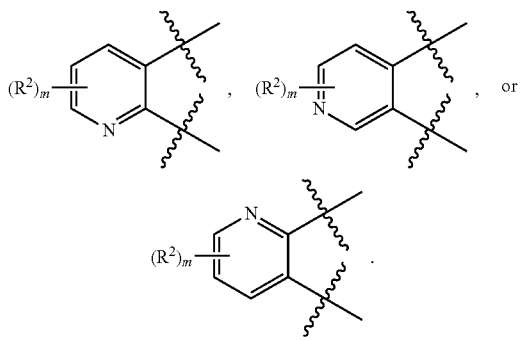

19. The compound according to claim 11, or a stereoisomer, a tautomer, or a pharmaceutically acceptable salt thereof; wherein:
$R^3$ is hydrogen and $R^4$ is selected from

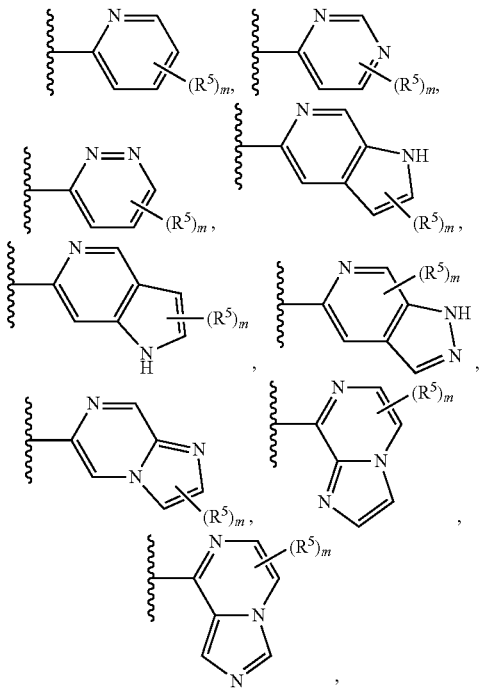

and m is an integer of 0, 1 or 2 and $R^5$ is the same as defined in claim 11.

20. The compound according to claim 11, or a stereoisomer, a tautomer, or a pharmaceutically acceptable salt thereof; wherein:
$R^3$ is hydrogen and $R^4$ is

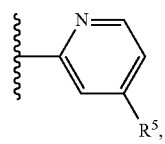

where $R^5$ is as defined in claim 11.

21. The compound of claim 11, which is represented by Formula (IIa):

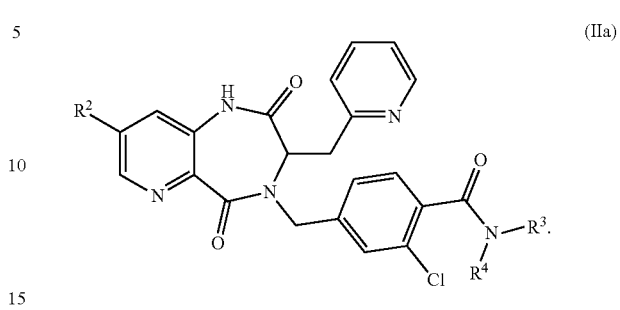

(IIa)

22. The compound of claim 11, which is represented by Formula (IIb):

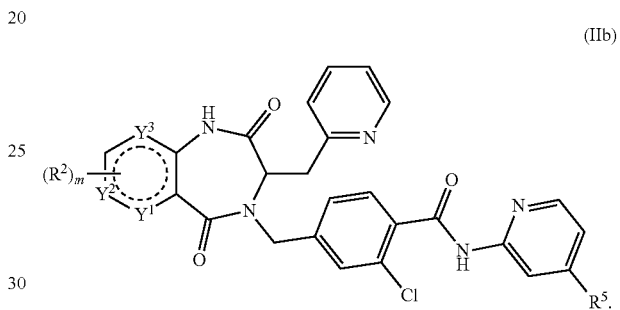

(IIb)

23. The compound of claim 11, which is represented by Formula (IIc):

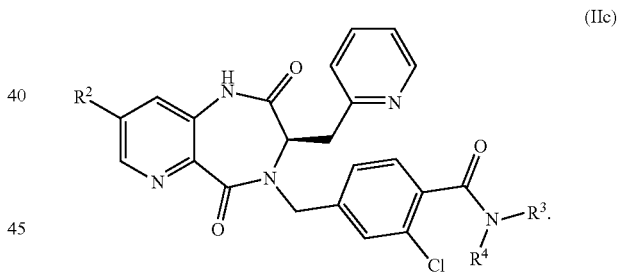

(IIc)

24. The compound of claim 11, which is represented by Formula (IId):

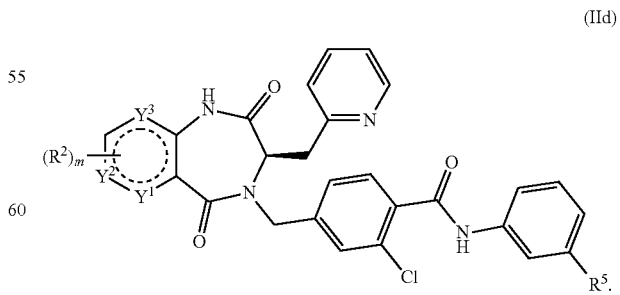

(IId)

* * * * *

UNITED STATES PATENT AND TRADEMARK OFFICE
CERTIFICATE OF CORRECTION

PATENT NO. : 11,919,868 B2
APPLICATION NO. : 17/684352
DATED : March 5, 2024
INVENTOR(S) : Michael James Genin et al.

Page 1 of 2

It is certified that error appears in the above-identified patent and that said Letters Patent is hereby corrected as shown below:

In the Claims

At Column 146, Lines 40-42, "4-((2-(tert-butyl)-5,8-dioxo-6-(pyridin-2-ylmethyl)-4,5,6,8-tetrahydro-7H-thiazolo[4,5-e][1,4]diazepin-711)methyl)-2-chloro-N-(pyridin-2-yl)benzamide;" should be -- 4-((2-(tert-butyl)-5,8-dioxo-6-(pyridin-2-ylmethyl)-4,5,6,8-tetrahydro-7H-thiazolo[4,5-e][1,4]diazepin-7-yl)methyl)-2-chloro-N-(pyridin-2-yl)benzamide; --.

At Column 146, Lines 43-46, "4-((2-(tert-butyl)-5,8-dioxo-6-(pyridin-2-ylmethyl)-4,5,6,8-tetrahydro-7H-thiazolo[4,5-e][1,4]diazepin-711)methyl)-2-chloro-N-(4-methoxypyridin-2-yl)benzamide;" should be -- 4-((2-(tert-butyl)-5,8-dioxo-6-(pyridin-2-ylmethyl)-4,5,6,8-tetrahydro-7H-thiazolo[4,5-e][1,4]diazepin-7-yl)methyl)-2-chloro-N-(4-methoxypyridin-2-yl)benzamide; --.

At Column 150, Lines 1-11, " 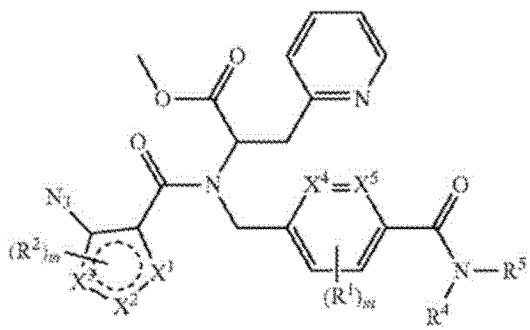 " should be

Signed and Sealed this
Twenty-second Day of October, 2024

Katherine Kelly Vidal
*Director of the United States Patent and Trademark Office*

CERTIFICATE OF CORRECTION (continued)
U.S. Pat. No. 11,919,868 B2

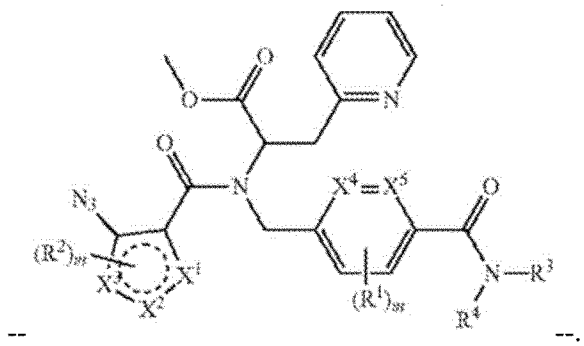

--                                                         --.

At Column 150, Line 26, "areas" should be -- are as --.

At Column 152, Lines 54-63, " 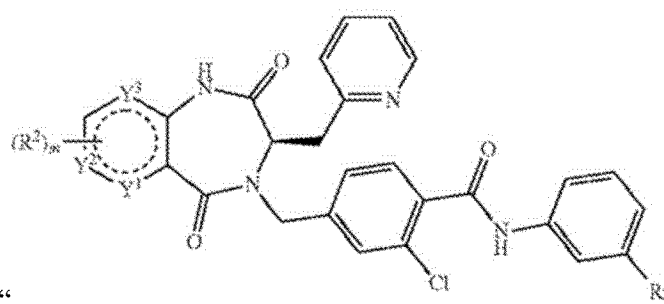 " should be

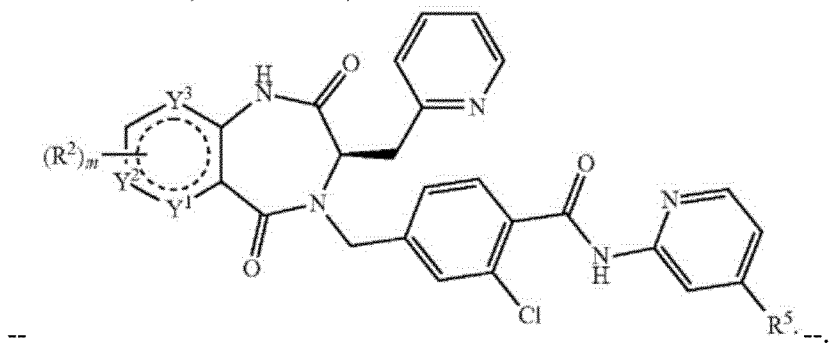

--                                                         --.